United States Patent
Lebel et al.

(10) Patent No.: US 6,577,899 B2
(45) Date of Patent: Jun. 10, 2003

(54) MICROPROCESSOR CONTROLLED AMBULATORY MEDICAL APPARATUS WITH HAND HELD COMMUNICATION DEVICE

(75) Inventors: Ronald J. Lebel, Sherman Oaks, CA (US); Varaz Shahmirian, Northridge, CA (US); Sam W. Bowman, IV, Valencia, CA (US); Timothy J. Starkweather, Simi Valley, CA (US); Daniel H. Villegas, Granada Hills, CA (US); David Y. Choy, San Gabriel, CA (US); Philip T. Weiss, Pasadena, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 269 days.

(21) Appl. No.: 09/768,221

(22) Filed: Jan. 22, 2001

(65) Prior Publication Data

US 2002/0049480 A1 Apr. 25, 2002

Related U.S. Application Data

(60) Provisional application No. 60/177,414, filed on Jan. 21, 2000.

(51) Int. Cl.[7] .............................................. A61N 1/08
(52) U.S. Cl. ........................... 607/60; 604/67; 128/903
(58) Field of Search .................. 128/903, 923; 600/300, 301, 310, 311, 509, 510, 529; 604/65, 66, 67; 607/4, 5, 7, 9, 17, 18, 30, 31, 32, 60

(56) References Cited

U.S. PATENT DOCUMENTS

| | | | |
|---|---|---|---|
| 4,871,351 A | 10/1989 | Feingold | 604/66 |
| 5,368,562 A | 11/1994 | Blomquist et al. | 604/65 |
| 5,456,692 A | 10/1995 | Smith et al. | 607/31 |
| 5,464,435 A * | 11/1995 | Neumann | 607/9 |
| 5,620,472 A * | 4/1997 | Rahbari | 607/27 |
| 5,630,710 A | 5/1997 | Tune et al. | 417/326 |
| 5,647,854 A | 7/1997 | Olsen et al. | 604/174 |

(List continued on next page.)

FOREIGN PATENT DOCUMENTS

| | | |
|---|---|---|
| EP | 0472411 A1 | 8/1991 |
| WO | WO 84/03218 | 8/1984 |
| WO | WO 95/02426 | 1/1995 |
| WO | WO 96/03168 | 2/1996 |
| WO | WO 00/19887 | 4/2000 |

OTHER PUBLICATIONS

PCT International Search Report as issued in International Application No. PCT/US01/02153, Mailing Date Apr. 29, 2002.

*Primary Examiner*—Willis R. Wolfe
(74) *Attorney, Agent, or Firm*—Foley & Lardner

(57) ABSTRACT

An implantable infusion pump possesses operational functionality that is, at least in part, controlled by software operating in two processor ICs which are configured to perform some different and some duplicate functions. The pump exchanges messages with an external device via telemetry. Each processor controls a different part of the drug infusion mechanism such that both processors must agree on the appropriateness of drug delivery for infusion to occur. Delivery accumulators are incremented and decremented with delivery requests and with deliveries made. When accumulated amounts reach or exceed, quantized deliverable amounts, infusion is made to occur. The accumulators are capable of being incremented by two or more independent types of delivery requests. Operational modes of the infusion device are changed automatically in view of various system errors that are trapped, various system alarm conditions that are detected, and when excess periods of time lapse between pump and external device interactions.

49 Claims, 5 Drawing Sheets

U.S. PATENT DOCUMENTS

| | | | |
|---|---|---|---|
| 5,658,133 A | 8/1997 | Anderson et al. | 417/63 |
| 5,658,250 A | 8/1997 | Blomquist et al. | 604/65 |
| 5,669,877 A | 9/1997 | Blomquist | 604/67 |
| 5,695,473 A | 12/1997 | Olsen | 604/153 |
| 5,788,669 A | 8/1998 | Peterson | 604/65 |
| 5,810,771 A | 9/1998 | Blomquist | 604/65 |
| 5,876,370 A | 3/1999 | Blomquist | 604/65 |
| 5,904,708 A | 5/1999 | Goedeke | 607/18 |
| 5,935,099 A | 8/1999 | Peterson et al. | 604/65 |
| 5,935,106 A | 8/1999 | Olsen | 417/474 |
| 6,024,539 A | 2/2000 | Blomquist | 417/63 |
| 6,123,686 A | 9/2000 | Olsen et al. | 417/26 |
| 6,190,324 B1 * | 2/2001 | Kieval et al. | 600/510 |
| 6,248,080 B1 * | 6/2001 | Miesel et al. | 600/311 |
| 6,400,987 B1 * | 6/2002 | Garberoglio | 607/18 |
| 6,406,426 B1 * | 6/2002 | Reuss et al. | 600/300 |
| 6,427,088 B1 * | 7/2002 | Bowman et al. | 607/60 |

* cited by examiner

MICROPROCESSOR CONTROLLED AMBULATORY MEDICAL APPARATUS WITH HAND HELD COMMUNICATION DEVICE

RELATED APPLICATIONS:

This application claims the benefit of prior filed U.S. Provisional Patent Application No. 60/177,414; filed Jan. 21, 2000, by Ronald J. Lebel, et al., and entitled "Medical Apparatus and Method Including an Implantable Device and an External Communication Device". The entirety of this provisional application is hereby incorporated herein by this reference, including appendices filed therewith and any references incorporated therein by reference, as if set forth in full herein.

FIELD OF THE DISCLOSURE

This invention relates generally to ambulatory medical systems that include a microprocessor controlled ambulatory medical device and a separate control device that communicate via telemetry where the medical device has enhanced functionality, safety features, failure detection, and/or alarming capabilities. Preferred embodiments relate to implantable infusion pumps and external devices for communicating therewith.

BACKGROUND

Implantable infusion pumps for dispensing controlled volumes of a drug (e.g. insulin) have been proposed and even attempts at implementation and commercialization made.

One such pump is the MMT2001 Implantable Pump System as sold by Minimed Inc. of Northridge, Calif. This device presented the user with the ability to perform basic infusion actions such as the delivery of a basal rate, delivery of a temporary basal rate, or the delivery of a meal bolus. The user was, however, not presented with the ability to perform more sophisticated delivery related operations that may be desirable for optimum control of blood glucose level. When using this system three delivery options exist: (1) delivery of a standard but programmable basal rate, (2) delivery of a standard basal rate and a meal bolus simultaneously, or (3) delivery of a temporary basal rate either immediately or at a programmable start time within a specifiable start time. In this system not only could a meal bolus and a temporary basal rate not occur at the same time, they could not be programmed into the system when the other was already programmed but delivery not yet completed even though no overlap in delivery between the two amounts might exist. As such the user could only program one variable rate into the system at a time, even in the event that several variable rates may be desired to follow one another. As such, this system is less than optimal with regard to user convenience in programming his/her insulin treatment.

The system also suffered from an external controller that was large, hard to carry and awkward to use. The controller dimensions are 6.0 inches by 3.5 inches by 1.3 inches with a display that is a small fraction of the size of the face of the controller. The controller included a cover plate that would close over the display area when not in use and would be opened during use. More particularly, during programming the cover plate is opened at a ninety-degree angle relative to the front of the display to allow viewing of the display and to allow positioning of the cover plate immediately over the site of the infusion pump so that successful telemetry communication may occur. As such the system does not supply delivery or system status related information to the user accept at the times that the user elects to open and turn on his/her controller.

The system further suffers from the inability of the implantable device to send out unsolicited telemetry messages to the controller concerning operational conditions within the implantable device. As such, system conditions within the implantable device (other than communication related failures) are primarily conveyed to the user via an auditory alarm that is internal to the implantable device.

The system further suffers from the entire operational history of the pump being subject to loss as this historical data is only held in the controller.

The system further suffered from a relatively short life for the implantable device of approximately 2.5 years.

Based on the above noted shortcomings, and other shortcomings of systems in the field, a need exists for improved systems that offer enhanced programming capabilities, enhanced user interface capabilities, reduced controller size, enhanced operational performance, enhanced security of system/patient historical data, enhanced safety features, and/or enhanced implantable device life.

It is believed that related shortcoming may exist in other ambulatory medical devices as well, such as in externally carried infusion pumps, implantable pacemakers, implantable defibrillators, implantable neural stimulators, implantable physiological sensors, externally carried physiologic sensors, and the like.

SUMMARY OF THE INVENTION

It is a first object of certain aspects of the invention to enhance programming capabilities for ambulatory medical systems and in particular for implantable infusion pump systems.

It is a second object of certain aspects of the invention to enhance user interface capabilities in ambulatory medical systems and in particular for implantable infusion pump systems.

It is a third object of certain aspects of the invention to reduce system size for patient convenience in ambulatory medical systems and in particular for implantable infusion pump systems.

It is a fourth object of certain aspects of the invention to enhance operational performance of ambulatory medical systems and in particular for implantable infusion pump systems.

It is a fifth object of certain aspects of the invention to enhance security of system/patient historical data.

It is a sixth object of certain aspects of the invention to enhance the operational safety of ambulatory medical systems and in particular of implantable infusion pump systems.

It is a seventh object of certain aspects of the invention to enhance longevity of ambulatory medical systems and in particular of implantable infusion pump systems.

Other objects and advantages of various aspects of the invention will be apparent to those of skill in the art upon review of the teachings herein. The various aspects of the invention set forth below as well as other aspects of the invention not specifically set forth below but ascertained from the teachings found herein, may address the above noted objects or other objects ascertained from the teachings herein individually or in various combinations. As such, it is intended that each aspect of the invention address at least one of the above noted objects or address some other object that will be apparent to one of skill in the art from a review of the teachings herein. It is not intended that all, or even a portion of these objects, necessarily be addressed by any single aspect of the invention even though that may be the case with regard to some aspects.

A first aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein one of the medical device is configured to emit an audio alarm signal including a plurality of tones emitted in a predetermined sequence.

A second aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device is capable of being programmed to perform a selected function, at a future time, if the medical device fails to receive a selected message from the communication device during a predefined period of time or at a predefined time.

In a specific variation of the second aspect of the invention the medical device includes at least one of (1) an implantable infusion pump for selectively dispensing a selected drug, (2) an implantable infusion pump for selectively dispensing insulin, (3) an implantable sensor for sensing a selected state of the body, (4) an implantable sensor for sensing glucose level, or (5) an implantable electrode for selectively stimulating a portion of the body of the patient.

In a specific variation of the second aspect of the invention the selected function causes the medical device to change from a first operational state to a second operational state. In a further variation the selected message is any valid message that is received by the medical device.

In a specific variation of the second aspect of the invention the selected function includes the medical device ceasing delivery of medically significant amounts of the drug. In a further variation the predefined period of time is restarted each time a valid message is received from the communication device.

In a specific variation of the second aspect of the invention the communication device is programmed to alarm prior to the medical device performing the selected function, so as to give the patient an opportunity to send a message from the communication device to the medical device to prior to execution of the selected function.

A third aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device further includes an MD alarm under control of the MD processor, and the communication device further includes a CD alarm under control of the CD processor, and wherein the communication device is programmed to activate the CD alarm, in a selected circumstance, prior to the medical device directly sounding the MD alarm, such that a patient is signaled that a selected circumstance will occur, thereby providing an opportunity for the patient to acknowledge the selected circumstance so that the MD alarm may be de-asserted or the selected circumstance removed prior to the physical sounding of the MD alarm.

A fourth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein an identical application specific integrated circuit (ASIC) is used in both the medical device and in the communication device, and wherein the MD processor includes the ASIC and the CD processor includes the ASIC.

In a specific variation of the fourth aspect of the invention, the ASIC further includes a telemetry modulator, a telemetry demodulator, and memory, and further includes at least one of (1) a timer module, (2) an alarm driver, (3) an A/D converter, (4) a first synchronous serial interface, (5) a second synchronous serial interface, (6) a first treatment or monitoring device driver, (7) a second treatment or monitoring device driver, (8) a memory decoder, or (9) ROM memory.

A fifth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the MD processor, an MD telemetry modulator, and MD demodulator are incorporated into a single application specific integrated circuit.

In a specific variation of the fifth aspect of the invention, the application specific integrated circuit further includes at least three of (1) an A/D converter, (2) a timer module, (3) an alarm driver, (4) a first synchronous serial interface, (5) a second synchronous serial interface, (6) a first treatment or monitoring device driver, (7) a second treatment or monitoring device driver, (8) a memory decoder, (9) a ROM memory, or (10) an SRAM memory.

A sixth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the MD processor, an MD memory, and MD analog components are incorporated into a single application specific integrated circuit (ASIC).

In specific variation of the sixth aspect of the invention, the application specific integrated circuit further includes a telemetry modulator, a telemetry demodulator, and memory, and further includes at least one of (1) a timer module, (2) an alarm driver, (3) an A/D converter, (4) a first synchronous serial interface, (5) a second synchronous serial interface, (6) a first treatment or monitoring device driver, (7) a second treatment or monitoring device driver, (8) a memory decoder, or (9) ROM. In a further variation, the analog components include at least one of (1) an analog to digital converter, (2) an analog telemetry module, or (3) a crystal oscillator module.

A seventh aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the MD processor includes a 16 bit processor and is incorporated into an application specific integrated circuit.

In a specific variation of the seventh aspect of the invention, the ASIC further includes a telemetry modulator, a telemetry demodulator, and memory, and further includes at least one of (1) a timer module, (2) an alarm driver, (3) an A/D converter, (4) a first synchronous serial interface, (5) a second synchronous serial interface, (6) a first treatment or monitoring device driver, (7) a second treatment or monitoring device driver, (8) a memory decoder, or (9) ROM.

An eighth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein at least one of the medical device and the communication device includes a plurality of electronic modules, wherein at least two of the modules are powered with different voltages.

A specific variation of the eighth aspect of the invention provides the plurality of electronic modules are located within the same application specific integrated circuit. A further variation provides an analog-to-digital converter within the includes a voltage up converter and is included in the ASIC.

A ninth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device has a SEEPROM and a static RAM that interface with the MD processor.

A tenth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the communication device has a SEEPROM and a static RAM that interface with the CD processor.

A eleventh aspect of the invention provides a medical system that includes (a) an ambulatory medical device (MD)

that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device includes an infusion pump for selectively dispensing a drug and a sensor for detecting a state of the body, and wherein the at least one MD processor controls, at least in part, the sensor and the pump.

A twelfth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the MD processor is incorporated into an application specific integrated circuit that additionally incorporates internal RAM, internal ROM and at least one of the following (1) a synchronous serial interface, (2) piezo alarm driver, (3) pump driver control, (4) SEEPROM interface, (5) timer module, (6) watchdog timer, or (7) digital modulation and demodulation.

A thirteenth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device, when fully operating, consumes more than about 12 $\mu$W and when in a stand by power-saving mode, consumes less than about 100 $\mu$W.

In a specific variation of the thirteenth aspect of the invention, the fully operational state consumes no more than about 4 milliamps and the stand by power saving state consumes less than about 25 $\mu$A.

A fourteenth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the at least one MD processor includes at least two MD processors.

In a specific variation of the fourteenth aspect of the invention the two MD processors are programmed to perform different functions. In a further variation the two MD processors comprise a first MD processor and a second MD processor and wherein the first MD processor controls telemetry based communications and the second MD processor controls non-telemetry based communications.

In a specific variation of the fourteenth aspect of the invention the two MD processors are implemented in the form of two separate application specific integrated circuits along.

In a specific variation of the fourteenth aspect of the invention the two MD processors operate off the same crystal oscillator and wherein a first frequency signal from the crystal oscillator is used in the creation of a plurality of different frequency clock signals. In a further variation a timing signal generated by a second oscillator is compared to a timing signal of at least one of the different frequency clock signals. In a further variation either the second oscillator includes a crystal oscillator circuit or the second oscillator includes an RC oscillator circuit.

In a specific variation of the fourteenth aspect of the invention the at least two MD processors comprise a first MD processor and a second MD processor and wherein the first MD processor monitors at least one operation of the second MD processor.

In a specific variation of the fourteenth aspect of the invention the medical device provides a treatment to the body of the patient and wherein the at least two MD processors comprise a first MD processor and a second MD processor, respectively, and wherein appropriate operation of both the first and second MD processors are required for the medical device to provide a medically significant treatment to the body of the patient.

In a specific variation of the fourteenth aspect of the invention the two MD processors are capable of controlling telemetry operations and wherein the system is configured to have a single MD processor control telemetry transmission or reception at any one time.

In a specific variation of the fourteenth aspect of the invention the two MD processors comprise a first MD processor and a second MD processor and wherein the first MD processor receives data from a device that senses a state of the body while the second MD processor transmits as well as receives data from the device that senses.

In a specific variation of the fourteenth aspect of the invention the at least two processors are formed on a single die.

A fifteenth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein at least one of the medical device and the communication device includes a plurality of electronic modules, wherein at least one of the modules is at least a portion of the time switched from an active state to a power saving state (e.g. static state) when not in use and switched again to an active state when needed.

In a specific variation of the fifteenth aspect of the invention, at least one of the following will occur, at least one module is switched from an active state to an inactive state by operation of software, at least one module is switched from a power saving state to an active state by operation of software, at least one module is switched from an active state to an inactive state by operation of hardware, at least one module is switched from a power saving state to an active state by operation of hardware, at least one of the plurality of electronic modules is switched from an active state to a power saving state by withdrawing power from the module, or at least one of the plurality of electronic modules is switched from an active state to a power saving state by withdrawing a clock signal from the module.

In a specific variation of the fifteenth aspect of the invention the plurality of electronic modules comprise one or more of (1) a CPU, (2) ROM, (3) a RAM module, (4) a synchronous serial interface, (5) an audio alarm driver, (6) a pump driver, (7) a SEEPROM, (8) an analog-to-digital converter, (9) a telemetry system, (8) a bit map LCD, (9) a sensor driving circuit, (10) a voltage divider circuit, (11) a vibration alarm driver, or (12) a timer module.

In a specific variation of the fifteenth aspect of the invention at least one MD processor includes a CPU module and a plurality of other electronic modules, or at least one CD processor includes a CPU module and a plurality of other electronic modules.

In a specific variation of the fifteenth aspect of the invention at least one MD processor includes a single application specific integrated circuit, or at least one CD processor includes a single application specific integrated circuit.

A sixteenth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein at least one MD processor includes an application specific integrated circuit, and the application specific integrated circuit is configured to monitor an electrical activity of a first component or module.

In a specific variation of the sixteenth aspect of the invention the monitored electrical activity is compared to a predefined value, range of values, or waveform. In a further variation the comparison is used to ensure that the first component or module is operating under acceptable conditions.

In a specific variation of the sixteenth aspect of the invention the first component or module is located either within the application specific integrated circuit, or is located external to the application specific integrated circuit.

A seventeenth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein a first portion of the medical device is located in at least a first biocompatible housing and a second portion of the medical device is located in a second separated biocompatible housing, wherein the first and second housings are functionally connected.

In a specific variation of the seventeenth aspect of the invention the medical device includes an implantable infusion pump for selectively dispensing a drug and wherein a battery for powering the medical device is located in the first housing and a reservoir for holding a supply of the drug is located within the second housing, and wherein the functional connection includes a lead. In a further variation the invention the processor and the telemetry system are also located within the first housing and wherein a pumping mechanism is located within the second housing.

In a specific variation of the seventeenth aspect of the invention the medical device includes an implantable sensor for sensing a selected state of the body, wherein the medical device further includes a reservoir and a pumping mechanism for dispensing a desired drug from the reservoir to the body of the patient, and wherein the pumping mechanism and the reservoir are in the first housing and the sensor is in the second housing, and wherein the functional connection includes a telemetry system or a lead.

A eighteenth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device includes a rechargeable battery and a non-rechargeable battery.

In a specific variation of the eighteenth aspect of the invention the medical device automatically switches from the rechargeable battery to the non-rechargeable battery when a voltage of the rechargeable battery falls below a predefined level. In a further variation the medical device automatically switches from the non-rechargeable battery when the voltage of the rechargeable battery rises to a certain level.

In a specific variation of the eighteenth aspect of the invention the rechargeable battery is charged by induction or through a conductive path established by at least one hypodermic needle.

A nineteenth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device includes a component that requires activation to perform an intended function and wherein the activation state for the component is monitored, at least during preselected periods, by a monitoring circuit.

In a specific variation of the nineteenth aspect of the invention circuitry or a processor running a program is provided that causes an estimated activation time, for the component, to move incrementally closer to an optimal activation time based on a comparison between a desired activation level and an activation level resulting from activating the component for the estimated activation time.

In a specific variation of the nineteenth aspect of the invention the activation state is monitored by monitoring at least one of voltage, current, charge supplied, energy supplied, or power supplied for a given period of time.

A twentieth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein events of at least one selected type of activity are retained within a log within the medical device.

In a specific variation of the twentieth aspect of the invention the events retained in the log are provided with a time stamp indicative of when the activity occurred based on a continuously incrementing clock and a predefined point in time, or wherein the events are retained in the log with a time stamp indicative of the actual time of day.

In a specific variation of the twentieth aspect of the invention the medical device includes a glucose sensor and an implantable insulin pump wherein the events comprise periodic glucose values and insulin infusion rates or values. In a further variation the glucose sensor is an implantable sensor and obtained glucose values are automatically entered into a log or the glucose sensor is an external sensor and the glucose values are entered automatically into a log or are entered manually into the communication device and then entered into a log.

A twenty-first aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device includes a reservoir capable of containing a drug and a pumping mechanism for transferring the drug from the reservoir to the body of a patient, wherein the communication device is capable of being programmed with at least two quantities relating to drug delivery, and wherein the medical device is configured to deliver a drug based on the combined amounts dictated by the at least two quantities.

In a specific variation of the twenty-first aspect of the invention the at least two quantities comprise a bolus and a basal quantity. In a further variation the at least one of the at least two quantities is programmed as a delivery rate.

A twenty-second aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device is an implantable device and includes a memory for simultaneously storing a plurality of parameter values that are used for predefined time periods, one after the other, to control the treatment provided to the body or the monitoring of the body.

In a specific variation of the twenty-second aspect of the invention the medical device is an infusion pump and successive parameter values control delivery of a basal rate delivery for a successive, predefined periods of time. In a further variation the use of each parameter value is repeated in a cyclic manner, when no overriding commands are provided.

A twenty-third aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device is programmed to automatically deliver a predefined quantity of treatment to the body of the patient using a predefined variable rate delivery profile.

A twenty-fourth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device includes a reservoir for containing a drug and a pumping mechanism for transferring the drug from the reservoir to the body of the patient, wherein at least one of the medical device or the communication device has a memory for storing information related to the amount of drug dispensed with each unit of activation of the pumping mechanism and uses this information in calculating delivery amounts to program into the medical device.

In a specific variation of the twenty-fourth aspect of the invention the pumping mechanism includes a piston pump having a stroke volume wherein the unit of activation of the pumping mechanism is one stroke volume.

A twenty-fifth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device further includes a reservoir capable of holding a drug and a pumping mechanism, controlled by the MD processor, for transferring the drug from the reservoir to the body, wherein the medical device is controlled to change operational modes based at least in part on a detected or an estimated amount of drug remaining in the reservoir being at or below a predetermined level.

In a specific variation of the twenty-fifth aspect of the invention the change of operational modes causes the medical device to stop delivering medically significant quantities of the drug to the body. In a further variation the medical device continues to attempt to periodically deliver small but medically insignificant quantities of the drug after the change in operational modes.

In a specific variation of the twenty-fifth aspect of the invention after adding more drug to the reservoir to cause the amount therein to exceed the predetermined level, a user issued command is required to shift the operational mode of the medical device so that medically significant quantities of the drug may be delivered.

In a specific variation of the twenty-fifth aspect of the invention the medical device or the communication device is programmed to signal the patient of a low reservoir condition based at least in part on a detected or an estimated amount of drug remaining in the reservoir being at or below a prescribed level, wherein the prescribed level is greater than the predetermined level. In a further variation the prescribed level is defined such that an initial signal based on the prescribed level is provided to the patient at least one week before a drug level in the reservoir reaches the predetermined level.

A twenty-sixth aspect of the invention provides a medical system that includes (a) an electronically controlled ambulatory medical device (MD) including at least one MD telemetry system and at least one MD processor for controlling the MD telemetry system and for controlling operation of the medical device, wherein the medical device is configured to provide a treatment to a body of a patient or to monitor a selected state of the body; and (b) a communication device (CD) including at least one CD processor and at least one CD telemetry system, controlled by the CD processor, that sends messages to or receives messages from the medical device, wherein the medical device further includes a reservoir capable of holding a drug and a pumping mechanism, controlled by the MD processor, for transferring the drug from the reservoir to the body, wherein the medical device is configured to provide at least two signals of reservoir level, wherein a first signal indicates the amount of drug remaining in the reservoir is at or below a low level while a second signal indicates the amount of drug remaining in the reservoir is at or below a predetermined amount that is less than that remaining at the low level, wherein the first signal provides an indication that the reservoir should be refilled, and the second signal is used to limit pumping activity.

In a specific variation of the twenty-sixth aspect of the invention the pump is a piston pump and the first signal is generated at least in part by consideration of an amount dispensed per pump stroke and a number of pump strokes initiated.

A twenty-seventh aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device has the capability of reducing the treatment it supplies to the body to a medically insignificant level if the medical device and the communication device have not exchanged a selected type of message within a predefined time period or at a predefined time.

A twenty-eighth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device includes at least one counter that records the number of selected events that have occurred.

In a specific variation of the twenty-eighth aspect of the invention the at least one counter is a time counter. In a further variation the time counter counts minutes that have lapsed since initialization of the medical device.

In a specific variation of the twenty-eighth aspect of the invention the pump is a piston pump and at least one counter is a pump stroke counter. In a further variation either the pump stroke counter is reset after a drug reservoir within the medical device is refilled, or the pump stroke counter continues to increment with each pump stroke since the initialization of the medical device.

In a specific variation of the twenty-eighth aspect of the invention the at least one counter counts telemetry transmission time.

A twenty-ninth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device is configured to provide quantized amounts of treatment to or monitoring of the body of a patient, and wherein the medical device is configured with at least one treatment amount or monitoring amount accumulator that allows fractional portions of the quantized amounts to be periodically added into the accumulator.

In a specific variation of the twenty-ninth aspect of the invention the accumulator includes a treatment amount accumulator. In a further variation the medical device includes an infusion mechanism controlled by the MD processor, wherein the medical device is configured to provide a quantized amount of a drug to the body of a patient, and wherein the treatment amount accumulator is a dispensing amount accumulator. In a further variation the system is programed to allow the quantitized amount of a drug to be infused when an amount in the accumulator is equal to or exceeds the quantized amount and wherein the amount in the accumulator is decremented by the quantized amount based on each quantized amount infused.

A thirtieth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device is configured to inhibit at least two functions from occurring simultaneously.

In a specific variation of the thirtieth aspect of the invention either the configuration is set at least in part by software or the configuration is set by hardware.

In a specific variation of the thirtieth aspect of the invention, either one of the functions includes telemetry transmission, one of the functions includes telemetry reception, or one of the functions includes charging a circuit that is used to activate an infusion pump.

A thirty-first aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device monitors an MD voltage of an MD battery in the medical device and generates an MD voltage log.

In a specific variation of the thirty-first aspect of the invention the log includes a plurality of MD voltage values for each of a plurality of different current drain states.

A thirty-second aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein both the medical device and the communication device have memories for storing selected data about system operation, wherein at least a portion of the selected data is duplicated in the medical device and the communication device.

In a specific variation of the thirty-second aspect of the invention the medical device is programmed to periodically synchronize the duplicated data.

In a specific variation of the thirty-second aspect of the invention at least a portion of the selected data is synchronized automatically or is synchronized in response to a synchronization command.

A thirty-third aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein at least one of the medical device or the communication device is configured to allow selected alarm conditions to be cleared without removing the alarm condition, and wherein at least one type of alarm is reasserted after clearing if the alarm condition has not been eliminated within a predefined period of time.

A thirty-fourth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein at least one of the medical device or the communication device may be subjected to a plurality of alarm conditions, wherein alarms are prioritized for display in a predetermined order.

A thirty-fifth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device is programmed to allow a user to set a plurality of parameters to predefined default values using the communication device by issuing a command that does require specification of any of the default values.

A thirty-sixth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device is capable of being programmed to smooth out changes in treatment level when making a transition from a first treatment level to a second treatment level.

In a specific variation of the thirty-sixth aspect of the invention the first treatment level includes a first basal rate and the second treatment level includes a second basal rate. In a further variation a difference between the first and second rate is bridged by at least one step of predefined duration having a treatment level intermediate to the first and second levels. In a further variation the at least one step is at least three steps.

A thirty-seventh aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein at least one of the medical device or communication device includes an alarm that is activated in response to a selected alarm condition using a first set of alarm parameters, and wherein at least one of the alarm parameters is changed when the selected alarm condition is not cleared within a predetermined period of time.

In a specific variation of the thirty-seventh aspect of the invention the alarm parameters include at least one of a frequency, a volume, a duration, or a repetition pattern.

A thirty-eighth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device is capable of performing a test of battery voltage with a load on the battery.

In a specific variation of the thirty-eighth aspect of the invention the test of battery voltage is performed automatically and periodically. In a further variation, one of the following still further variations will occur, the battery voltage is also automatically and periodically checked with the battery under a minimal load, at least one selected electrical component is forced on to produce the load for testing, or the test is made to occur at least in part when at least one selected electrical component is powered on in the performance of its normal operation, wherein the electrical component provides a load for the testing.

A thirty-ninth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the MD processor uses a stack in conjunction with a central processing unit and wherein occurrence of a stack overflow causes the MD processor to be placed in a known state.

In a specific variation of the thirty-ninth aspect of the invention the known state is reached by resetting the processor.

In a specific variation of the thirty-ninth aspect of the invention the medical device includes memory having valid addresses that are accessible to a central processing unit within the MD processor, wherein the stack has predefined memory locations including a final memory location having a final memory address, and wherein a next memory address after the final memory address is an invalid memory address, and wherein a stack overflow directs the central processing unit to the invalid memory address which causes a non-maskable interrupt that in turn causes the MD processor to be placed in the known state.

A fortieth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein at least one MD watchdog circuit is capable of causing at least one MD processor to undergo a predefined process in the event that the watchdog circuit does not receive a first signal and a second signal, which is different from the first signal, within a predefined or programmable time period.

In a specific variation of the fortieth aspect of the invention the predefined process causes the MD processor to be reset. In a further variation one of the first or second signals is a signal generated by mainline software. In a further variation the other of the first or second signals is a signal generated by interrupt hardware.

A forty-first aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device monitors electrical activity of at least one electronic module or component located within the medical device and compares the electrical activity to at least one predetermined value.

In a specific variation of the forty-first aspect of the invention, further variations include at least one of the following, (1) the at least one electronic module is located within the MD processor, (2) the at least one electronic module includes a crystal oscillator circuit, (3) the at least one electronic module includes a driver for the treatment or monitoring device, (4) the predetermined value includes an upper and lower limit of a range of values, or (5) the electrical activity includes a current flow.

A forty-second aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device includes an infusion pump for selectively dispensing a drug, wherein the medical device includes a pressure transducer that provides an indication of pressure to the at least one MD processor and wherein the MD processor correlates the pressure readings from the transducer with the actuation of the pump.

In a specific variation of the forty-second aspect of the invention the correlation between pressure readings and pump actuation are compared to predefined parameters to determine the efficacy of the infusion pump for supplying a drug to a patient. In a further variation the pressure transducer is indicative of the pressure in a portion of the flow path between a pump mechanism and a restricted portion of the flow path.

Additional specific variations, provide the medical devices of each of the above aspects and above noted variations as implantable devices such as implantable infusion pumps, implantable physiological sensors, implantable stimulators, and the like, or external devices such subcutaneous delivery infusion pumps or sensors that ascertain a physiological parameter or parameters from subcutaneous tissue or from the skin of the patient. Such infusion pumps may dispense insulin, analgesics, neurological drugs, drugs for treating aids, drugs for treating chronic ailments or acute ailments. Sensors may be used to detect various physiological parameters such as hormone levels, insulin, pH, oxygen, other blood chemical constituent levels, and the like. The sensor may be of the electrochemical type, optical type, and may or may not be enzymatic in operation.

In even further variations of the above noted aspects, and above noted variations, one or more of the following is provided: (1) a first portion of the MD telemetry system is incorporated into the MD processor and a second portion of the MD telemetry system is external to the MD processor, (2) a first portion of the CD telemetry system is incorporated into the CD processor and a second portion of the CD telemetry system is external to the CD processor, (3) the MD processor includes an MD central processing unit and at least one other MD functional module, (4) the CD processor includes a CD central processing unit and at least one other CD functional module, (5) the MD electronic control circuitry includes at least one external MD functional module, other than a portion of the MD telemetry system, that is external to the MD processor, or (6) the CD electronic control circuitry includes at least one external CD functional module, other than a portion of the CD telemetry system, that is external to the CD processor.

Still additional aspects of the invention set forth method counterparts to the above system aspects as well as to other functional associations and relationships, and processes that have not been specifically set forth above but will be understood by those of skill in the art from a review of the teachings provided herein.

Further aspects of the invention will be understood by those of skill in the art upon reviewing the teachings herein. These other aspects of the invention may provide various combinations of the aspects presented above as well as provide other configurations, structures, functional relationships, and processes that have not been specifically set forth above.

BRIEF DESCRIPTION OF THE DRAWINGS

The above referred to objects and aspects of the present invention will be further understood from a review of the description to follow, the drawings, and the claims set forth hereafter, wherein:

DETAILED DESCRIPTION OF PREFERRED EMBODIMENTS

Figure 1A:
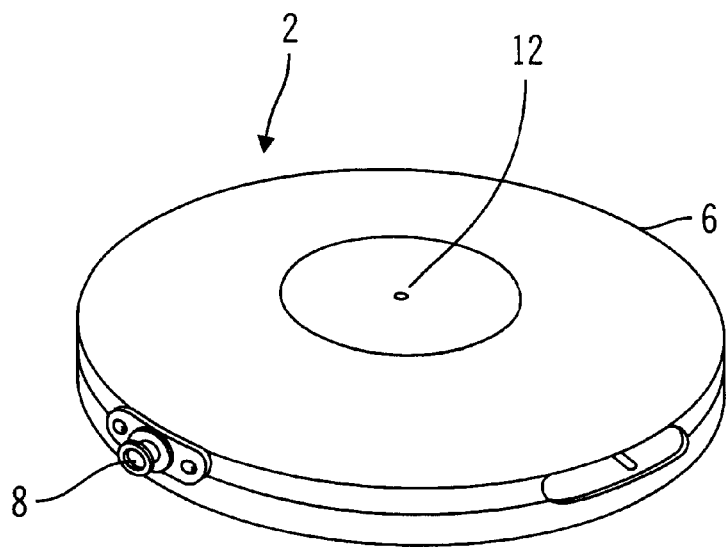
FIG. 1a depicts a perspective view of the main body of the implantable device of the first preferred embodiment.

Various details about the structural and functional configuration and operation of preferred ambulatory medical devices and preferred communication devices are found in several U.S. patent applications filed concurrently herewith and incorporated herein by reference in their entireties: (1) Ser. No. 09/768,045, (2) Ser. No. 09/768,035, (3) Ser. No. 09/768,042, (4) Ser. No. 09/768,198, and (5) Ser. No. 09/768,207.

U.S. patent application Ser. No. 09/768,045, filed on Jan. 22, 2001 (concurrently herewith), by Starkweather, et al., entitled "Ambulatory Medical Apparatus and Method Having Telemetry Modifiable Control Software", is hereby incorporated herein by this reference as if set forth in full herein. This application provides teachings concerning an implantable medical device (e.g. infusion pump) and hand-held communication device wherein the implantable device is capable of operating under control of different software programs, wherein a first program operates after resetting the implantable device and is not capable of allowing significant medical functionality but is capable of selected telemetry operations including telemetry operations that allow replacement software to be downloaded, and wherein a second program may be caused to take control of the device and enables medical functionality and selected telemetry operations but is incapable of receiving replacement software. It is also taught that a software image may be received in multiple messages where each message is provided with its own validation code and wherein a validation code for the whole image is provided and wherein each provided validation code must compared to a derived validation code prior to accepting the validity of the replacement software.

U.S. patent application Ser. No. 09/768,035, filed on Jan. 22, 2001 (concurrently herewith), by Lebel, et al., entitled "Ambulatory Medical Apparatus and Method Using a Robust Communication Protocol", is hereby incorporated herein by the references as if set forth in full herein. An implanted medical device (e.g. infusion pump) and external device communicate with one another via telemetry wherein messages are transmitted under a robust communication protocol. The communication protocol gives enhanced assurance concerning the integrity of messages that impact medical operations of the implantable device. Messages are transmitted using a multipart format that includes a preamble, a frame sync, a telemetry ID, data, and a validation code. The data portion of the message includes an op-code that dictates various other elements that form part of the message. The data portion may also include additional elements such as sequence numbers, bolus numbers, and duplicate data elements. A telemetry ID for the transmitting device may be implicitly embedded in the message as part of the validation code that is sent with the message and that must be pre-known by the receiver to confirm the integrity of the received message.

U.S. patent application Ser. No. 09/768,042, filed on Jan. 22, 2001 (concurrently herewith), by Bowman, et al., entitled "Ambulatory Medical Apparatus and Method using a Telemetry System with Predefined Reception Listening Periods", is hereby incorporated herein by the reference as if set forth in full herein. This application provides teachings concerning an implantable medical device (e.g. infusion pump) and an external device that communicate with one another via telemetry messages that are receivable only during listening windows. Each listening window is open for a prescribed listening period and is spaced from other listening windows by an interval. The listening period is typically kept small to minimize power consumption. To increase likelihood of successful communication, the window may be forced to an open state, by use of an attention signal, in anticipation of an incoming message. To further minimize power consumption, it is desirable to minimize use of extended attention signals, and this is accomplished by the transmitter maintaining an estimate of prescribed listening start times and attempting to send messages only during listening periods. In the communication device, the estimate is updated as a result of information obtained with the reception of each message from the medical device.

U.S. patent application Ser. No. 09/768,198, filed on Jan. 22, 2001 (concurrently herewith), by Lebel, et al., entitled "Ambulatory Medical Apparatus with Hand Held Communication Device", is hereby incorporated herein by this reference as if set forth in full herein. This application provides teachings concerning an implantable medical device (e.g. infusion pump) and handheld communication device (CD) that exchange messages via telemetry such that commands are supplied to the implantable device and operational information is obtained therefrom. The CD is controlled, at least in part, by a processor IC according to a software program operating therein and provides feedback to a user via a visual display, an audio alarm, and a vibrational alarm, and allows input from the user via a touch sensitive keypad. Certain input functions are restricted by password. The visual display includes an icon and fixed element display region and a bitmap display region. The fixed element display region includes time and date displays, battery and drug level displays that decrement, and a moving delivery state display. Various screens allow operational or log information to be displayed and/or user entry of commands. Program features when disable are removed from a series of screen options that can be scrolled through.

U.S. patent application Ser. No. 09/768,207, filed on Jan. 22, 2001 (concurrently herewith), by Starkweather, et al., entitled "Method and Apparatus for Communicating Between an Ambulatory Medical Device and Control Device Via Telemetry Using Randomized Data", is hereby incorporated herein by this reference as if set forth in full herein. This application provides teachings concerning an implantable medical device (e.g. infusion pump) and handheld communication device that communicate with one another via telemetry wherein transmitted messages have enhanced numbers of and/or regularity of bit transitions to minimize the risk of synchronization loss between transmitted bits of data and received bits of data. It is taught that bit transitions for portions of messages may be enhanced by applying a pseudo-randomization scheme to those portions of messages that are transmitted in a way that allows the receiver to extract the original data from the received randomized data. Preferred randomization techniques modify (i.e. randomize) the data using a CRC value that is being accumulated while simultaneously causing the modified data to modify subsequent accumulation of the CRC itself. Upon reception, the reversal of data randomization is then made to occur so that the intended message is appropriately received.

The first embodiment of the present invention provides a long term implantable medical delivery system that controllably supplies insulin to the body of a patient afflicted with diabetes mellitus. This embodiment includes an implantable medical device and an external communication device. In the most preferred embodiments, the communication device is a hand held device that is used directly by the patient to interact with the medical device as opposed to being limited to use by a physician, nurse, or technician. It is preferred that the communication device provide (1) the ability to send commands to the medical device, (2) receive information from the medical device, and (3) be able to present to the patient at least a portion of the information it receives from the medical device. In preferred embodiments, the patient interacts with the medical device via the communication device at least once per week, on average, more preferably at least once every other day, on average, and most preferably at least once per day, on average.

The implantable medical device (MD) includes a biocompatible housing; a reservoir within the housing for holding a quantity of insulin; a side port that attaches to the side of the housing, a catheter, that connects to the side port; a pumping mechanism, within the housing for moving the insulin from the reservoir through the sideport and through the catheter to the body of the patient; and control, monitoring, and communication electronics located within the housing. In alternative embodiments various portions of implantable medical device hardware may be located outside the housing. For example, the pumping mechanism or a telemetry antenna may be located within the sideport or other side mounted housing; or a telemetry antenna may mounted on the outside surface of the housing, or extend along the catheter.

The external communication device (CD) communicates commands to the medical device, receives information from the medical device, and communicates system status and system history to the patient. The external communication device includes a housing; a keypad mounted on the housing; a display forming part of the housing; and control, monitoring, and communication electronics located within the housing. In alternative embodiments, the keypad may be replaced in whole or in part by a touch sensitive display or a voice recognition system. In addition, or alternatively, the display may be replaced in whole or in part by a speech generation system or other audio communication system.

Figure 1B:
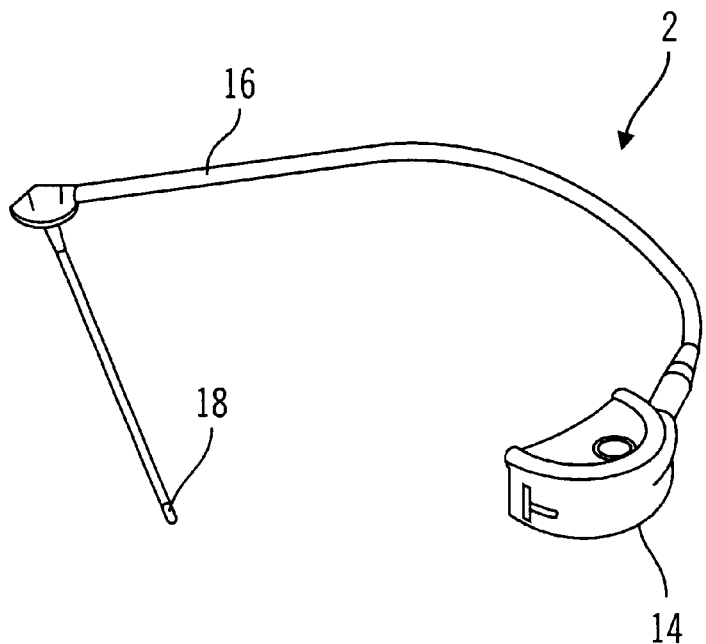
FIG. 1b depicts a perspective view of the support and catheter assembly that attaches to the main body of the implantable device of the first preferred embodiment.

The outer appearance of the implantable device 2 is depicted in two pieces in FIGS. 1a and 1b and includes housing 6 having a drug outlet port 8, and a refill port 12, a removable sideport 14 that mounts against the side of the housing 6 over outlet port 8, and a catheter 16 having a distal end 18 and a proximal end that attaches to sideport 14. In alternative embodiments, the implantable device may take on a different shape and/or the sideport may be removed in favor of a permanently mounted catheter assembly.

Figure 2:
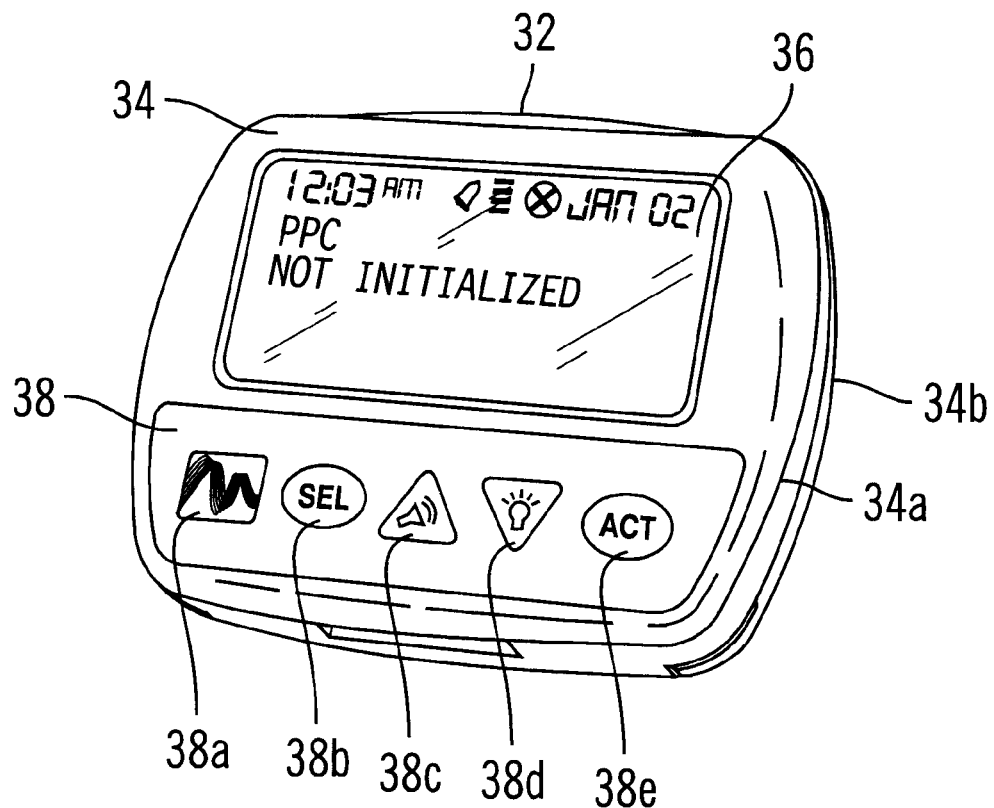
FIG. 2 depicts a perspective view of the external communication device of the first preferred embodiment.

The outer appearance of the external communication device 32 is depicted in FIG. 2. The various components of the external communication device are fitted in or on housing 34. Housing 34 is divided into a front portion 34a and a back portion 34b. The front portion 34a is provided with an opening in which an LCD panel 36 is positioned. The panel 36 has a lower portion that is a bit map display and an upper portion that provides icons and fixed element displays. The front portion 34a of the external communication device is also provided with a five-element keypad 38. A first key 38a is not located under a raised pad and does not provide tactile feedback when it is touched and may be used for special functions. The remaining four keys 38b, 38c, 38d, and 38e have raised pads that provide tactile feedback when they are depressed. These remaining keys may be used in normal device operation and are known as the select key, the up arrow key, down arrow key, and the activate key, respectively. The back portion 34b of the housing is fitted with a door under which a compartment is located for holding a replaceable battery. The external communication device (CD) is a hand-held device that allows a user to program and communicate with the implantable device. The external communication device of the present embodiment preferably has a weight of less than about ounces, a thickness of less than about 0.8 inches, a width of less than about 2.8 inches, and a length of less than about 4.0 inches.

The implantable device includes a memory for storing program code and data. A portion of the memory in the implantable device is preferably used to store configuration information for the external communication device and for the implantable device itself. This allows the configuration data to be reloaded into a replacement external communication device if the original should be lost or damaged. This memory is also used to store system operation information in the form of activity logs and counters, such an insulin delivery log. Various portions of the contents of implantable device memory are downloaded to the external communication device periodically. The downloads to the external communication device may occur manually, automatically, or semi-automatically.

The implantable device control electronics include various self-checking mechanisms to ensure that reliable operation of the system occurs. For example, as the pumping mechanism in this first embodiment requires a firing voltage that is significantly greater than the supply voltage, a pre-fire voltage on the pump firing circuit is checked to ensure it is large enough to cause the pump to execute a full stroke. After firing, the voltage is checked again, to ensure that discharging of the circuit occurred. Each processor is monitored by a watchdog circuit that must be serviced, periodically. As implemented in the software, servicing must occur at both the interrupt level and at the mainline code level to ensure that the processor has not malfunctioned at either level. Insulin delivery calculations are performed by both processors in such a manner that both processors must agree on the quantity and timing of insulin delivery. If an error of a significant nature is found in the system, the implantable device may be placed in a protective mode (i.e. suspend mode or stop mode) where insulin delivery is cut back to a medically insignificant rate (e.g. about 1 pump stroke per hour) or stopped completely. It is preferred to have a small amount of insulin be delivered periodically to help prevent the occurrence of catheter blockage. In any event, if system failure does occur the system effectively stops delivery and attempts to warn the patient.

As the implantable device is controlled by messages that it receives from the external communication device, messages sent to the implantable device have their accuracy and appropriateness checked with varying degrees of scrutiny depending on the critically of the message.

First, for example, all most all messages are sent from a particular external communication device to a particular implantable device using explicit identification information of the receiver to identify itself as the intended recipient. It is considered desirable to use identification information with messages that relate to medical treatment (e.g. the changing of insulin infusion rates). More particularly it is desirable to use identification information with messages that relate to changing medical treatment in a way that could have acute ramifications (e.g. to over supplying a drug such as insulin as opposed to under supplying the drug).

Second, the identity of the sender is preferably embedded implicitly in the message. This implicit embedding occurs by using the identification information of the sender in calculating a cyclical redundancy code (CRC) that is sent with the message. As such, the implantable device must know the identity of the sender in order to successfully check the content of the message against the transmitted CRC.

Third, the values of the data in the message are compared to an operation code (Op Code) sent with the message to ensure that the code and data are compatible. This Op Code is also used to set the size of the most messages, thereby providing a mechanism to increase electrical efficiency of the system by providing a way to limit reception time to only that amount necessary to receive a particular message.

Fourth, if the message pertains to drug delivery, the message is sent with redundant data that must match for the message to be interpreted as valid. If for any reason the message is interpreted as invalid, the message is ignored.

To avoid problems associated with long transmissions that may otherwise contain long strings of non-transitioning data (i.e. long strings of 1 s or 0 s), the data portion of most messages are randomized prior to transmission and de-randomized upon receipt. For energy savings and time savings, randomization and de-randomization preferably occur in a single pass through the data and preferably utilize the semi-random attributes of the CRC tables from which CRC codes are built.

In the event that an error or other significant event occurs in the implantable device, the device may attempt to inform the patient of the event by sending a telemetry message to the external communication device or alternatively by activating an audio alarm mechanism within the implantable device itself.

The implantable device is preferably configured so that the software running in it can be replaced or upgraded if the need should arise. The software may be downloaded into the implantable device through telemetry. The implantable device may be operated under two types of software: (1) bootloader code, or (2) application code. The bootloader code may be broken down into first stage boot loader code which is stored in the ROM that is internal to the ASIC and second stage bootloader code that is stored in a SEEPROM or other non-volatile memory associated with each ASIC. The bootloader code and application code are different for each ASIC.

The bootloader code does not care about the application in which the implantable device may be used. The bootloader code is not concerned with whether, the implantable device is an infusion device, a sensor, a stimulator, or the like, or a combination thereof. On the other hand, the application code is concerned with the medical functionality of the device and thus is designed specifically for a given type of application. As such, if an implantable device includes a pump and was initially configured (i.e. loaded with specific application software) to work with one drug (e.g. insulin) in one manner (e.g. allowing different preprogrammed basal rate changes to occur at the beginning of each half hour of the day and allowing simultaneous use of an immediate bolus and an extended bolus), it could be reconfigured to operate in a completely different manner while using the same drug or a different drug by simply changing its application code. The replacement of application code in this context is different from a mere change in program variables that may allow various control limits to be changed or even to allow the code to execute different algorithms that are preexistent within the code. The replacement of application code in this context involves the replacement of at least portions of the code that set forth program algorithms.

When operating under control of the bootloader code, the implantable device allows certain telemetry operations to occur and also allows downloading of new application code, but does not allow any drug delivery. The application code when controlling the system, on the other hand, knows how to handle drug delivery but is not capable of downloading new code, or otherwise modifying itself (other than to accept changes in parameter values). The bootloader code is also designed and operated in such a way that new bootloader code can be downloaded to the SEEPROM if an upgrade is felt to be appropriate.

In alternative embodiments, it is possible to merge the functionality of the second stage bootloader code and the application code into a single piece of code that can be upgraded as desired. In still further embodiments, it may be possible only to upgrade the application code and not the second stage bootloader code.

As noted above, the implantable device assembly includes a detachable catheter and sideport that provides a pathway for the insulin to a desired infusion location in the patient's body (e.g. into the patient's peritoneal cavity). The sideport allows for non-surgical diagnosis of a catheter blockage by using pressure. The sideport allows introduction of a refill needle and small syringe to clear an obstructed catheter (e.g. using up to 110 psi of pressure). The sideport also allows the introduction of a refill needle and a pipet to verify pump stroking. The catheter includes a check valve that seals (e.g. at between 0.5 to 3 psid) and provides a redundant valve outside the pump to prevent medication or body fluids from back flowing into the implantable device reservoir. The sideport in conjunction with the check valve facilitates rinsing the fluid path within the implanted device with sodium hydroxide, or other functionally similar material, by allowing effluent to be drawn out the sideport rather than pumped out the catheter tip. In alternative embodiments, a sideport may not be used.

As noted above, the external communication device has both an audio alarm and a vibrator for alerting the patient or user of warnings and alarm conditions. The user has some control over the selection of audio alarm or vibration while the system can automatically switch from vibration to audio if the vibrational alarm is not responded to in a timely manner. The audio alarm is programmable to emit at different frequencies, at different volume levels, for different durations, and with different repetition patterns. These various alternatives are used to signal different conditions. The vibratory alarm is also programmable to go off for different durations and with differing repetition patterns. In alternative embodiments, only one type of alarm may be used and it may be used with or without different frequencies, volumes, durations, or loudnesses.

The software controlling the external communication device is permanently stored within the external communication device using a non-volatile memory such as a serial electrically erasable programmable read only memory (SEEPROM) and is transferred to random access memory (RAM) for execution. The code being executed in RAM can be reloaded from that SEEPROM as needed. Software located within the SEEPROM can be replaced with new software under controlled conditions. The external communication device is provided with sufficient memory capability to store a duplicate, or upgrade, version of application software for the implantable device as well as to store about 120 days of operational data. Under controlled conditions the external communication device may be reset to its default configuration automatically (i.e. upon command without the user having to specifically identify specific parameter values). In alternative embodiments the software may be stored in a different device (e.g. a physical ROM, volatile RAM, non-volatile RAM, or in a replaceable plug in module). The software may be divided into bootloader and application code portions.

As noted above, the implantable device and external communication device communicate with each other through radio frequency telemetry where reception and transmission within the implantable device uses an antenna that is located within the metallic device housing based on a carrier frequency that allows an acceptable amount of signal to penetrate through the housing and through the human body. In alternative embodiments, an antenna for the implantable device may be placed on the housing or be otherwise located external to the housing so that outgoing and/or incoming signals need not penetrate the housing material. For the present embodiment the preferred frequency is either about 131 kHz or about 262 kHz. The preferred data transfer rate is at about 8200 bits/second. In alternative embodiments, different carrier frequencies may be used, e.g. from tens of kilohertz to thousands of megahertz. Also in alternative embodiments other data transfer rates may be used. The external communication device and implantable device are configured and operate together to provide rapid feedback to the operator. For example, a response to a basal rate or bolus programming telemetry interaction is preferably provided to the patient within no more than 20 seconds and more preferably within less than about 10 seconds, and most preferably within less than about 5 seconds.

Each implantable device and external communication device are preferably assigned unique telemetry identifiers and a particular implantable device and particular external communication device are made to undergo a linking process (alternatively known as a marrying process) so substantive communication (e.g. communications that allow the external communication device to control the medical operation of the implantable device) is limited to a joined pair. The communication link between the external communication device and implantable device provides various levels of checking and confirmation to minimize the possibility of the implantable device receiving and then acting on an erroneous delivery command message. In alternative embodiments unique identifiers may be supplied to only one of the implantable or external communication devices, or even non-unique identifiers may be utilized.

The linking or marrying process is completed prior to a external communication device being allowed to send drug delivery commands or updated software to a particular implantable device. In this embodiment, each time an external communication device is replaced or reset, the marrying process must be repeated. The marrying feature provides the mechanism to configure an implantable device to communicate with a particular external communication device. This is carried out when the implantable device and the external communication device are initially configured. The linking process requires positive assertion from the user indicating that external communication device is linking to the correct implantable device. The linking process starts with the external communication device sending an interrogate message to all implantable devices within range by using a universal identifier. Each implantable device that is within range responds to the external communication device's interrogate message by sending a response that includes patient identity information as stored in that particular implantable device. If the desired implantable device is the first to respond to the interrogate signal, the user can acknowledge his/her desire to link the external communication device and the implantable device. Otherwise, if the first responding implantable device is not the one to be linked to, the patient may indicate so and that particular implantable device identifier is added to a temporary exclusion list and the interrogate message is resent (including the exclusion list). When the interrogate message is received by each implantable device, only those whose identifiers are not in the exclusion list will attempt a response, thereby allowing other implantable devices within range to respond and be heard. Once the correct implantable device is the one that has its response displayed by the external communication device, the user can elect to start the linking process. Once the link is established, the implantable device is made to enter suspend mode and then the user must reprogram all basal rates including temporary basal rates that were in progress, profile basal rates, and delivery patterns. In alternative embodiments, all or a portion of this information may be retrieved from the implantable device, assuming it was programmed previously, but in this particular embodiment as an added measure of safety, it was preferred that these parameters should be reprogrammed so that the user is made to provide a positive assertion that he/she knows the delivery parameters that the implantable device is using. During the linking process the external communication device obtains other data from the implantable device that it requires in performing its operations, e.g. the external communication device obtains stroke volume information for the pulsatile pump and obtains insulin concentration data that is stored in the implantable device.

The sending and receiving of IR signals by the external communication device is based on basic IrDA standards. In the present embodiment, the transfer rate for the IR link is about 115 kbits/second. Of course in other embodiments other baud rates may be used or even automatically selected between. The IR link may be used to (1) upload new software to the external communication device from a second external device, (2) download system operation information to the second external device for further analysis as desired, and/or (3) pass commands/responses to or from a second external device from or to the implantable device. The second external device may be personal computer running appropriate software or a more specialized system. The communications sent over the IR link are based on protocol details that ensure that only intended messages, and correctly received messages, are received and acted upon.

In an alternative embodiment a second or third external communication device may be used in conjunction with the first external communication device or as a temporary or partial replacement therefor. For example, at night, a chest strap, wrist watch, mattress pad, or the like containing appropriate telecommunication capabilities might be used as a relay device to pick up warning signals or other communication signals coming from the implantable device and then to transmit them to the first external communication device or a third external communication device so that a warning may be sounded to wake up the patient, to directly notify emergency personnel of a problem, or to notify other monitoring personnel in a timely manner of medical device operation or patient condition. Such notification may occur using any appropriate telecommunication systems, such as telephonic or internet connections. In the case of directly warning the patient, if the second communication device has sufficient power and functionality it may implement the warning signal directly. The second or third external communication devices may communicate with the first external communication device via RF telemetry, IR communication link, optical link, galvanic connection, inductive communication, or the like.

The implantable device of the present embodiment has various delivery modes. One of these modes is the suspend mode wherein the system is caused to reduce insulin delivery to a clinically insignificant amount (e.g. 1 pump stroke (approximately 0.2 units of insulin assuming a stroke volume of 0.5 microliters and a U-400 insulin concentration) per hour. It is intended that this minimal rate of delivery keep the catheter open. The "suspend mode" mode may be used to interrupt delivery of a bolus, priming bolus, profile basal rate, diagnostic rate, and/or temporary basal rate. The system is programmed to alarm periodically to indicate to the user that the system is delivering insulin at a clinically insignificant rate. The user may exit suspend mode and resume basal delivery. In this embodiment, any bolus that is in progress when suspend mode is asserted is canceled such that any undelivered portion will not be delivered even when suspend mode is cleared. Other than when entering suspend mode through the linking process, if the implantable device is delivering a temporary basal rate when suspend mode is entered, the temporary basal rate duration continues while the pump is in suspend mode, and the temporary basal rate is reasserted when suspend mode is cleared for any portion of the duration that has not already lapsed. Of course in other embodiments other control options may be implemented with regard to going into or coming out of a mode analogous to suspend mode.

The external communication device is programmable using an audio bolus mode. This mode allows a user to program the delivery of a bolus without looking at the external communication device display. This mode provides an audio feedback to the user to indicate the amount of the bolus that is being programmed. The audio bolus feature allows programming of immediate boluses. Immediate boluses are those that specify a quantity of insulin to be delivered in as short a time as possible, e.g. a short as time as necessitated and allowed by any required repeated operation of the pumping mechanism. Under selected conditions a parameter selection may be made that dictates the incremental increase in bolus amount with each successive key entry (e.g. press of the up-arrow key) when in audio bolus mode. Under selected conditions, the external communication device provides another parameter that enables or disables the audio bolus feature. In the present embodiment, once the desired bolus amount has been achieved by the repeated pressing of the select key, the user may confirm the accuracy of the selected amount by pressing a different key (e.g. the ACT key). When this confirmation key is pressed for the first time the external communication device plays a sequence of audio tones so as to indicate the amount programmed. If the amount is correct the user may press the ACT key again to initiate delivery. If the amount is incorrect the user may simply wait a predetermined, but short, period of time for the external communication device to time out or alternatively, the user may press any key other than the confirmation key. A distinct sound is emitted to indicate that delivery was not initiated, at which point the user may simply start over with the audio or visual programming.

Of course in other embodiments, other key press sequences may be used in the performance of programming an audio bolus. Alternatively, if the system were configured with a microphone or other sound transducer and appropriate audio command recognition software or hardware, audio programming could be performed without any keystrokes or with a single keystroke to activate the external communication device's listening mode. In a similar vane, if the external communication device were configured with a sound transducer and appropriate speech enabling hardware and/or software, then instead of sounding a series of beeps to indicate program status, it could communicate to the user, in a predefined language, to indicate the status. In still further alternatives, speech recognition and/or speech generation hardware could be used to replace or supplement keypad or touch screen input capabilities.

In the present embodiment, basal rate delivery and bolus delivery may be programmed to occur in conjunction with each other as opposed to one replacing the other. The system does not replace basal rate delivery with bolus deliver but instead combines the amount to be delivered under basal programming with the amount to be delivered under bolus programming to cause a net amount to be delivered that is equal to the sum of both amounts. The user may program a bolus amount on the external communication device and the implantable device will respond by delivering that amount. The amount of the bolus is subjected to a bolus maximum as described below.

The system allows the user to program an amount to deliver that the implantable device will deliver as quickly as possible using a required number of pump strokes with typically no more than 6 seconds between successive pump strokes (e.g. 1–3 seconds per stroke). This type of bolus is sometimes referred to as an immediate bolus or phase I bolus.

The system allows a bolus to be delivered where the user programs an amount and a duration. The implantable device delivers the amount as a rate (i.e. number of pump strokes per unit time) for the duration specified such that the amount programmed by the user is delivered within the duration. This is analogous to a basal rate or temporary basal rate delivery in some manner but is not identical as the total amount to be delivered is the sum of this amount and any basal rate that is currently in effect. Furthermore, in this delivery mode the user does not program the delivery amount as a rate. This type of bolus is sometimes referred to a square wave or phase II bolus.

The system supports a "dual wave bolus" where the user programs an amount for immediate delivery (immediate bolus) and a second amount for delivery during a specified duration (square wave bolus). When programmed in this manner the implantable device delivers the immediate amount as described above, followed by delivery of the second amount over the duration as a square wave amount also as described above.

The system also supports delivery of an immediate bolus while delivery of a square wave bolus is in progress or while delivery of the square wave portion of the dual wave bolus is in progress so long as the immediate portion of the dual wave bolus has been completed.

The programming of boluses in the external communication device is further controlled by a variable bolus option. If the variable bolus option is set to "no", only immediate bolus programming is allowed and the square wave and dual bolus options are removed from the menu choices available on the external communication device. If the variable bolus option is set to "yes", immediate, square wave, and dual wave bolus programming are allowed and all menu options are presented to the user.

The implantable device holds a number of logs. One of these logs is a bolus history log. In this log the implantable device maintains the time and amount of boluses that have been delivered. This log contains the most recent boluses that were delivered. This log is set to contain up to a predefined number of boluses after which the log wraps around and deletes older entries in favor of recording new entries. The external communication device receives these records from the implantable device. These records may be viewed on the external communication device or alternatively they may be downloaded to a second external device where they can be viewed in numerical form or be plotted for viewing in graphical form. The storage of this log information in the implantable device ensures that historical information remains available even in the event that the external communication device is lost, damaged, or otherwise fails. Each time a new bolus is programmed from the external communication device and confirmed by the implantable device, the details of the previously delivered bolus are provided back to the external communication device so a log maintained in the external communication device is almost as up to date as the log maintained by the implantable device. The log maintained in the external communication device can be scrolled through for review by the patient or healthcare provider. Each bolus history record includes the amount, time, and date of the bolus delivery.

The implantable device maintains another log that provides the total amount of insulin delivered by date. The implantable device maintains a history of the most recent 120 days of insulin delivery totals with the daily total separated by basal delivery and bolus delivery. The daily totals are downloaded automatically or semi-automatically from the implantable device to the external communication device each day. As with the bolus log, this information is protected from loss or failure of the external communication device by its retention in the implantable device.

The system maintains multiple sets of basal rates where each set dictates basal rate delivery for a selected interval of time and each element in each set dictates the basal rate delivery for a subset of that selected interval of time. In the present embodiment the number of sets is three, the selected interval of time is 24 hours beginning at midnight, and the subset of the selected interval of time is 30 minutes which starts at the beginning of each half hour mark during the day. As such, each set consists of up to 48 rates that can start on any half-hour of the day.

For programming convenience, the delivery rates need not be entered for each subset but instead only for those subsets that represent a change in delivery rate compared to the previous subset. As such, in this embodiment, basal rate values are only entered for the subset half hours in which transitions occur and are entered by specifying the start times and rates. Up to three 24-hour profiles may be entered with only one of the profiles selected as active at any given time. When a profile is made active, information about that profile is communicated to the implantable device to replace any other basal rate information retained there. As an added safety feature, only one profile set is stored in the implantable device at any given time. The active profile is repeatedly used day after day to control basal rate delivery in the implantable device until it is replaced by a different or revised profile. Such basal profile sets may be used for different types of days, e.g. work days, non-work days, exercise days, non-exercise days, sick days, high stress days, and the like.

The system allows a temporary basal rate to replace any profile based basal rates during a specified period. This feature allows the user to program a basal rate without changing the basal profile. When the temporary basal rate duration lapses, the implantable device resumes delivery of the basal profile rate that is then in effect based on the selected profile and the then current time of day. The temporary basal rate, for example, may be utilized to program lower basal rates during periods of exercise, or used to program higher rates during periods of high stress.

Selected "personal events" are recordable by the user in a personal event log. The personal event log is accessed through the external communication device and stored in the external communication device. In alternative embodiments these events may be communicated to the implantable device for safekeeping. The user may record the time that certain events occurred, such as exercising, meals, or illness. A parameter may be set so as to disable personal event logging. When disabled, the option does not present itself on the user menu in the external communication device. In the present embodiment, the system provides sufficient memory and control for retention and review of up to 100 such events.

"Automatic Off" is another feature of this embodiment. When this feature is enabled the insulin delivery system turns itself off if the user does not interact with the implantable device through telemetry for a programmed amount of time. This feature may be enabled or disabled. In this context, the turning off of the implantable device refers to the implantable device going into suspend mode. The implantable device alarms if it goes into minimum delivery mode as a result of the automatic off interval lapsing. The automatic off interval is reset each time the implantable device receives a valid telemetry message from the external communication device intended specifically for it. In order to save battery power in the implantable device, the external communication device is programmed to track the time that elapses between communications and to alarm 5 minutes before the automatic off interval lapses. This enables the user to clear the alarm and interact with the implantable device before the implantable device itself alarms and thus results in reduced power consumption by the implantable device.

An additional parameter of the present embodiment is bolus maximum which specifies the size of the largest single bolus that can be delivered. A pumping operation used in setting up the implantable device, called priming bolus is not subject to this maximum. The external communication device is programmed so that a user can not program an immediate bolus amount greater than the bolus maximum. The external communication device is also programmed so that the sum of the immediate amount and the extended amount of a bolus (regardless of the duration) may not exceed the Bolus Maximum. The implantable device uses the bolus maximum as a safety check of each bolus request that is received from the external communication device.

The external communication device is programmed to sound a maximum alarm if the user attempts to deliver an amount of insulin during a predefined period that exceeds a predefined limit. In this embodiment the predefined period of time is one hour and the maximum alarm is termed the hourly maximum alarm and the predefined limit is 2.5 times the Bolus Maximum. This alarm is intended as a safety alert to the user and not as an absolute limit on the amount that can be dispensed in any one hour period. The external communication device is programmed to compute the total amount of bolus delivery during the previous one hour period each time a bolus is programmed. If the amount already delivered summed with the programmed amount exceeds 2.5 times the programmed bolus maximum, the external communication device alarms and the bolus is not allowed. When an hourly maximum alarm is cleared, there is a short window where the user may program a bolus that normally would trigger an hourly maximum exceeded alarm. Following the short window, bolus programming is subject to the hourly maximum limitation and warning again. In the present embodiment the short window is set at ten minutes. In the present embodiment both amounts programmed for an immediate and square wave boluses are considered in triggering the hourly maximum exceeded alarm regardless of when the extended bolus amount was or is to be delivered. In alternative embodiments, the external communication device may be programmed to take into account quantities that have or will be delivered within a one hour period based on the programmed amounts and time intervals. In other embodiments the maximum amount in the predefined period may be determined based on something other than the maximum bolus amount. In still further embodiments the maximum bolus amount may be implemented as a hard limit. In still further embodiments, a second or subsequent bolus programmed in the same short window would not be subject to the warning. In other embodiments, the external communication device could not only warn the patient that the maximum amount has been exceeded but would also indicate the amount that was delivered in the period being considered.

External communication device programming and implantable device delivery are also limited by a basal rate maximum which is the highest rate that may be delivered using a profile basal rate or a temporary basal rate. A delivery rate used for diagnostic purposes known as the diagnostic rate is not subject to this maximum. The external communication device is programmed to inhibit the user from entering a basal rate greater than the basal rate maximum. The implantable device uses the basal rate maximum as a safety check of each basal rate that is programmed. The implantable device ignores delivery requests that include basal rate amounts greater than the basal rate maximum. The external communication device is configured to inhibit the user and physician from setting a maximum basal rate that is less than any of the basal rates already programmed including those in the profiles that are not currently active.

The external communication device is capable of displaying an estimate of the amount of medication remaining in the insulin reservoir. The external communication device is programmed to alarm when the medication remaining becomes less than a predefined low-reservoir threshold. As with other alarm conditions in the system, low-reservoir threshold alarms are reasserted after clearing if appropriate actions have not been taken to resolve the condition that gave rise to the error or event (e.g. refilling of the reservoir has not been completed). Once the low-reservoir alarm is cleared, and a predetermined period of time has lapsed and the system determines that the reservoir has not yet been refilled, the alarm will be reasserted so as to provide the user with a reminder to have the reservoir refilled.

The implantable device and external communication device retain clinical history information as records of various events that the system tracks. For example, events that stop the delivery of insulin such as alarms are recorded in the clinical history. User-initiated events such as suspend mode that stop the delivery of insulin are also recorded. Refills are also recorded. The system also contains logs for system diagnostics such as implantable device battery levels. Through menu options the user may view these various history logs.

In this embodiment, the system is programmed to allow a user to initiate a self test in both the external communication device and the implantable device. If there are any error conditions detected, they are reported to the user. The system self test includes a number of different checks: (1) implantable device memory, (2) external communication device memory, (3) implantable device piezo operation, (4) external communication device piezo operation, (5) external communication device vibrator operation, and (6) external communication device display. If an error is detected, the system reports the error to the user using visual, vibrational or audio alarms.

The external communication device is configured to emit audio alarms, or to vibrate, in the event an alarm condition exists. The implantable device always emits an audio alarm if an error condition persists beyond a predefined amount of time based on the particular alarm condition that exists. The external communication device is configured to allow the user to selected audio or vibration notification when alarm conditions exist. For many alarm conditions, the implantable device is programmed to contact the external communication device by telemetry prior to sounding an alarm on its own. In the event that the external communication device receives the message and successfully notifies the user of the condition and the user clears the alarm prior to a predefined time period passing, the implantable device does not sound the alarm directly on its own. In the event that the alarm condition is cleared but not resolved, the implantable device may directly reassert and sound the alarm later or may reassert and recontact the external communication device through telemetry.

The system supports an audio feedback mode where the implantable device may be programmed to beep on a first predefined number (e.g. 3–10 pump strokes after a rate change, and for a first predefined number (e.g. 3–10) pump strokes of a bolus. In other alternative embodiments, other feedback techniques may be implemented.

The system supports a storage mode for the implantable device and for the external communication device. Storage mode in the implantable device is a state where there is no drug delivery and no alarms and the frequency of waking up to listen for incoming telemetry messages is reduced. Storage mode in the external communication device is a state where the screen is blank and no user functions are available. The implantable device is programmed to enter storage mode upon receipt of a particular telemetry command. The implantable device is programmed to exit storage mode by receipt of a particular telemetry command. There is no implantable device alarm that indicates that the implantable device is entering storage mode.

The external communication device is programmed to enter storage mode if there is no user interaction with the external communication device for an extended period of time (e.g. 5–10 days). The external communication device is programmed to exit storage mode in the event of user interaction with external communication device such as button presses. When the external communication device is in storage mode the screen is blank and the external communication device hardware is put into a low-power state.

The system allows refilling of the pump and reporting on delivery accuracy. The system is programmed to allow entry of an extracted volume and a fill volume during the refill process. The external communication device may be made to display delivery accuracy based on a difference between the expected amount remaining in the insulin reservoir and the actual amount of insulin removed during the refill process.

In the present embodiment, the system is configured to support user and physician programming of the delivery options using insulin units based on a desired resolution value not based on a predetermined pump stroke volume. When the external communication device is programmed to deliver a certain amount of insulin, the external communication device calculates the number of pump strokes necessary to deliver that quantity and passes the pump stroke information onto the implantable device. The pump stroke information is passed in fixed point format including both an integer portion and a fractional portion. The determination of pump strokes is based on the implantable device pump stroke volume and the insulin concentration.

The system of this embodiment is configured to allow a programming option to be set that allows the physician to prime the catheter quickly. As will be discussed further hereafter, this option is only available as a supervisor function. The priming function/option triggers the implantable device to deliver an amount of insulin large enough to fill the catheter. In this mode, pump strokes are delivered as fast as possible. The physician is notified when the priming bolus is completed.

The system supports a special rate called diagnostic rate that is only programmable as a "supervisor only" function. This special rate is used in determining delivery accuracy. The diagnostic rate function triggers the implantable device to deliver at a programmed rate that is not subject to the basal rate maximum.

In this embodiment, the setting of system maximum basal rate and maximum bolus amounts may be programmed to be inaccessible to the patient and only accessible through a supervisor menu. The patient's ability to access these maximum values is controlled by a maximum lock parameter that is a supervisor function. When the maximum lock feature is enabled, the user may view, but not change, the bolus maximum and the basal rate maximum. When the maximum lock feature is disabled, the user may change the bolus maximum and the basal rate maximum.

The system includes memory space and program capability to personalize the external communication device and implantable device so that information such as the patient name and physician name can be stored for later retrieval and review. For example, the personal ID may be as little as 10 characters and as much as 200 characters or more. In the linking process it is preferred that at least a portion of this information be used in determining that the external communication device has contacted the desired implantable device (assuming the implantable device has already been previously programmed with identity information. When identification information is updated in the external communication device it is passed on to and stored in the implantable device.

The system retains factory default information and may be reset to those values when operating under supervisor control so that the system may be configured rapidly to a known state. The system may also be placed in a stop mode or controlled to replace or reload implantable device software when operating under supervisor control.

As noted above certain system functions require special control and their access is restricted. These features are only accessible via a supervisor menu on the external communication device. The supervisor menu is password protected. The password may be set by the physician while in supervisor mode. The supervisor menu system may also be entered by using a factory password. The factory password may be derived from the system characteristics. For example, the factory password may be a fixed number or character pattern. It may be based on a variable parameter, such as the date reflected by the external communication device, and/or the time reflected by the external communication device, and/or the serial number of the external communication device. Supervisor options/functions include the following: (1) refill, (2) priming bolus, (3) diagnostic rate, (4) maximum lock, (5) personal ID setting, (6) initialize to factory defaults, (7) download implantable device software, (8) stop pump, and (9) set supervisor password.

The user interface uses four keys, e.g. a SEL, ACT, UP and DOWN key, to navigate through menus, display options and features, and to program values. The external communication device changes the display to the idle display which shuts off the bit map display if the external communication device keypad is idle for a predefined period of time, preferably between 2 seconds and 30 seconds, more preferably between 4 seconds and 15 seconds and more preferably between 5 seconds and 10 seconds, e.g. 7 seconds, while the user is viewing options. The external communication device may change the display to the idle display using a different predetermined time, e.g. a longer time such as 15 seconds, if the external communication device is idle while the user is in a programming or data entry screen.

As noted previously the system is programmed to display the current time and date. The time may be displayed in either a 12-hour or 24-hour format depending on user preference though in either event internal calculations that require time are based on a 24 hour clock.

All time displays by the external communication device are shown in the same format including time stamps on historical data and profile start times. This format in the present embodiment is based on a relative time measured in minutes since the factory initialization of the implantable device.

Acceptable parameter ranges for selected variables used in this first embodiment are depicted in the following table. Of course, in other embodiments other ranges are possible, other programming units may be used, some parameters may be converted to constants while other parameters may be added as variables.

Acceptable Parameter Ranges

| Parameter Name | Values |
| --- | --- |
| Automatic Off Duration | Off, 1–16 hours |
| Audio Bolus Increment | 0.4 units or 0.8 units |
| Bolus Amount | 0.2 U to Bolus Maximum by 0.2 U |
| Bolus Duration | 30 min to 4 hours |
| Maximum Bolus | 0.2 U to 35.0 U by 0.2 U |
| Hourly Maximum Bolus | 2½ times the programmed Maximum Bolus |
| Basal Rate | 0.2 U/hr to Basal Rate Maximum by 0.1 U/hr |
| Temporary Basal Rate | 0.2 U/hr to Basal Rate Maximum by 0.1 U/hr |
| Temporary Basal Rate Duration | 30 min to 24 hrs by 30 min |
| Basal Rate Maximum | 0.2 U/hr to 35 U/hr by 0.1 U/hr |
| Diagnostic Rate | 10 to 150 u/hr by 10 u/hr in U-400 |
|  | 10 to 185 u/hr by 10 u/hr in U-500 |
| Insulin Concentration | U-400 or U-500 |

As noted above, both the implantable device and the external communication device detect and report alarm conditions. The following table depicts examples of different types of alarms and examples of associated delivery states that are entered in response to the condition that gave rise to the alarm.

Alarm Conditions

| ALARM | ALARM CONDITION | ALARM STATE ACTION |
| --- | --- | --- |
| Low Battery | Alarm when there is battery energy remaining of about 8 weeks or less | Alarm Only/Icon ON |
| Depleted Battery | None guaranteed | No Delivery |
| Low Reservoir | Alarm when 2 mL of drug remaining | Alarm Only/Icon ON |
| Empty Reservoir | Alarm when 1 mL of drug remaining | Alarm Only/Icon ON |
| Any implantable device Hardware Failure Detect | Alarm | No Delivery |
| Over Delivery | Alarm when disagreement from various delivery calculations produces a discrepancy of a first type. | No Delivery |
| Under Delivery | Alarm when disagreement from various delivery calculations produces a discrepancy of a second type. | No Delivery |
| Self Test Failure | Alarm when the periodic self test including the memory test fails | No Delivery |

As noted above, even when an alarm is initially cleared, it may be reasserted if the condition that gave rise to it continues to persist. When a condition persists, the reassertion of and sounding of the alarm may occur for example as indicated in the following table.

TABLE 1

Alarm Reassertion Intervals

| Exception | Reassertion | Internal Beep | Menu Options Disabled | Persistent Icon/Message Display |
| --- | --- | --- | --- | --- |
| Over Delivery | 0 | 5 min | Yes | Yes |
| Under Delivery | 0 | 5 min | Yes | Yes |
| Low Implantable Device Battery | 7 Days | 24 Hrs | N/A | Yes |
| Low Reservoir | 24 Hrs | 24 Hrs | N/A | Yes |
| Empty Reservoir | 24 Hrs | 24 Hrs | N/A | Yes |
| Depleted Implantable Device Battery | N/A | N/A | N/A | N/A |
| Automatic Off | N/A | 5 min | N/A | Yes |

In this embodiment, physical and functional features have been considered as well as implantable longevity. In addition to the various features noted above, the implantable device and external communication device preferably meet certain physical targets: (1) The implantable device is preferably packaged in disk shaped housing that is thinner than about 1 inch, and preferably thinner than 0.9 inches, and more preferably thinner than about 0.8 inches or less, with a diameter of less than about 4 inches and more preferably about 3.2 inches or less, and having an empty weight of less than about 180 grams and more preferably less than about 165 grams, and (2) The external communication device has been packaged in a somewhat rounded but nominally rectangular shaped package having dimensions of less than about 1.0 inch by 3.5 inches by 4.0 inches, but more preferably having dimensions about 0.8 inch or less by about 2.8 inches or less by about 3.5 inches or less, and weighing less than about 6 oz. In other embodiments, various other device shapes and sizes may be used.

The implantable device and external communication device are preferably also designed and are controlled to meet certain longevity requirements in combination with the desired functional requirements. It is desired that the implantable device remain operational within the body of a patient for a period of about five years or longer, more preferably a period of about seven years or longer, and most preferably a period of about 9 years or longer. As the present embodiment uses a non-rechargeable battery, the longevity of the implantable device is primarily dictated by the power consumption of the electronic modules and the capacity of the battery. The determination of longevity is complicated by the fact that the power consumption of the electronic modules is not constant over time but varies depending on the actions that are required by the user. Two elements of the preferred embodiment that lead to an acceptable level of longevity are the use of low power electronic circuit elements and the controlled application of power and/or clocking signals to various modules. The power and/or clocking signals are supplied to the modules on an as needed basis and operational protocols have been put into place to minimize the amount of time that the various modules need to operate. As noted previously, an example of such protocols include the implantable device's attempt to communicate with the external communication device by telemetry prior to using a more power consumptive internal alarming process. Another example involves the implantable device having a storage mode that uses less power than a normal operational mode. A further example includes the implantable device's process of turning on its receive telemetry for short periods of time (about four milliseconds) on a periodic basis (once every two seconds) to listen for incoming messages and then shutting off the telemetry system if no messages are incoming. An additional example, includes the processor's ability to turn itself off when it is not needed and to be awakened by interrupt signals when needed. These and other examples of controlled power consumption are discussed further hereafter.

Figure 3:
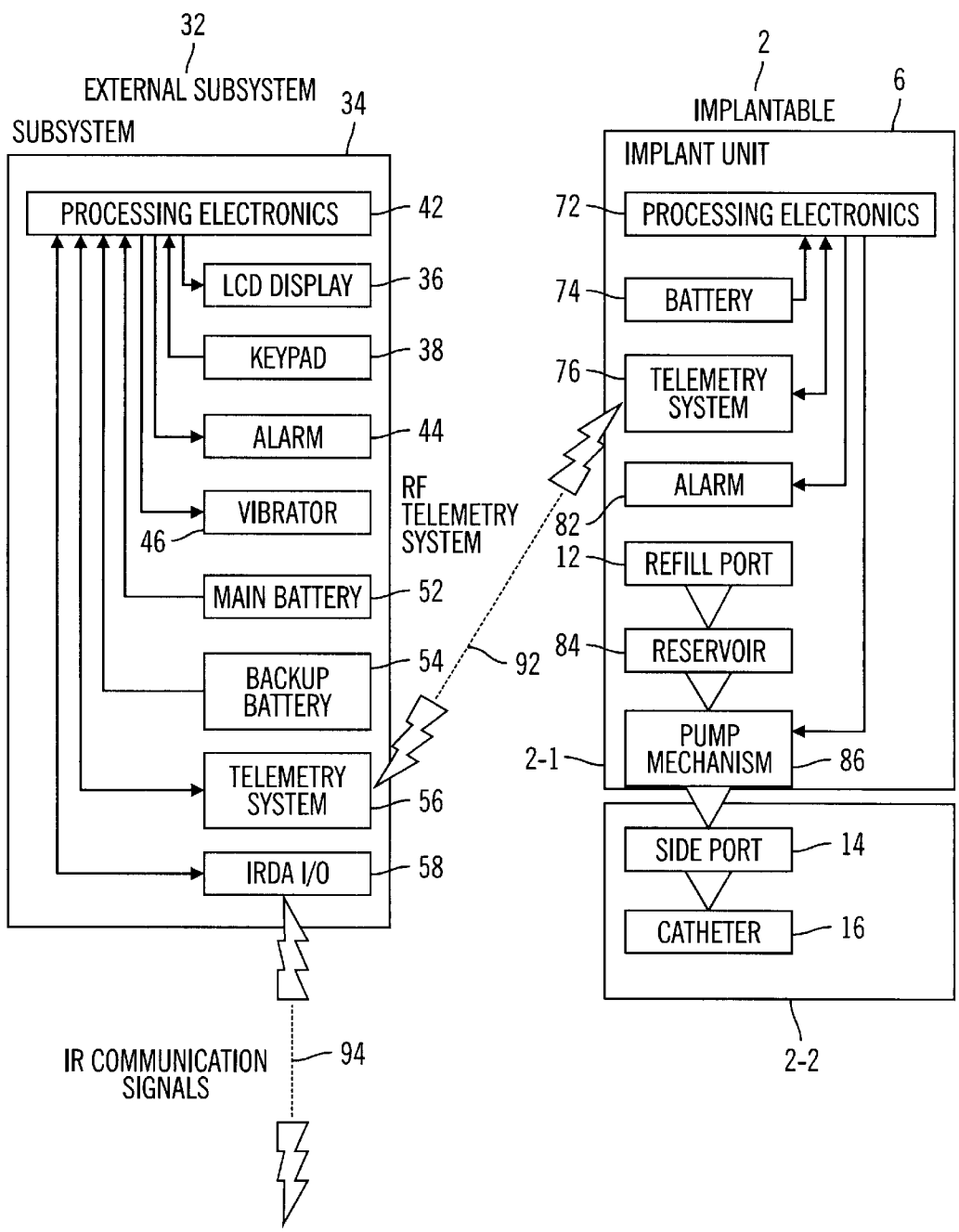
FIG. 3 depicts a block diagram of the main components/modules of both the implantable device and the external communication device of the first preferred embodiment.
Figure 4:
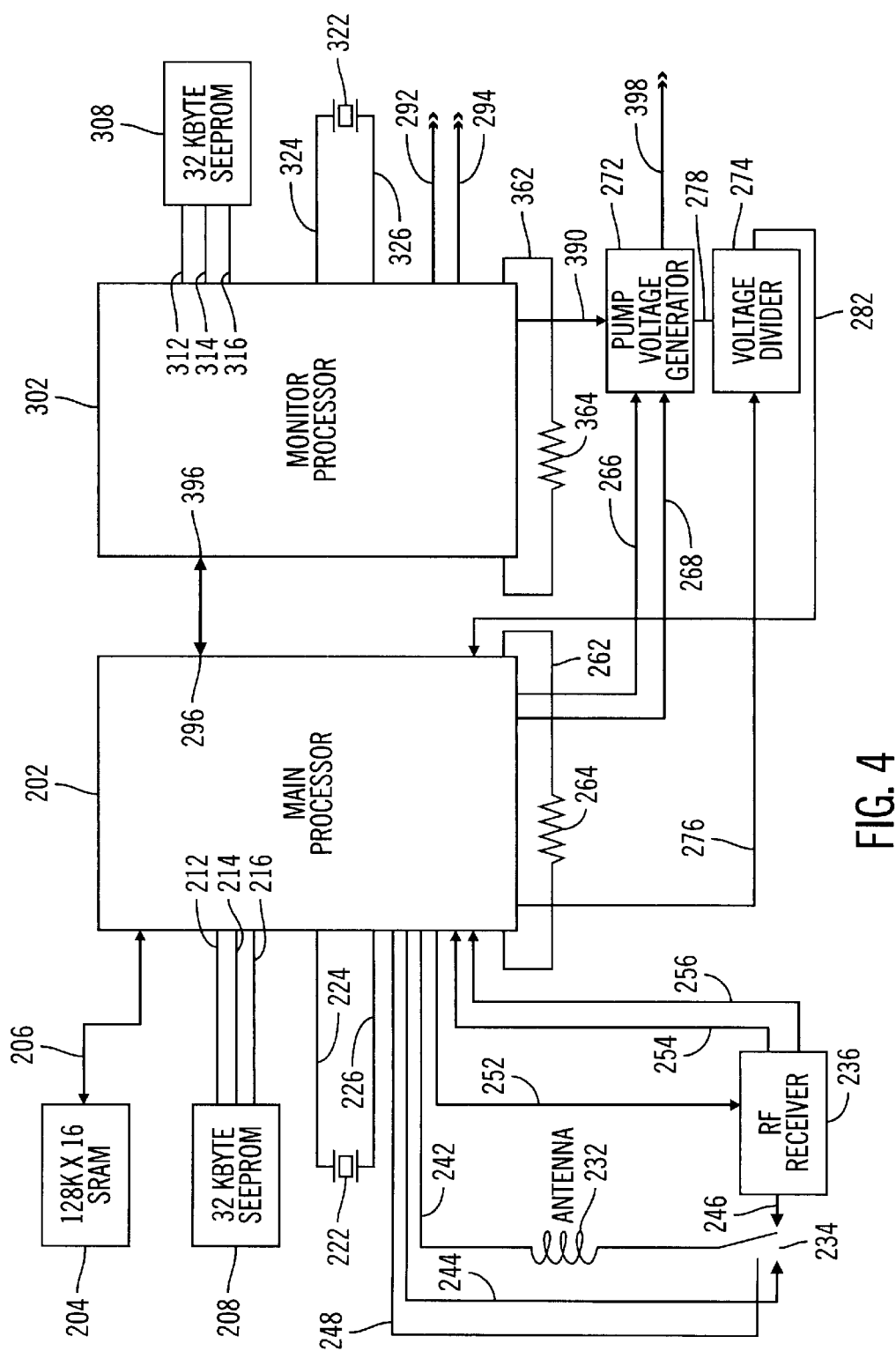
FIG. 4 depicts a block diagram of the main modules and components of the control electronics of an implantable infusion pump of the and their inter-connections as used in the first preferred embodiment.

FIG. 3 depicts a simplified block diagram of various functional components or modules (i.e. single components or groups of components) included in the implantable medical device 2 and external communication device 32. The external communication device 32 includes (1) a housing or cover 34 preferably formed from a durable plastic material, (2) processing electronics 42 including a CPU and memory elements for storing control programs and operation data, (3) an LCD display 36 for providing operation for information to the user, (4) a keypad 38 for taking input from the user, (5) an audio alarm 44 for providing information to the user, (6) a vibrator 46 for providing information to the user, (7) a main battery 52 for supplying power to the device, (8) a backup battery 54 to provide memory maintenance for the device, (9) a radio frequency (RF) telemetry system 56 for sending signals to the implantable medical device and for receiving signals from the implantable medical device, and (10) an infrared (IR) input/output system 58 for communicating with a second external device.

The second external device may include input, display and programming capabilities. The second device may include a personal computer operating specialized software. The computer may be used to manipulate the data retrieved from the communication device or the medical device or it may be used to program new parameters into the communication device or directly into the medical device, or even used to download new software to the communication device or to the medical device. The manipulation of the data may be used in generating graphical displays of the data to help aid in the interpretation of the data. Such data interpretation might be particularly useful if the medical device provides data concerning a physiological parameter of the body of the patient, such as a glucose level versus time. More particularly the computing power and display attributes of the second device might be even more useful when the medical device includes both an implanted sensor (e.g. glucose sensor), or external sensor, and an implanted pump (e.g. insulin pump), or external pump, where the second external device may be used to enhance the ability to ascertain the effectiveness of the two devices working together. Successful control periods and problem control periods could be more readily identified. In fact, if the two devices work on a closed loop basis or semi-closed loop basis, the analysis performable by the second external device may be useful in deriving new closed loop control parameters and/or in programming those parameters directly into the communication device or the medical device or devices.

The implantable device 2 includes (1) a housing or cover 6 preferably made of titanium that may or may not be coated to enhance biocompatibility, (2) processing electronics 72 including two CPUs and memory elements for storing control programs and operation data, (3) battery 74 for providing power to the system, (4) RF telemetry system 76 for sending communication signals (i.e. messages) to the external device and for receiving communication signals (i.e. messages) from the external device, (5) alarm or buzzer 82 for providing feedback to the user, (6) refill port 12 for accepting a new supply of drug as needed, (7) reservoir 84 for storing a drug for future infusion, (8) pumping mechanism 86 for forcing selected quantities of drug from the reservoir through the catheter to the body of the patient, (9) sideport 14 for providing a replaceable connection between the (10) catheter and the pump housing and for allowing diagnostic testing of the fluid handling system to occur, and catheter 16 for carrying medication from the implant location to the desired infusion location.

In this embodiment, the pump mechanism is preferably a low power, electromagnetically driven piston pump. Such as for example Model Nos. P650005 or P650009 as sold by Wilson Greatbatch Ltd. of Clarence, N.Y. which have stroke volumes of 0.5 microliters and draw under 7 mJ (e.g. about 6 mJ) per pump stroke and under 4 mJ (e.g. about 3 mJ) per pump stroke, respectively. The pump mechanism dispenses a sufficiently small volume of insulin per stroke so that a desired level of infusion resolution is achieved. For example if an infusion resolution of 0.2 units of insulin were desired when using U400 insulin, then a stroke volume of about 0.5 microliters would be appropriate. In other embodiments other types of infusion pumps may be used, e.g. peristaltic pumps, screw driven pumps, and the like.

As depicted in FIG. 3, the implantable device includes a reservoir 84 for holding a desired quantity of insulin. In this embodiment, the drug held in the reservoir is preferably maintained at a slight negative differential pressure (with respect to the pressure on the outside of the housing) so that in the event of a leakage in the reservoir 84 or housing 6, the drug will not be forced from the housing into the body of the patient. The drug is added to the reservoir 84 by means of a transcutaneous needle that is passed from a position exterior to the body into self sealing refill port 12. Due to the slight negative pressure that the reservoir experiences, insulin in a syringe connected to the needled is drawn into the reservoir without need of external force. The drug is extracted from the reservoir 84 and forced through catheter 16 by an electronically controlled pump mechanism 86. In alternative embodiment positive pressure reservoirs may be used in combination with pumping mechanisms that force the medication or drug from the implantable device and/or used with flow restrictors that dispensed the drug at a fixed rate or at a variable rate with the aid of valves or flow diverters.

The size of the reservoir is preferably large enough to hold sufficient insulin so that refilling does not have to occur too often. For example, it is preferred that time between refills be within the range of 1.5–4 months or longer, more preferably at least 2 months, and most preferably at least 3 months. Opposing the containment of a large volume of insulin, is the desire to keep the implantable device as small as possible. In the present embodiment the implantable device and reservoir has been designed to hold about 13 ml of insulin. A preferred insulin has a concentration of 400 units per milliliter and is available from Aventis HOE 21 Ph U-400 from Aventis Pharma (formerly Hoechst Marion Roussel AG, of Frankfurt am Main, Germany). This insulin is a highly purified, semi-synthetic human insulin with 0.2% phenol as a preserving agent, glycerol as an isotonic component, TRIS as a buffer, plus zinc and Genopal® as stabilizing agents. This quantity and insulin concentration allows about 2–4 months between refills. In other embodiments higher insulin concentrations may be used (e.g. U-500 or U-1000) to increase time between refills or to allow reduction in reservoir size. In some embodiments, when higher concentrations are used, any quantized minimum delivery amounts may be reduced by modifying the pumping mechanism, control circuitry, or software control algorithm so that infusion resolution is not adversely impacted.

The external communication device contains appropriate software to provide proper control of the device including appropriate functionality to allow communication with the medical device, to allow adequate control of the operation of the medical device, and to give appropriate feedback to the user regarding overall system operation. The medical device is provided with appropriate software to allow communication with the external communication device, to allow safe and appropriate operation of the medical functionality of the device, and to allow direct feedback to the user concerning device status via the internal alarm.

The control electronics of both the implantable device and external communication device are centered around microprocessor based integrated circuits, i.e. processor ICs, that are implemented in the present embodiment in the form of application specific integrated circuits (ASICs). Two such ASICs are used in the implantable device to increase operational safety of the device by configuring the device to require that the two ASICs act in conjunction with each other in order for medication infusion to occur.

In different embodiments, more or less of the control electronics may be implemented within one or more processor ICs while any remaining portions may be implemented external to the processor IC(s). The processor IC may be referred to as an MD processor if used in the medical device portion of the system or a CD processor if used in the communication device portion of the system. In other embodiments the process IC used in the communication device may be different, e.g. have a different CPU or different peripheral modules, from a processor IC used in the medical device. In embodiments where more than one processor IC is used in either the medical device or the communication device each of the processors may be different. They may be specifically designed for their intended roles when they perform at least partially different functions. Depending on particular design constraints portions of the electronics not embodied in the processor ICs may form part of one or more hybrid circuit boards or be otherwise mounted within, on, or even in some cases external to a device housing.

Figure 5:
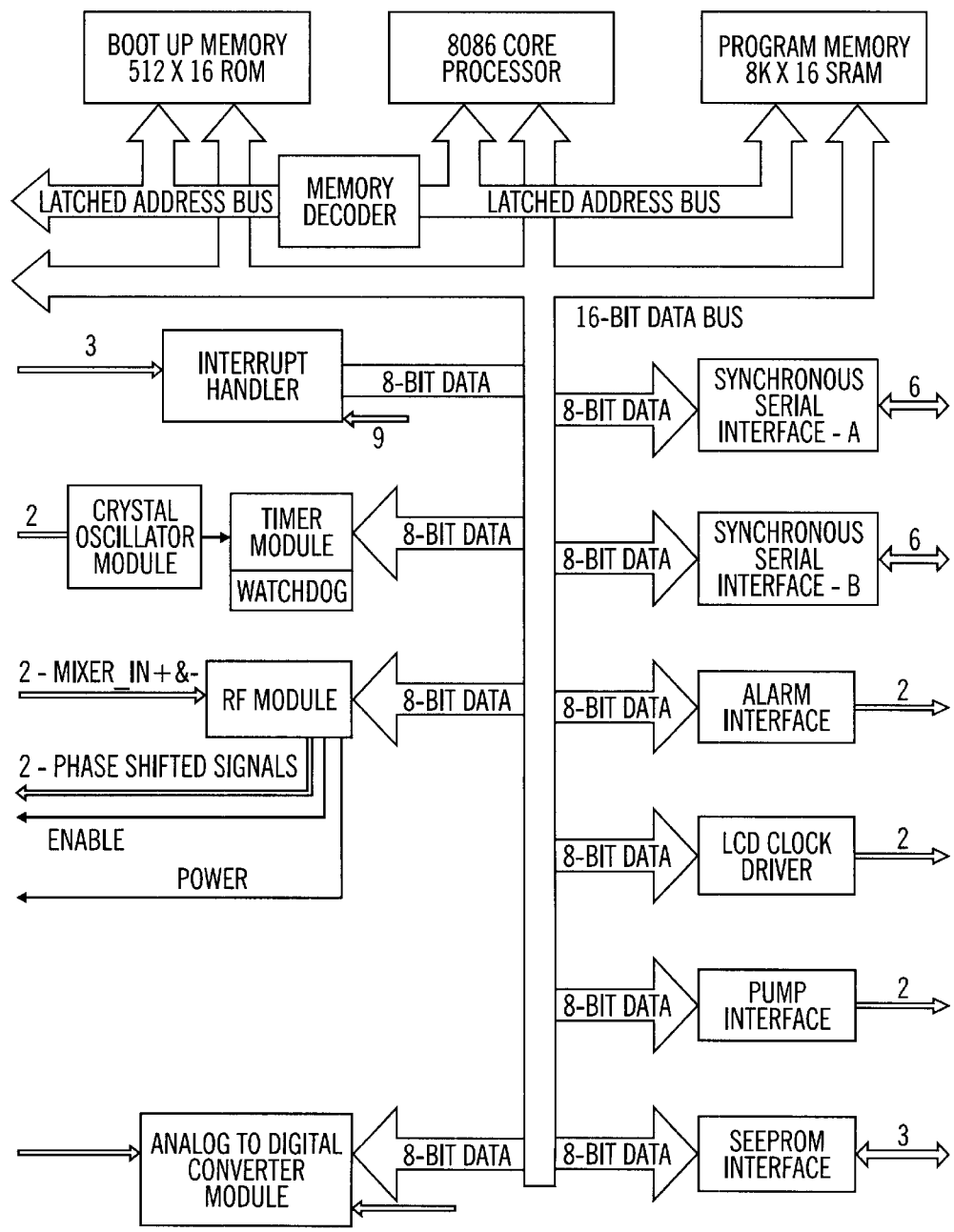
FIG. 5 depicts a block diagram of the various modules of the Processor IC used in both the implantable device and the external communication device of the first preferred embodiment.

A functional block diagram of the Processor IC for the present embodiment is depicted in FIG. 5. Each processor IC of the present embodiment includes a CPU 912 and various peripheral modules that are used for system control, data acquisition, and interfacing with electrical components external to the processor IC.

The peripheral modules of the processor IC of the present embodiment include (1) a non-volatile memory interface module, e.g. a SEEPROM interface module 914, (2) a boot ROM module 916; (3) an SRAM module 918; (4) a memory decoder module 920; (5) a crystal oscillator module 922; (6) a timer module 924; (7) a pump interface module 926; (8) a watchdog module 928; (9) an RF telemetry module 930; (10) an interrupt handler module 932; (12) an analog-to-digital converter module 934; (13) an LCD clock driver module 936; (14) an alarm interface module 938; and (15) first and second synchronous serial interface modules 942 and 944. The memory decoder module interfaces with the core processor, boot ROM, and internal SRAM using a 16 bit address bus which also is available off chip for addressing external memory. With the exception of the crystal oscillator module all other internal module communicate over an 8-bit data bus or 16-bit data bus. FIG. 6 further illustrates that the A/D module may take input from sources internal to the processor IC and similarly the interrupt handler can take up to 9 interrupts from sources internal to the processor IC. Additionally, most of the modules communicate with outside components or modules over one or more input/output lines.

In alternative embodiments fewer, additional, or different peripheral modules may be incorporated into the processor ICs. In one extreme the processor IC may simply incorporate a CPU with all other modules being external thereto. In the other extreme almost all, if not all, electronic components may be incorporated into a single processor IC. Intermediate alternatives might incorporate a single additional module into the processor IC (in addition to the CPU), others might incorporate more than one, e.g. 4 or more, 8 or more, or the like. In still other alternatives, the number of peripheral modules or components in an entire device may be considered and more than a certain percentage of them incorporated into one or more processor ICs, e.g. more than 50%, more than 75%, or even more than 90%.

The processor ICs are responsible for basic system management and communication of information between the implantable device and the external communication device through the RF telemetry link. The telemetry systems of the present embodiment are implemented in part through electrical hardware and in part through software controlled by a processor IC.

In the present embodiment, most of the required electrical modules for the implantable device are integrated within the processor ICs. However, several are not. These additional modules include two independent crystal oscillators (one for each ASIC); two non-volatile memory modules (one for each ASIC), e.g. SEEPROM chips; a volatile memory module (used only by one of the ASICs), e.g. an SRAM chip; pump driver circuitry (partially controlled by the each ASIC); front end telemetry system circuitry; and voltage measurement circuitry associated with the pump driver circuit; a buzzer; and a battery.

Within the implantable device telemetry operations are controlled by a single ASIC (sometimes known as the main processor). The other processor (sometimes known as the monitor processor) controls the buzzer and is thus responsible for audio communications coming from the implantable device. The medical functionality of the implantable device (i.e. the administration of insulin in the present embodiment) is controlled by both processors. To maintain the implantable device in a fail-safe operational mode, these two processors must maintain an appropriate level of agreement concerning infusion instructions or a system reset is forced to occur. The main and monitor processors communicate with each other through the use of hardwired serial input and output ports.

As with the implantable device, the control electronics of the external communication device are centered around an ASIC that controls and interacts with a number of peripheral modules. These peripheral modules include an LCD display and driver, an IR port and driver, a crystal oscillator, a keypad and keypad interface, power management modules and reset circuitry, external volatile memory (e.g. SRAM) and non-volatile memory (e.g. SEEPROM), a buzzer, and front end telemetry hardware.

In the present embodiment, the control electronics of the implantable device are centered around two identical application specific integrated circuits (ASICs) that are mounted on a hybrid circuit board. In some alternative embodiments a single ASIC may be used, or a single dual processor integrated ASIC may be used. In the single dual processor integrated ASIC, dual circuitry would be provided so that each processor could act independently of the other. In the single dual processor embodiment, a single off-circuit oscillator may be used to drive both processors or each may have an independent oscillator. A single chain of timing circuits could be used in driving both processors or independent chains of timing circuits could be used. Furthermore, if a single oscillator is used to drive both processors, then one or more separate circuits such as a counter and an RC timer may be used to verify appropriate operation of the oscillator and/or any particular timing circuit dependent thereon.

In the present embodiment, most of the required modules for operating the implantable device are integrated within the processor ICs. However several are not. Along with the two ASICs mounted on the hybrid circuit board other components are also mounted there, for example, two independent crystal oscillators (one for each ASIC), two SEEPROMs (one for each ASIC), an SRAM chip, pump driver circuitry, telemetry system circuitry, and voltage measurement circuitry associated with the pump driver circuit.

In the present embodiment, an external SRAM chip is connected to a single one of the ASICs. With the exception of a pumping mechanism, a buzzer, a battery, and a conductor that grounds the hybrid board to the housing 6, all electrical components of the system are mounted on the hybrid board. The RF tuning and the receiver amplifier circuits are kept outside the processor ICs to better isolate weak RF receive signals from the digital noise of the processor IC. The Pump driver circuitry has been implemented outside the IC due to the large difference in voltage requirements that exist between the chosen pump driving circuitry and the other modules incorporated in the processor IC.

To improve longevity, while maintaining reduced size, the hybrid board is preferably populated with low power components and is further configured to operate with a low quiescent power consumption. The low quiescent power is enabled by utilization of selected components, or modules, in combination with control capability so that modules may be toggled quickly between "off" states (i.e. states where power consumption is turned off, or reduced, wherein the normal activity of the component, or module, is reduced or completely eliminated) and "on" states (i.e. states where the components or modules are enabled to have their desired functionality). The transition between "on" and "off" states may occur in different ways. In the present embodiment, for example, transitions are made by one or both of withdrawing power from the component, or module, or withdrawing a clocking signal from the component or module. Typically the withdrawal of power or a clocking signal is controlled by the core processor (i.e. CPU) of the ASIC by controlling the values that are placed in numerous hardware control registers.

In the present embodiment, it is preferred that the quiescent current be less than or equal to about 100 microamperes at about 3 volts, more preferably less than or equal to 50 microamperes at about 3 volts, and most preferably less than or equal to about 25 microamperes at about 3 volts. In the present embodiment, quiescent current is measured when both processors are in a sleep mode with RF transmission and reception turned off, and with a pump clock turned off.

A block diagram for the hybrid circuit in the implantable device is shown in FIG. 5. The hybrid circuit includes, among other things, a first processor IC designated as the main processor 202 and a second processor, designated as the monitor processor 302. In this embodiment, the main processor 202 and monitor processor 302 are identical.

The main processor 202 is functionally connected to an SRAM Module 204 by address, data, and control lines 206. The external SRAM 256 provides 256 kbytes of memory. A preferred SRAM module is configured to operate between 2.3 and 3.3 volts, to consume no more than 10 uA during standby, and more preferably no more than about 2 uA.

This amount of memory has been selected as it is believed to be adequate to hold at least 120 days of insulin delivery data and other log data. In the present embodiment, the purpose of this SRAM is to provide data storage only as all program code is stored in RAM that is internal to the processor ICs. In alternative embodiment program code could be store at least in part in external memory while some log data could be stored in internal memory.

The Main Processor is also functionally connected to SEEPROM module 208, by power line 212, clock line 214, and data line 216. The external SEEPROM 208 provides 32 kbytes of memory. A preferred SEEPROM is a 2 wire device operating between 1.8 volts and 3.6 volts using bi-directional data transfer protocol and is organized in 8-bit words.

The main processor is also connected to an external crystal oscillator 222 by lines 224 and 226. The external crystal oscillator 222 is a 1,049,100 Hz crystal +/−500 Hz (i.e. $2^{20}$+about 500 Hz) and is preferably of the hermetically-sealed ceramic type with a motional capacitance of 1.7 femtofarads, a maximum motional resistance of 1.5 kΩ with a quality factor of about 60,000, and a shunt capacitance no greater than 1.0 pF. This oscillator provides the clock source for the CPU and all the modules including the RF telemetry.

The main processor IC includes a portion of the RF telemetry hardware necessary for the implantable device to communicate with the external communication device while the remaining portion of the telemetry hardware is mounted on the hybrid board. The RF telemetry subsystem is composed of analog and digital modules. The digital modules include a QFAST® modulator/demodulator, control and timing logic circuits and are incorporated in the Processor IC. The analog modules include a mixer circuit and a low-pass filter circuit that are also incorporated into the processor IC. The analog modules further include an antenna 232, a switch 234 and RF receiver 236 that are provided on the hybrid board but external to the Processor IC. These components/modules were left outside the Processor IC to minimize negative effects that digital noise from the processor IC might have on the weak RF signals that are to be received.

The antenna has a ferrite rod having a length of about one inch and a diameter of 0.150 inch with an inductance of about 950 uH, DC resistance of about 4 ohms, and an unloaded Q-Factor of 46 minimum. The antenna is surface-mounted onto the hybrid board and electrically connected to the hybrid board through a two-wire connector.

The switch 234 includes a tristate driver and an analog switch. The tristate driver and analog switch are controlled by an RF receive power enable signal on line 248. When the enable signal is low the tristate driver is enabled, the analog switch is open, lines 242 and 244 are connected together through the antenna, and the antenna is disconnected from line 246, thereby enabling RF transmission. On the other hand, when the enable signal is high, the tristate driver is disabled, the analog switch 234 is closed opening the connection between lines 242 and 244 and connecting line 242 to line 246 through the antenna, thereby enables reception.

The transmitter section receives two phase shifted digital transmit signals from the Processor IC. These are quadrature-modulated components of the data which are generated within the Processor IC based on about a 250 kHz (e.g. about $2^{18}$ Hz) carrier. The two signals are coupled into opposite antenna leads during transmission. The main processor activates both the signal lines 242 and 244 to generate transmission through the RF antenna. Before passing to the antenna 232, the signal on line 242 is passed through a tristate driver that is continuously enabled. Before passing to the antenna, as explained above, the other signal also passes through a tristate driver that is preferably identical to driver 652. Having both signals pass through the equivalent tristate drivers helps ensure that the signals maintain the proper phase relationship.

The RF receiver module 236 receives power at a voltage of about 1.8 to about 1.9 volts from the main processor on line 252 and provides two input signals to the main processor on lines 254 and 256, respectively.

The RF receiver module 236 includes three amplifier stages that are tuned to pass and amplify desired signals. The first RF receiver stage includes a tuned amplifier circuit that amplifies small RF signals of selected frequency and bandwidth. Frequency response of the first stage is set by a tank circuit with tuning adjustable by a binary capacitor. The signal from the tank circuit is passed through a direct current blocking capacitor and then on to a pair of NPN bipolar transistors having an output capacitance of 4 pF. Appropriate resistors, capacitors and biasing voltages are also provided to appropriately bias the transistors so that the first stage provides a desired level of frequency selection and gain (e.g. a gain of about 20–30). A signal from this stage is fed into a second stage amplifier through a resistor and a direct current blocking capacitor.

The second RF receiver stage provides a second tuned amplifier using two transistors configured in a push-pull configuration with the frequency response being set by a tank circuit having an adjustable response based on a binary capacitor. The binary capacitor and push-pull transistors may be the same as those noted above with regard to the first stage. Appropriate resistors, capacitors and biasing voltages are also provided to appropriately bias the transistors so that the first stage provides a desired level of frequency selection and gain (e.g. a gain of about 10–20). A signal from this stage is fed into a second stage amplifier through a resistor.

The third RF receiver stage includes a flat response amplifier circuit having a small gain (e.g. a gain of about 2–5). The gain in this stage is provided by a pair of transistors that are in a push-pull configuration and which may be identical to those noted above with regard to the first stage. Appropriate resistors, capacitors and biasing voltages are also provided to appropriately bias the transistors to achieve the desired level of gain.

The signal resulting from these three stages is preferably amplified by 60 to 70 dB with an RF passband of about 16 kHz (i.e. $2^{14}$ Hz) around the 250 kHz carrier at a 2 dB ripple peak-to-peak max. An RF stopband of about −40 dB is provided at about 150 kHz and below and at about 550 kHz and above.

The line carrying the output signal from these three stages is taken to ground through an 82 kΩ resistor and then a 390 pF capacitor. A first signal is taken from the output signal prior to the output signal passing through the resistor. A second signal is taken from the output signal from between the resistor and the capacitor. The two signals are then passed onto the main processor IC.

The main processor also provides an external line 262 that carries a reset signal from an internal watchdog circuit output to an external reset input. Line 262 includes a resister 264 (e.g. 10 kΩ resistor) to condition a signal being transmitted along the line.

The main processor further provides a power signal and a clocking signal on lines 266 and 268, respectively to a pump voltage generator circuit 272.

The main processor additionally provides an activate signal to control a switch (e.g. a MOSFET) within a voltage divider circuit 274, by line 276, to activate the divider circuit which in turn receives a voltage level input on line 278 from the pump voltage generator circuit 272 and provides a reduced voltage signal on line 282 back to an analog-to-digital converter (ADC) input on the main processor so as to enable a pump circuit voltage measurement and analysis to be made.

The monitor processor 302 is functionally connected to a SEEPROM 308 of the same type as used in conjunction with the main processor 202 and is connected thereto in an analogous manner using power line 312, clock line 314, and data line 316.

The monitor processor is also functionally connected to an external crystal oscillator 322 of the same type as used in conjunction with the main processor by lines 324 and 326.

The monitor processor further supplies two power lines 292 and 294 that carry two power signals to a buzzer. The signals are output to a connector on the hybrid board. The signals are then carried by cable to a piezo electric buzzer that is mounted to an inside wall of the housing 6.

The monitor processor also provides an external line 362 that carries a reset signal from an internal watchdog circuit output to an external reset input. Line 362 includes a resister 364 (e.g. 10 kΩ resistor) to condition a signal being transmitted along the line.

The monitor processor additionally provides a firing signal by line 390 to the pump voltage generator circuit when it is time to activate the pump mechanism. The pump voltage generator 272 provides two lines 398 that connect to the pumping mechanism located off the hybrid circuit so as to allow current to flow through the coil of the pumping mechanism when a firing command is given by the monitor processor.

The pump voltage generator 272 charges two large capacitors within the pump voltage generator module 272 to approximately 16 Volts. The capacitors are about 22 μF each thereby providing an effective capacitance of 44 μF. Upon receipt of a fire signal on line 390 from the monitor processor, the pump circuit discharges the capacitors through the pump coil via two lines 398 to initiate the pump action.

The capacitor charge operation is controlled by two signals generated by the main processor. A pump power signal on line 266 activates a transistor switch (not shown) enabling power (nominally at 3 volts) to reach a charging inductor (not shown). A pump clock signal on line 268 completes the rest of the circuit by activating a second transistor switch (not shown) in a pulsed manner thereby allowing pulsed current to flow through inductor 618. As transient current is pulsed through the inductor, a higher voltage than the nominal amount supplied is developed which is bled into a charging bank containing the two capacitors noted above. Back flow of built up current is inhibited by a diode. A clock rate of about 60–70 kHz (e.g. about 216 Hz) is used for modulating the second transistor. The capacitor bank provides one output to an inductive coil of the electromagnetic pump mechanism. A lead returns from the other end of the pump mechanism and passes through a third transistor switch before reaching a ground line on the hybrid board. When the third switch is in an open state (deactivated), the charge in the capacitor bank is inhibited from reaching ground. The previously mentioned firing signal on line 390 from the monitor processor causes selective activation of the third switch and thus enables the capacitor bank to discharge itself through the inductive coil of the pump. The third switch is preferably a power field effect transistor (FET) with a very small "on" resistance ( e.g. about 0.05Ω or less). The pump capacitors are protected against over-charging by a Zener diode having a maximum voltage of about 21 volts.

The main and monitor processors include serial input and output ports 296 and 396 respectively. The main and monitor processors communicate through a first bidirectional, hardwired, six wire synchronous serial interface through these ports. Two signals, data and clock, are used to transfer information from the main processor IC to the monitor processor IC. Two signals, data and clock, transfer information from the monitor processor IC to the main processor IC. Read and clear signals provide for handshake between the main and the monitor processor ICs. The interface clock frequency is half the crystal oscillator frequency.

The hybrid circuit is preferably powered by a battery 402 that provides a voltage between about 2.3 volts to about 3.6 volts. A preferred battery is a lithium(anode) carbon monofluoride (cathode) battery having an initial capacity of preferably more than about 2600 mA-Hr while maintaining a loaded output voltage of at least 2.4 volts when drawing a 6 mA current. A preferred battery is Model No. 9646 from Wilson Greatbatch, Ltd. of Clarence, N.Y.

In summary, the outputs of the implantable device hybrid circuit include a two line controllable voltage signal 398 as produced by pump voltage generation circuit 272 for driving an off-board pump mechanism, a two line audible alarm signal carried on lines 292 and 294 as produced by the monitor processor for driving an off-board piezo electric alarm to allow implantable device status information to be supplied directly to the patient, and two RF transmission signals that are combined as radiated from the antenna for communicating information to the external communication device. An additional output includes a ground connection (not shown), passing through a 2 MΩ resistor going to the titanium housing of the implantable device. Inputs to the of the implantable device hybrid circuit include power from a battery and two filter and amplified telemetry input signals.

As discussed above, a single processor IC is used in the external communication device while two processor ICs are used in the Implantable Device. In this first preferred embodiment all three of these processors are identical.

As it is preferred that the implantable device have a long implanted life, and as the implantable device of the present embodiment does not use rechargeable batteries, a low-power constraint is imposed on the processor IC. This low power constraint is three fold: (1) use of low power circuit elements and design, (2) use of electronic modules that are capable of being put into low-power consuming states or non-power consuming states when not needed to perform specific functions, and (3) use of control hardware or software to put the modules in their reduced power states and to pull them out of those states. The result is that the processor IC is designed and controlled to operate at an average power of less than about 30 μW. At a supply voltage of 2.9 Volts, this power consumption turns into an average current of less than about 11 μA. The entire implanted electronic system preferably draws an average of less than about 32 μA. In this embodiment, the processor IC operates with a voltage of between about 2.3 V and 3.6 V. To achieve desired overall power consumption for the implantable device, the processor IC is a custom designed CMOS device using 0.8 micron technology with the physical construction of cell design utilizing small gates, drains, and diffusion regions.

The core processor 912 design preferred in the present embodiment is a CMOS low power version of the INTEL 8086 processor with a minimized number of logic gates and enhanced timing so as to consume less power. The Core Processor includes ten additional instructions so that it is software compatible with the 80186 processor. It is a multiplexed bus device having the 16 low order address bits, out of a total of address bits, multiplexed with the 16 data lines. De-multiplexing is achieved with on-chip latches so that the low order 16 address lines are available as outputs to the device. The four high order address lines and the bus high enable signal are not multiplexed. As noted above, the processor IC also integrates a number of modules and functions so as to reduce the power consumption as compared to using discrete components for achieving the same functionality.

A SEEPROM interface 914 is provided within the processor IC for exchanging information with an off chip SEEPROM device. A two line interface is used to exchange data with the SEEPROM device and a power line is also supplied from the processor IC to the SEEPROM so that it may be selectively powered so as to reduce power consumption when access to the SEEPROM is not needed. In the present embodiment, the SEEPROM associated with each of the two processor ICs in the implantable device has a capacity of 32 kbytes while the two SEEPROMs used in the external communication device have a capacity of 64 kbytes each. In the present embodiment, the SEEPROM provides periodic acknowledgments when the SEEPROM is interacted with. A SEEPROM control register and a SEEPROM data register are also provided. These two registers provide a bit that supplies power to the SEEPROM, a bit that provides an oscillating signal to the SEEPROM, a bit that provides data to be written to the SEEPROM, and a bit that can be read to pickup data that is being supplied by the SEEPROM.

The Boot ROM 916 is an on-chip read only memory that provides the initial boot code for the CPU. The Boot ROM is 1 kbyte metal mask programmable ROM.

The address location of the beginning of the boot ROM 916 is consistent with the Intel 8086 specification for reset vectors. When reset occurs, the processor begins execution of the code found in ROM which is a program that loads further code from the SEEPROM located off-chip. Further details on execution of the ROM code may be found in the previously referenced U.S. patent application Ser. No. 09/768,045.

A 16 kbyte section of static RAM (SRAM) 918 is provided within the ASIC. This space is used for stack, general variables, and core program space such that most of the operational implantable device code and external communication device code reside in this space.

The processor IC includes a memory decoder module 920 that is capable of decoding the 16 kbytes of internal SRAM and is also directly capable of decoding 512 Kbytes of external memory. The memory decoder contains Boolean logic gates to decode the 8086 address space for each individual bus transaction. The amount of externally addressable SRAM may be increased by adding one or more additional bank select triggers such as by using the a processor IC output that is not being used for some other function. For example, in the external device the output signal that is used to fire the pump mechanism may instead be used as a bank select signal as it is otherwise not being used. This provides the ability for the external communication device to be able to decode 1 Mbyte, or more, of external SRAM. The memory decoder is further capable of decoding the 1 Kbyte of internal ROM.

A low power crystal oscillator module 922 internal to the Processor IC is used in conjunction with the an external oscillator crystal and a shunting resistance to provide a stable 1.049100 MHz +/−500 Hz clock source while drawing less than about 2 μA from a 2.2 V to 3.5 V supply. The circuit is intended to operate with a minimum frequency of 1.048576 MHz crystal using a shunt resistance of about 20 MΩ in the implantable device and about 2 MΩ in the external communication device. The shunt capacitance of the crystal is preferably no greater than 1.5 pF. An external shunt resistor is provided in parallel to the clock crystal across two external connectors of the ASIC to provide DC feedback to the circuit. The amount of resistance is selected as a balance between oscillation start up and current consumption.

The timer module 924 is composed of the system clock generator and circuits responsible for generating various timing signals. The processor IC uses the (1.048576 MHz+ 500 Hz) external crystal to generate the system clocks. Tolerance of the crystal oscillator is be better than +/−500 parts per million (ppm) including the drift due to aging, and temperature induced variances within a range of −10° to 50° C.

The Timer Module 924 consists of a (A) system clock generator; (B) a CPU clock module; (C) a pulse stealer; (D) a clock enable register; (E) four independent timers (wake up 1, wake up 2, sleep, and one minute), and (f) a time-of-day timer that can be made to register time in subsecond intervals.

The system clock generator module, is a 20 bit ripple counter that has the ability to load a pattern into its lower 14 bits. This counter is used to provide the system clocks necessary for operation of all other modules. In the present embodiment a pulse stealing technique is used to fine tune the oscillation frequency for all clock signals generated by this module that have a frequency of about 8192 Hz or less.

The clock frequency of the CPU (i.e. the frequency of the CPU clock) may be selected and the CPU clock made to stop by writing appropriate values to appropriate CPU clock registers. The frequency select circuit consists of two registers and a synchronizing circuit. The synchronizing circuit is used to ensure that narrow clock signals (i.e. glitches) are avoided when the frequency of the CPU Clock is changed.

A pulse stealer circuit is provided for precise system timing of selected clock signals. In the present embodiment the pulse stealer function is applied to the clock signal that has a frequency that is just slightly more than 8192 Hz target frequency as provided by the system clock generator. The pulse stealer circuit gives the ability to periodically steal pulses from a selected clock signal to produce a clock signal of lower and more desirable average frequency. In the present embodiment the pulse stolen signal, is used to create all system clocks that of lower frequency. In implementing pulse stealing for the present embodiment, the CPU loads a 16 bit value into two eight bit configuration registers. The timer whose signal is to be modified is used to cause a counter to count up from zero to the value loaded into the registers at each time a comparator recognizes a match. After the counter reaches the value specified in the registers, a single pulse is removed from the output signal (stolen from the output signal) to provide the modified output signal. Then the counting begins again from zero and the process is repeated over and over so that a modified output signal, or pulse train, having a desired average frequency is generated.

A clock enable control register is provided so as to allow the CPU to selectively enable or disable the clock signals used by other modules. In the present embodiment these other modules include the first and second synchronous serial ports, the analog-to-digital converter, and the insulin pump charging circuitry. Enablement/disablement for a given module is "bit mapped" to the control register so that the control register may be used to "gate" these clocks on or off.

Four system timers are provided. These timers provide interrupts to the CPU at selected intervals. The internal logic of the first three of these timers is identical with the exception of the input clock frequency and the number of bits to count to before causing an interrupt. The interrupt interval for each timer is programmable by the CPU by writing an appropriate value to an appropriately sized control register associated with each timer. Once an interrupt interval is written into the timer by the CPU, interrupts will be continuously generated by the timer without further intervention of the CPU. The timers continue to "run" independent of when or if the CPU services the interrupts that they create. Thus, interrupts will continue to be "issued" at the same programmed interval, and will stay asserted if not serviced. The act of servicing the interrupt clears the interrupt condition. The CPU clears any pending interrupts by writing to the associated control register.

The first of these timers is the first wake-up timer and it generates a first wakeup signal that based on a 1 Hz input clock frequency and a programmed count value that is to be reached before generating its interrupt signal. Examples of the use of this timer in the present embodiment include Watchdog monitoring and nominal RF reception and transmission start times.

The second of these timers is the second wake-up timer and operates off an 8 Hz input clock frequency and is also programmable to count to a specified value before generating its interrupt signal. Examples of the use of this timer in the present embodiment include various uses within the external communication device, including spinning the pumping status indicator on the display panel, IrDA timing for missing bytes and closing the channel, beeping, and keyboard blink timing.

The third timer is the sleep timer which operates off a 1,024 Hz input clock frequency and is programmable to count to a specified value before generating its interrupt signal. An example of the use of this timer in the present embodiment includes pump stroke charging and recharging.

The fourth timer is a one minute wake up timer and provides an interrupt every 60 seconds based on a 1 Hz input clock frequency. This counter provides two functions: (1) it provides the seconds portion for the time of day, and (2) it interrupts the CPU every 60 seconds. The principal purpose for the CPU writing into this timer is to adjust the software perception of the second number within a minute. The register for this timer does not hold the number to be counted to but instead holds the present count of the counter that continues to increment each second until a count of 60 is reached and then it starts over. Examples of the use of this timer in the present embodiment include counting elapsed minutes, performance of delivery calculations for pump strokes, determination of the present half hour, and one minute RF listening by the external communication device.

In the present embodiment a pump interface 926 is provided within the ASIC to allow appropriate control of the pump driving circuitry that is external to the ASIC. As noted above the implantable device of this embodiment includes an infusion pump that is used to selectively dispense insulin to a patient by utilization of a pulsatile pumping mechanism in combination with circuitry that (1) charges two capacitors to a voltage that is 5–6 times the battery voltage and (2) includes an activation switch that allows the charge on the capacitors to drain through the coil of the pumping mechanism. Different portions of the pump circuitry are controlled by each of the two processor ICs. As such, to effectively operate the pump, both processors must agree on appropriateness of pump activation. In particular, in this embodiment, one processor IC is responsible for charging the pump circuitry so that successful firing can occur, while the other processor is responsible for controlling the firing of the pump. In the implantable device the main processor has control over the charging function through use of a control register that includes a charge bit while the monitor processor has control of the pump activate function through a control register that includes an activate bit. Both processors are programmed to independently calculate when infusion should occur which in turn dictates when they should perform their separate functions.

Each processor has a three line interface that may be connected with the external pump driver circuit. However, in this embodiment, only part of the physical connections for this interface are supplied by each processor. There is a register that includes a power control bit to turn ON/OFF the pump power, a charge clock bit, and an activate/fire bit.

The external pump circuitry requires a clock signal to provide for charging a capacitor that is used to fire the pump. A clock is supplied for that purpose. The clock can be gated on and off via a control register to reduce power consumption when not needed and an interface is provided for tuning the frequency and duty cycle of the pump clock that is delivered off chip.

As pump charging efficiency is based in part on the frequency of the clock signal and possibly on the duty cycle of that signal, tuning ability is provided to allow enhancement of pump charging efficiency so as to reduce power consumption associated with charging the pump circuitry. A register is provided so that the software can control these parameters. In the present embodiment the pulse width is set at 4 $\mu$S. In the present embodiment the charging frequency is set at 64 kHz.

In the present embodiment one register bit is controllable to indicate whether RF reception is given priority over the charging of the pump circuit for noise considerations even though there may be some negative impact on power drain resulting from a need to partially recharge the pumping circuitry after a telemetry interruption. Toward this end, the pump clock itself is disabled whenever an RF receive power signal is asserted and the priority bit is set to give priority to RF reception. On the other hand, when this bit is oppositely set, by software, then the pump clock is allowed to remain on regardless of telemetry activity. As both telemetry operations and pumping operations are current intensive, it may be desirable to avoid both systems operating simultaneous so as to reduce maximum current drain on the battery at any given instant in time.

A watchdog monitor circuit 928 is provided to ensure that detection and system reset will occur if the CPU ceases to properly execute instructions. To achieve this, the watchdog monitor is configured to assert a system reset signal if an interrupt signal from the first wake-up timer occurs twice without the CPU properly servicing the watchdog monitor. In the present embodiment, the CPU resets the watchdog monitor by two writes into the watchdog monitor. Data for the first write has first pattern and data for the second write has a second pattern that is different from the first pattern. To ensure that the system is operating properly at both the interrupt level and the mainline code level, one of the two values is written by an interrupt routine while the other is written by the mainline code. Writes of values other than the first pattern followed by the second pattern will reset the sequence that the Watchdog is expecting. The reset signal generated by the watchdog is brought out of the ASIC and back to the external reset input of the ASIC.

Following a system reset or power-on reset, the watchdog monitor is not active. This allows the CPU time to perform initial configuration and housekeeping. The watchdog is activated, or enabled, as soon as the CPU writes any data pattern to a watchdog monitor register. Once enabled, the watchdog cannot be disabled until another CPU reset occurs. The ROM boot code activates the watchdog early on in its execution but sets the first wake up interval to a time sufficient for system configuration to occur. When the watchdog causes a reset, a piezo signal is put out so that an audio alarm will sound. This piezo signal remains on until the CPU re-activates the Watchdog.

The RF Module 930 in the processor IC consists of an (A.) RF timer circuit, (B.) a digital RF transmitter section that includes a QFAST® RF modulation transmitter, (C.) an analog receive module, (D.) a digital receive section that includes a QFAST® RF modulation receiver, and (E) a time synchronization section.

The RF timer circuit provides clock signals used by the other portions of the telemetry circuitry to provide a carrier signal for transmission, provide a signal for modulating the carrier, provide signals for demodulating received signals, and the like. The primary signal timer signal is pulled from the system clock generator module. The generation and shut of the primary RF timer signal is controllable by hardware or software based on values that are written into various registers which enable signal generation when needed and power savings when not needed. The time synchronization module ensures that the concept of time as held by the communication device and as held by the medical device are sufficiently close so as to enable RF communication to occur while maintaining transmission time and listening time of the RF hardware to a minimum. Further details on RF timing synchronization, autonomous and software activation and deactivation of telemetry hardware components are provided in the above referenced U.S. patent application Ser. No. 09/768,042.

The telemetry system provides a half-duplex link between the implantable device and the external communication device using a carrier frequency of about 250 kHz and a data signal having a frequency of about 8 kHz. The transmitter hardware uses the 8 kHz data signal to modulate the carrier signal to generate signals that will be transmitted by the antenna. The receive hardware receives the modulated signal and demodulates it to extract the 8 kHz data signal. Both the implantable device and the external communication device have transmit and receive capabilities to allow two-way communication.

Most of the RF telemetry circuits necessary for communication between the external communication device and the implantable device are implemented in the processor IC. In order to minimize the digital noise interference that the processor IC might impart to the weak RF signals that are being received, a high-gain RF amplifier is implemented off-chip. Also as discussed above, an RF antenna, that is used for both transmission and reception, and circuitry to select between reception and transmission are implemented off chip. The remaining analog sections and all the digital demodulation circuits are implemented in the processor IC.

The RF module of the Processor IC outputs transmission signals for transmission by the external antenna. It also provides a power signal to the external amplifier and an RF receive power control signal that is used to switch between a transmission configuration and a reception configuration. Both these signals are controllable by bit values placed into registers so that power consumption may be minimized when component operation is not required. The RF module also receives input signals from the external receiver hardware.

A Quadrature Fast Acquisition Spread Spectrum Technique (QFAST®) is used as the modulation technique. QFAST® modulation is based on an Offset Quadrature Phase Shift Keying (QPSK) modulation technique. In this technique, data generated by the CPU modulates clock signals at the carrier frequency. As a result of quadrature modulation, in-phase and quadrature-phase components of the given data stream are generated. These two components are then applied to opposite ends of the external antenna so that a combined signal is transmitted.

In QFAST®, data rate adaptability is accomplished through a spread-spectrum "coding gain" concept, with the spreading code being a simple clock. The modulation produced by the QFAST® modulator can be demodulated in a manner which delivers both clock and data. All of the QFAST® modulation and demodulation circuits are digital and are incorporated into the processor IC.

The QFAST® technique provides a communication system with the following attributes: (1) it extracts the clock from the received signal without a clock recovery loop; (2) it provides demodulation of data without phase ambiguity and without the requirement for synchronous demodulation; (3) it makes effective use of the available transmission bandwidth, (4) it results in fast acquisition of the message signal; (5) it is relatively immune to the effects of highly dispersive and distorting propagation media; (6) it does not require regeneration of a phase-coherent local replica at the receiver of the transmitted carrier; (7) it does not require resolution of ambiguity between the in-phase and quadrature-phase channels in the receiver; and (8) it does not exhibit data phase ambiguity.

The transmitter section of the telemetry system receives byte wide parallel data packets from the CPU and then loads the data into a parallel-to-serial shift register. The serial data is then sent to the QFAST® RF modulation transmitter section to modulate two quadrature clock signal components each operating with a carrier frequency of about $2^{18}$ Hz) and shifted in phase relative to each other by 90 degrees. The two components are then delivered to opposite ends of the antenna. As long as there is data in the transmitter parallel-to-serial shift register, the RF transmitter remains activated. If the transmitter doesn't have data available when the next byte is to be transmitted the message is considered to have been completely transmitted and the CPU shuts off the transmitter circuitry so as to minimize continued power drain.

External to the processor IC, the received RF signal is amplified by a high gain receive amplifier. A bandpass filter is used to attenuate out-of-band components such as those due to AM radio stations. The amplified RF signal then enters a mixer in the RF module of the processor IC and is converted to baseband using a two mixers, one in-phase mixer and one quadrature mixer both at the carrier frequency. The mixer outputs are the quadrature components of the baseband signals. An integrator & dump function in the RF module then removes the sum frequency (2 fc) and high frequency noise (i.e. acting as a low pass filter) from each of the two signal components. The processed signals are then digitized using a comparator and passed to the demodulator where the data and clock are recovered.

Further detail about QFAST® (Quadrature Fast Acquisition Spread Spectrum Technique) may be found in U.S. Pat. No. 5,559,828, entitled Transmitted Reference Spread Spectrum Communication Using a Single Carrier with Two Mutually Orthogonal Modulated Basis Vectors, by Armstrong, et al.

The ASIC also includes an interrupt handler 932. There are nine interrupt sources. All interrupts except one are maskable. The only non-maskable interrupt is generated by the memory decoder as a result of an invalid address detection. The interrupt handler module consists of a capture module for capturing interrupt conditions, a handling module, and a priority encoder module. Three of the nine interrupts may be used for external as well as internal interrupt sources, as for example by the external communication device.

The capture module is used to capture the occurrence of an interruptible event. This module contains two sets of registers: an enable control register (under CPU control), and (2) the capture register. The enable control register is bit mapped to each of the possible interrupt inputs. If the bit corresponding to an interrupt in this register is high the interrupt is enabled and can cause the interrupt signal to the CPU to be asserted. When enabled, an interrupt condition signal sets a bit in the capture register and a corresponding interrupt signal is asserted. The bits in the Capture Register are de-asserted only by a system reset or individually when a corresponding signal is asserted. The interrupt signals are passed to the interrupt processor module and combined with respect to priority to provide a single interrupt to the 8086 CPU delivered on the CPU's interrupt input line.

The handling module provides the necessary logic to accommodate the 8086 double interrupt acknowledge cycle as well as daisy chaining the interrupt signals to provide a priority for the highest level of interrupt in cases where multiple interrupts are pending simultaneously. When multiple interrupts are pending, the highest is serviced first. This is accomplished by asserting the output signal corresponding to the highest pending interrupt during the second CPU interrupt acknowledge cycle. This signal serves two purposes. First it is fed back to the capture module to clear the pending interrupt and second it is sent to the priority encoder module for encoding the interrupt vector.

Only one of the inputs to the priority encoder module is asserted at a time. This module encodes the interrupt level number of the asserted input and generates the appropriate interrupt vector value.

An analog-to-digital converter 934 (A/D) and associated signal multiplexer system are provided to sample analog signals. The analog signals for the implantable device include (1) battery voltage, and (2) the charge pump voltage. The analog multiplexer is used to select the analog input signal that is to be provided to the A/D. An amplifier is used following the MUX to provide signal conditioning for the input signals. Bits are provided in a control register for selecting the MUX channels, for enabling the MUX, for enabling the amplifier, enabling the analog to digital converter, providing a conversion status indication, providing a begin conversion signal, and for supplying a clock signal to the A/D converter.

The LCD Clock Driver consists of two input clocks (e.g. about 64 kHz (e.g. 216 Hz) and about 32 kHz (e.g. 215 Hz)), a MUX to select between them and a bit and an AND gate to gate the clock on and off.

The Processor IC has an alarm driver and interface 938 that offers direct control of a piezo buzzer alarm. The processor IC drives the alarm through a 2-wire interface. Software may be used to select one out of 128 frequencies ranging from about 64 Hz to about 8192 Hz. The tone duration and volume are also under software control. In the dual-processor implantable device, the monitor processor controls the buzzer. The piezo buzzer logic consists of a register, a counter, and compare functionality to provide a variable frequency to the piezo buzzer. The value in the register is compared to the value in the counter. Each time the values are equal the driving signal toggles to the next programmed signal. Additional logic circuitry is provided to allow volume control for the piezo buzzer. The outputs of each line are used externally as differential signals to the piezo buzzer. Thus with this scheme, the piezo can sound different frequencies and the volume of the piezo buzzer can be controlled.

After a processor IC reset, the piezo is driven at about 1024 Hz. This signal is gated with the output of a register bit that is under control of the CPU. The piezo signal is inhibited by this gate when the CPU writes into the watchdog enable register.

The Processor IC has two Synchronous Serial Interface (SSI) ports 944 and 942. Each interface provides full duplex serial communication ports that operate at about 500 kHz. One of these ports is used for inter-processor communication in the dual processor implantable device. In the external communication device, one port is used for IR based serial communications and the other is used as an interface for the LCD display panel. Each interface port supplies both data and clock. The clock driving the SSI may be enabled or disabled, thus controlling power consumption when the SSI is not needed. A control register is used to turn ON/OFF the SSI.

The RF communication between the implantable device and the external communication device occurs in the form of messages (sometimes referred to as communication signals or packets) that are passed back and forth between the two devices. In this embodiment these messages have a multi-part format or protocol: (1) preamble, (2) frame sync, (3) telemetry identifier, and (4) data.

For communications from the implantable device to the external communication device the preamble is a repeating pattern of "10", i.e. 10101010. This alternating pattern of ones and zeros is broadcast for 8-bit times. This pattern is considered the standard preamble pattern.

For communications from the external communication device to the implantable device, the preamble is either of the standard preamble pattern but applied for an extended number of bit times (e.g. 24, 48, or 96) or is of an attention preamble pattern that is applied for, typically, even a longer extended number of bit times. The attention preamble pattern is formed of a repeated pattern of "110110 . . . 110". In other embodiments, other attention preamble patterns may be used (e.g. repetitions of "011", "100", "001", "1011", and the like).

The preamble, whether of the standard pattern or the attention pattern, is used so that the RF reception hardware can establish bit synchronization (i.e. bit boundary recognition) of the incoming data. However, the attention preamble is further used to get and hold the receiver's attention for a defined period of time. As long as the attention preamble is being received, the receiver's hardware will stay on and continue tracking the signal in anticipation of an incoming message.

The attention preamble is considered to be lost, or no longer being received, when the receiver receives more than 2 inappropriate bit values during receipt of any 64-bits or when the frame sync pattern is received.

The attention preamble may be used when there is some uncertainty in the time synchronization of the two devices. The extra length of the attention preamble allows the receiver's reception window to open a little latter than anticipated and to still have the receiver pick up the entire message. The extra length of the attention preamble allows the receiver's reception window to open earlier than anticipated, so long as a minimum number of bits are heard by the receiver during the time its reception window is normally open, and still have the receiver's attention locked onto the preamble and have the receiver remain on as long as the attention preamble is being received, plus a little more, in anticipation of receiving a frame sync pattern.

In the present embodiment, frame sync may actually be considered byte sync (i.e. frames are bytes) and is a single byte of a selected pattern and is used so the receiver can obtain byte boundaries for the transmitted data. In the present embodiment, the selected pattern is "10110000.

This comparison process continues so long as the receiver continues to listen for an incoming message or until a valid frame sync pattern has been received. If the receiver is continuing to listen beyond its normal reception window (i.e. listening period), due to the reception of an attention preamble, the listening will not stop immediately upon the attention preamble being lost. The comparison process for ascertaining the receipt of frame sync continues for a number of bits after attention preamble is lost, even if the listening period has ended, as its loss may be associated with the partial receipt of frame sync. Once frame sync is received a valid frame sync signal is asserted.

In the present embodiment, the telemetry identifier (i.e. telemetry ID) is a 3-byte value that is used to ensure that only the intended receiver receives a message. The value of all "1 s" indicates a universal message that is to be received by all receivers, otherwise the telemetry ID must be agreed upon between the receiver and transmitter. A unique ID is provided for each implantable device and each external communication device during manufacturing. Only the external communication device can transmit a message using the universal ID code. The telemetry IDs that the receiver will consider to be valid are the ID of the receiver or the universal ID. All other incoming bit patterns will be rejected with the result that the receiver will be either turned off or will start again looking for a valid frame sync pattern attention preamble.

If a valid telemetry ID is received, the receiver listens to the remaining portion of the message.

In the present embodiment, data is provided in an integer number of bytes following the telemetry ID. In the present embodiment the first byte of the data indicates the message type. The first seven bits of the first byte is an operation code or op-code while the eighth bit is either ignored or is set and interpreted as a sequence number (to be discussed hereafter) dependent on whether or not the first seven bits call for a sequence number or not. Each op-code, based on its nature, is followed by data in a defined number of bytes. The specific op-code itself may dictate the number of bytes that follow or alternatively the specific op-code may dictate that the number of bytes to follow may be extracted from the first byte or several bytes of information that follow it. In alternative embodiments, op-codes may have a different length, or not be used at all, the message length or message end may be dictated in other ways. Based on the op-code and potentially one or more bytes following it, the receiver knows exactly how many more bytes of data to listen for. After receiving those bytes, the receiver may be turned off to conserve power.

For some messages dealing with drug delivery, the data portion of the message may include a bolus number. The bolus number is similar to the sequence number in that it is incremented by both the implantable device and external communication device under controlled conditions so as to reduce the possibility of bolus requests being delivered more than once when duplicate requests may be made as a result of the external communication device failing to receive a confirmation that a previous request was received. The bolus number may be a single bit number in some embodiments but in more preferred embodiments it is a multibit number (e.g. 2-bit, 4-bit, 7-bit, 1-byte, or 2-bytes) so that it can take on more than two values thereby making it less likely that an error will escape detection due to received and expected numbers erroneously matching. The incrementing of the bolus number may occur within the external communication device when it receives confirmation that a message was correctly received and it may be incremented by the implantable device when it correctly receives a bolus request. As such when a duplicate request for a bolus is received by the implantable device it can recognize that the expected and received bolus numbers do not match and that requested bolus is not a new request. As such the implantable device can respond to the repeated request that the bolus was correctly received and delivered (with out performing a second delivery and without incrementing its expectation of what the next bolus number will be).

In the present embodiment, the data portion of the message ends with a one or 2-byte validation or error checking code (its type is dictated by the op-code included with the message). The preferred error checking code of this embodiment is in the form of a cyclic redundancy code (CRC).

In the present embodiment, the telemetry system may loose bit synchronization if insufficient bit transitions are received per unit time (e.g. if more than about 100 to 120-bit times lapse without receiving a transition. In order to ensure that a sufficient number of bit transitions occur, the data portion of the message, with the exception of the op-code is randomized prior to transmission and is de-randomized upon receipt.

In order to keep power requirements low in a preferred implementation, the external communication device and implantable device attempt to maintain a common time base, transmissions are set to start at specified times, and reception windows are set for specified times and lengths. In this way, the receiver may remain in a powered down mode most of the time and can turn on to listen for a potential incoming message at the specified times for the specified lengths of time. If a message is found to be incoming, the receiver stays on, otherwise it goes back to sleep (i.e. power down mode).

In the present embodiment time synchronization for telemetry communication is maintained using two techniques. The first technique periodically determines the present difference in the concept of time (e.g. second boundaries) as held by the communication device and medical device and the difference is used to reestablish synchronization of the timers. In the present embodiment, reestablishment occurs on the part of the communication device each time it receives a valid communication from the medical device.

The second technique determines a rate of drift that has occurred between the concept of time held by the communication device and that of the medical device. The determined rate of drift is used in combination with a determined lapse in time to estimate how much drift has occurred. This amount of drift is then used in shifting a listening start time or transmission start time of a first one of the devices to match what is believed to be the potential transmission period or listening period of a second one of the devices.

In the present embodiment, software may be downloaded from the external communication device to the implantable device. The downloading of software may include the downloading of executable software as well as the downloading of data structures that may be used by the executable software.

In the present embodiment, a specific external communication device is configured/programmed to communicate substantively with only one specific implantable device, that is in turn configured/programmed to communicate substantively with only the same specific external communication device. An external communication device is capable of retaining the telemetry ID of exactly one implantable device at a time and an implantable device is capable of retaining the telemetry ID of exactly one external communication device at a time. A small amount of non-substantive communication (i.e. communication that does not impact insulin delivery) can occur between external communication devices and implantable devices that are not linked (i.e. partnered or married) to one another (i.e. provided with each others telemetry IDs).

In the present embodiment, many different types of messages and responses thereto can be written into the programs that control the implantable device and the external communication device according to the guidelines set forth above. These messages may be used for a number of different purposes. For example, (1) they may be system level messages that are used for testing devices, for resetting devices, or for establishing relationships between implantable devices and external communication devices, (2) they may be alarm messages that are used to convey alarm conditions or to clear alarm conditions, (3) they may be miscellaneous messages that set various parameters or perform various read operations, (4) they may be delivery messages that set delivery amounts, read delivery status, or set parameters such as concentration and pump stroke volume that may be required to appropriately control delivery of the drug, (5) they may be data log messages that set data log boundaries, read boundaries, or clear data logs, boundaries or read information from various data logs or supply information to those data logs, (5) they may be refill messages that are related to amounts of material that are added to the reservoir periodically, (7) they may be compound messages that perform more than one function, or (8) they may be error messages that request error condition status or supply error condition status.

Additional preferred features and aspects of a telemetry system are provided in previously the referenced U.S. patent applications Ser. Nos. 09/768,035, 09/768,042, and 09/768,207.

Two pieces of software may run in the implantable device at different times: (1) second stage bootloader software, and (2) application software. Upon reset, a boot program is executed by each processor IC from its internal ROM. This bootloader program in turns loads a second stage bootloader program into the RAM of each processor IC from the SEEPROMs that are attached to each, respectively. This second stage bootloader software is incapable of operating the insulin pumping mechanism, but is capable of performing limited telemetry and communication activity. One capability of the second stage bootloader software is to download new software from the external communication device. This download capability may be used to download new second stage bootloader software or it may be used to download new application software. The second stage bootloader software remains the active software controlling the implantable device, until a valid copy of new application software is downloaded and executed. At the time that the new application software is executed, the second stage bootloader software relinquishes control of the implantable device. The application software is the software that is capable of controlling the insulin pump as well as receiving command instructions from the external communication device concerning insulin delivery. The implantable device, when running in application mode (i.e. running the application software), ignores messages related to software downloading as these functions are not supported by the application software.

A second stage bootloader program is provided for both the main and monitor processor ICs. The SEEPROM for each of the monitor processor and the main processor contains it own unique second stage bootloader software (SSBS). This software serves three primary purposes: (1) It places the medical device in a safe state where medical operations are inhibited, (2) It enables the implantable device to receive new or replacement application software via telemetry from the external communication device while the implantable device is in a non-medically active state (i.e. a safe state), and (3) It allows the system to reset itself, after the occurrence of system failure of some type, so that the implantable device may be placed in a state that allows communication with the external communication device but does not allow or even support the medical functionality of the system (i.e. the dispensing of insulin in this embodiment).

In alternative embodiments, medical operations may not be completely eliminated when the bootloader program is in control of the medical device, but instead they may be curtailed to a limited set of operations. This limited set of operations may be implemented via the CPU and based on simplified software operations, or based on hardcoded instructions, or even implemented via circuitry that functions entirely or almost entirely independent of the processor. In the independent circuitry implementation the processor may retain the ability to shut off power to the independent circuitry when application software is properly controlling the device. For example, the minimal functionality maintained may involve the ability of an infusion pump to deliver a minimal amount of drug per hour so as to reduce the risk of catheter blockages that otherwise might form. In another example, a pacemaker device might be limited to a fixed, minimum, and independently implemented pulsing rate. In a further example, physiological monitoring activities may be allowed to continue but may not be allowed to directly control closed loop infusion operations, closed loop stimulation activities, or the like, but may be allowed to produce warnings to the patient so further analysis and actions may be taken if a serious condition exist.

After power-up, both the main and monitor processors in the implantable device immediately begin executing the ROM code. The execution of this ROM code places the pump hardware in a safe state, then looks for a SEEPROM attached to the respective processor IC. The code resident in the SEEPROM is then loaded into memory and executed so that control of each processor is handed over from the ROM code to the second stage bootloader code. For the device to become medically active, new application software must be downloaded from the external communication device as any previously held versions of the application code have been removed upon system reset or became inactive upon system reset. In alternative embodiments, in certain circumstances, re-execution of previously loaded software may be acceptable. For example, if previously loaded software were held in non-volatile memory such as a SEEPROM, as is the bootloader software, that software may be reloaded into RAM from the SEEPROM.

In the present embodiment, the main processor is used to manage and control telemetry communications with the external communication device while communications between the main and monitor processors (inter-processor, or IP communications) are handled using the SSI-A port of each processor IC. To save power, each processor turns off the clock used by its SSI-A port when the port is not in the process or transmitting or receiving a message.

In the preferred embodiment, reset of a processor IC is made to occur by triggering the watchdog for that processor. The triggering of the watchdog may occur by self-detection of an error in the system or by receipt of a reset command by the processor. The Watchdog for each processor IC is set by software to be serviced at both interrupt and mainline level by the processor IC's CPU. This dual level servicing prevents permanent malfunction of the system that might otherwise result from the masking of interrupts at mainline level and infinite loops at either mainline or interrupt level. When the second stage bootloader software is running, the watchdog for each processor IC is initialized with a long time-out period (e.g. several minutes). When certain errors occur, the system is made to reset by the software entering an infinite loop that will cause the watchdog to trip within a short time (e.g. 1 second). However, before entering the infinite loop, the software is made to write a unique two-byte complementary code to a selected location in internal RAM. The complementary code is indicative of the error that has caused the reset. Saving this information to the selected location in internal RAM is acceptable, as internal RAM is not cleared upon normal reset. A two byte complementary code is used as opposed to a one byte code so as to give enhanced confidence that the correct reason for system reset is being noted. An example of this is a reset that results from the occurrence of a NMI. The programming of the NMI Interrupt vector causes the interrupt service routine to write a 2-byte complementary code to a selected location of external SRAM which is indicative that an NMI occurred. The service routine then sets the value in the wakeup one timer to zero and loops at. the same address until reset is triggered.

The main processor SSBS tracks and increments the values held in several counters: (1) it adds the number of bytes of each transmitted telemetry message to a lifetime total telemetry transmit bytes counter that is held at a fixed location in internal RAM; (2) it increments a counter each time, it is initialized in the main processor; and (3) it increments a running relative time counter based on interrupts from the one-minute wake up timer such that it contains a total number of minutes from factory initialization. The first and third of these counters are updated by the application software running on the main processor as well.

The main processor SSBS programs a value into a particular register so that the concept of "second" time for the RF system and for the wake up one second timer are identical. In the implantable device this value remains fixed. In the external communication device this value changes based on an anticipated amount of drift between concepts of time held by the two devices. This value is used to cause telemetry reception (i.e. listening) or telemetry transmission to shift its start time relative to the device's concept of time so as to track the potential transmission time or listening time of the other device when drift is believed to have occurred. Further detail about time synchronization between the two devices is provided in previously reference U.S. patent application Ser. No. 09/768,042.

The second stage bootloader software during system initialization writes various constants to selected locations in internal RAM: (1) a pulse stealer calibration value, (2) the medical device telemetry ID, (3) a constant defining the pump converter configuration, and (4) various RF constants. As at least a portion of these parameters are used by both the SSBS and the application software, the locations where this data, as well as some other data, is loaded is sometimes call the shared bootloader region or the reserved bootloader region.

In the present embodiment, the stack for the bootloader builds down from the top of Internal RAM (e.g. from 0x3FFF), or from a somewhat lower location defined by the stack pointer (e.g. somewhere between 0x3FFF and 0x3F00) to the bottom of the memory defined by the segment (i.e. offset=0, e.g. 0x3F00). As the stack is addressed by use of a 16-bit offset only, and not a segment value, the stack may build down only to the bottom of the offset. If however, the stack attempts to build down beyond the offset zero value, the offset address is rolled over to 0xFFFF but as the segment value is not changed, the address that the pointer is directed to is not the next address below 0x3F00 but is instead a higher address defined by the rolled over offset value plus the segment address (e.g. Offset FFFF+Segment 3F05=0x13EFF). If this new address is not within a valid memory space or if the memory decoder is configured to recognize this memory location as a problem (e.g. produce a NMI when an invalid memory space is addressed), knowledge that a stack overload has occurred may be obtained. Since in the present embodiment, a NMI triggers a reset of the system, the possibility of a stack overflow causing a corruption of system operation in some potentially unpredictable, unsafe, and/or unrecoverable manner is avoided.

This process solves the problems that may be associated with unrecognized stack overflow problems by forcing the system into a known safe and recoverable state when an overflow occurs. The process involves positioning a stack pointer to a desired location above a base pointer (to define the desired stack size), locating an invalid memory region, or otherwise recognizable memory location, above the stack and causing the memory address to jump into the invalid memory space in the event that the stack pointer ever decrements below the base pointer value, and using a memory decoder or the like to identify that an invalid memory location (e.g. produce an NMI), or otherwise recognizable location, has been called and then issuing an appropriate interrupt and interrupt vector routine to place the system in the safe and recoverable state (e.g. force the system to reset)

The software configures the hardware to listen for incoming messages every two seconds on even second boundaries. Each outbound telemetry packet is programmed to be transmitted with 1 byte of preamble of the normal pattern and 1 byte of frame-synch (these same parameters are used by the application software as well). The software allows actions on received telemetry messages, such as copying data from a packet or initiating an internal operation, to occur only if the messages can be appropriately validated. Validation includes matching transmitted CRCs to derived CRCs, and matching transmitted sequence numbers with a current sequence number in the implantable device. If the CRCs match, a response packet is always returned regardless of the sequence number. Once a packet has been received with the sequence number matching the sequence number of the implantable device, the sequence number of the implantable device is complemented. The sequence number transmitted is not updated by the communication device until it receives an acknowledgment that the message was correctly received by the implantable device. This required matching of sequence numbers results in duplicate messages (repeated because the communication device did not get a response to the prior message(s)) being acted upon only once by the medical device.

The SSBS ignores all telemetry messages related to drug delivery but recognizes and processes messages related to system level operations: (1) RESET—reset requests (from a linked communication device), (2) INTEROGATE—interrogation inquires made as the first step in specifically linking the medical device to a particular communication device, (3) LINK—link requests made as the second and final step in linking or marrying the two devices, (4) SYNC—synchronization requests that are used to re-establish a common time base between the two devices, (5) LOAD START, LOAD CONTINUE, AND BOOT—messages related to downloading new software and booting (i.e. executing) that software, and (6) READ—read requests of designated portions of internal memory that are used primarily for diagnostic purposes. Further details concerning these messages may be found in previously referenced U.S. patent application Ser. No. 09/768,035.

Each inter-processor (IP) message sent by the main processor to the monitor processor requires a corresponding response message from the monitor processor with the exception of the reset IP message. The main processor will not send another message until a response message is received. Through software, the main processor initiates a time-out period (e.g. of about 500 ms to about 1000 ms). If a response message is not received before this time-out period elapses, the shared bootloader region is written with a 2-byte complementary code indicative of a failed inter-processor communication. Once this 2-byte complementary code has been written, the wakeup one timer for the main processor is programmed with a zero and program execution continues to execute the same address, tripping the Watchdog within a short period of time.

The main processor supports a number of IP messages while executing second stage bootloader software. These messages are related to the telemetry messages, noted above, that are supported by the main processor. (1) RESET—causes reset of the monitor processor, (2) BOOT—causes the monitor processor to execute newly downloaded code, (3) Read Memory—causes the monitor process to supply back the contents of the designated portions of memory, (4) LOAD START—prepares the monitor processor for accepting and appropriately loading new software, and (5) LOAD CONTINUE—supplies the monitor with image portions of the new software. Each of these messages supplies either an acknowledgment response back to the main processor and any other requested information. The main processor in response to the IP messages prepares and sends appropriate acknowledgments to the communication device via telemetry.

The SSBS is loaded into a predefined exclusive portion of the internal RAM. As did the, main processor, the monitor processor writes various constants to selected locations in internal RAM. Unlike the main processor none of the constants stored pertain to telemetry parameters, pump control parameters but instead pertain to piezo alarm parameters. The parameters include: (1) a pulse stealer calibration value, (2) a single beep frequency value for use with all bootloader alarm tones, (3) a single beep duration value for use with all bootloader alarm tones, and (4) a time value indicating an interval between beeps for bootloader alarms.

The software running in the monitor processor controls sends alarm signals to the piezo alarm buzzer included in implantable device. The software causes five alarm tones of the frequency, duration, and spacing specified by the above noted constants to occur on the first one-minute interval following system reset and each subsequent 8-hour interval that the monitor processor continues to execute second stage bootloader software.

Upon download of the application software, it is loaded into internal RAM by the SSBS. This direct loading into internal RAM reduces current usage compared to what would be used by loading the software into external RAM and then later loading it into internal RAM. All data logs are retained in external RAM. During the download the application code does load over any SSBS reserved memory space in internal RAM.

Blocks of memory are reserved for holding various types of data that are used by both SSBS and application software: (1) factory programmed constants used by the implantable medical device, (2) a code indicating a reason for a last system reset, (3) CRC values for program images, (4) One minute system clock value The constants stored in the shared memory region are originally extracted from the SEEPROM and include: (1) pump charge time—used as the initial pump charge time at system startup, (2) A/D counts for target charge voltage—calibrated value for the charge voltage required to fire the pump. (3) maximum charge time—time measured in approximately milliseconds (1/1024 seconds) that will generate an error if the pump takes longer than this time to charge including any time gaps due to telemetry transmission and reception, (4) A/D counts for post-fire voltage—calibrated value for the highest voltage allowed on the charge capacitors following firing of the pump that does not result in a pump firing error, (5) stroke volume—estimated volume of drug delivered per stroke of the piston, (6) A/D counts for low battery—value for the loaded battery voltage reading that indicates a low battery condition, (7) A/D counts for dead battery—value for the loaded battery voltage reading that indicates a dead battery condition, and (8) loaded battery transmission time—the number of bytes to send using telemetry transmission for a loaded battery measurement.

The software is configured to service the Watchdog in the same manner as noted above with regard to the Second Stage Bootloader Software.

When there is no CPU processing required, the software turns off the CPU to enter sleep mode by turning off the CPU clock after setting appropriate wake up conditions. This mode results in minimal current drain from the CPU.

When there is no inter-processor communication active, the software running in each processor IC turns off the clock to SSI-A to conserve power.

The main processor and the software running thereon are responsible for maintaining system timers, performing telemetry reception and transmission, performing pump stroke calculations, implementing charging of the pump hardware, performing A/D measurements on the battery and the capacitor voltage for the pump charging circuit, logging of diagnostic data and alarm conditions, initiation of self-testing, and communicating with the monitor processor.

The software continues to increment the one-minute time counter as was done by the SSBS and uses the information therein for logging event times and telemetry transmission activities. The software also maintains a half-hour counter which is incremented each half-hour period and which starts at midnight with a value of zero. The software also maintains a counter that contains the number of minutes within the current half-hour period.

The main processor application software performs pump stroke calculations based on programmed values, received from the external communication device for delivery mode, basal rate, phase-1 (immediate) bolus amount, and phase-2 bolus rate and duration. The delivery mode influences which of these other values (if any) are used. If normal delivery mode is programmed, the basal rate is a value derived from a table which contains rates in pump strokes/minute for each half-hour period of the day, unless a temporary basal rate has been programmed, in which case the temporary basal rate is used. Phase-1 bolus amount specifies the portion of a bolus that is delivered as rapidly as possible when the user programs a bolus. The phase-2 bolus rate is a delivery rate used for the duration specified by the user/patient. If a phase-2 bolus rate is programmed, it is delivered in addition to any basal rate that is also programmed.

Due to various error conditions, the software may be placed in a no delivery state or stop mode. In the no delivery state, no insulin is delivered. Due to various other error conditions, the software may place the pump in a minimum delivery state or suspend mode. In the minimum delivery state a medically insignificant amount of insulin is delivered (e.g. one basal pump stroke per hour).

The main processor software maintains an accumulator for basal pump strokes which is used when the pump is not in no delivery state. In the present embodiment, the basal pump stroke accumulator contains 5 bits for the whole part of basal pump strokes and 11 bits for the fractional part of basal pump strokes. Each minute, the quantity of insulin programmed for delivery in that minute is added to the accumulator, any whole number of pump strokes indicated in the accumulator are delivered in that minute and the accumulator is decremented by "1" with each pump stroke that is delivered.

The software maintains a basal profile table that contains a single entry for each half-hour of the day, which indicates the number of pump strokes per minute to deliver during the corresponding half-hour period. The entries in this table are in the same format as used by the basal pump stroke accumulator described above. A current profile pointer is maintained which points to the basal rate in the basal profile table used for the current half-hour. When a half-hour boundary occurs, the pointer is incremented to the entry for the new half-hour and the new entry is used for pump stroke calculations during each minute of the new half-hour. If a new time is programmed into the implantable device from the external communication device, the pointer is positioned to a new entry. The half hour indicator may be directed to a new half-hour if a change is received from the external communication device and a minute value may change as well which will dictate when the next half-hour interval will occur.

A current basal rate value is maintained which is the value in basal profile table indexed by the current profile pointer, if there is not a temporary basal rate in progress. Otherwise, the current basal rate value is the value for the temporary basal rate.

The main processor software also maintains an independent accumulator for phase-1 bolus (immediate bolus) pump strokes, which holds only integer numbers of pump strokes and which is initialized when a valid deliver bolus telemetry message is received.

The main processor software maintains an accumulator for phase-2 bolus pump strokes. At the beginning of each minute, the main processor software adds the number of pump strokes to be delivered that minute (based on the quantity of insulin programmed for delivery) to the accumulator, any whole number of pump strokes indicated in the accumulator are delivered in that minute and the accumulator is decremented by "1" with each pump stroke that is delivered. If any pump strokes are not delivered during that minute, for example due other delivery priorities, they remain in the accumulator and are delivered during the subsequent minute or minutes. The phase-2 pump stroke accumulator contains 5 bits for the whole part of bolus phase-2 pump strokes and 11 bits for the fractional part of bolus phase-2 pump strokes.

When the pump is placed in the no delivery state, the software sets the accumulator for basal pump strokes, phase-1 bolus pump strokes, and phase-2 bolus pump strokes to zero and any diagnostic rate or priming bolus is canceled. When in the no delivery state, no pump strokes are delivered. When the pump is placed in a minimum delivery state, the software places the whole portion (upper 5 bits) of the accumulator for basal pump strokes, phase-1 bolus pump strokes and phase-2 bolus pump strokes to zero. While in the no delivery state mode, pump strokes are delivered at a rate of one pump stroke per hour. In some respects the no delivery state is like stop mode in that insulin delivery is prohibit in both. However, as stop mode is entered at the user's choice, it may likewise be exited at the user's choice but as the no delivery state is entered due to a system error, it may not be as readily dismissed. The minimum delivery state is also somewhat different from suspend mode even though both set the system at the delivery level. As the minimum delivery state is entered as a result of user inaction and not necessarily as a result of a conscious decision made by the user, the entry is considered an alarmable event.

The software in the implantable device supports the following delivery modes: shelf mode, normal mode, suspend mode, stop mode, diagnostic rate mode, and priming bolus mode.

Shelf mode, or storage mode, is a mode where the device is substantially inactive. It is generally used when the device is in storage prior to implantation. As a quick response time to telemetry communications is not a requirement, the telemetry reception interval is set to a large value so as to minimize power consumption (e.g. 10–20 seconds or more). Except for enabling telemetry reception all other modules are shut down or otherwise put into a power savings mode and as such no delivery occurs while in this mode.

When the implantable device is in normal mode, basal pump strokes utilizing the basal profile table, basal pump strokes utilizing the temporary basal rate, and bolus pump strokes are supported.

When the pump is placed in stop mode, the software sets the accumulator for basal pump strokes, phase-1 bolus pump strokes, and phase-2 bolus pump strokes to zero and any diagnostic rate or priming bolus is canceled. When in stop mode, no pump strokes are delivered. When the pump is placed in suspend mode, the software places the whole portion (upper 5 bits) of the accumulator for basal pump strokes, phase-1 bolus pump strokes and phase-2 bolus pump strokes to zero. While in suspend mode suspend mode, pump strokes are delivered at a rate of one pump stroke per hour. 6-064 When the implantable device is placed in Diagnostic Rate Mode, pump strokes are delivered at the rate specified by the Diagnostic Rate.

When the implantable device is placed in priming bolus mode, phase-1 bolus pump strokes are set to the amount specified by the priming bolus amount. When the phase-1 bolus pump strokes reach a value of zero, the software places the implantable device in normal mode.

When the temporary basal rate duration is non-zero, the temporary basal rate in terms of pump strokes per minute is added each minute to the basal pump stroke accumulator instead of the value indicated in the basal profile table as indexed by the current profile pointer. When the temporary basal rate duration is non-zero, pump strokes are delivered when the accumulator value has a non-zero whole portion. As each pump stroke is delivered the value in the accumulator is decremented by "1". When the implantable device is placed in suspend mode, software continues to decrement any active temporary basal duration but does not add additional amounts to the accumulator each minute. If the temporary basal rate duration is not zero when the system returns to normal mode, the temporary basal rate amount is added to the accumulator each minute and deliver continues as dictated by the accumulator for any remaining potion of the duration. When the implantable device is placed in stop mode or is in no delivery state or minimum delivery state, the temporary basal duration is set to zero.

Pump strokes for the immediate bolus amount are delivered immediately (i.e. as quickly as possible, preferably no more than a few second delay between each for charging the pump circuitry). These pump strokes are delivered prior to delivery of phase-2 bolus pump strokes which are delivered prior to basal pump strokes. Pumping continues without more than a few second delay between each firings of the pump and beginning the next charge cycle, until the immediate bolus amount is delivered, and the whole portions of the pump stroke accumulators for Phase-2 Bolus and basal rate are zero.

The software maintains variables several variables related to amounts delivered: (1) total phase1 amount delivered for previous bolus, (2) total phase2 amount delivered for previous bolus, (3) duration for previous phase-2 bolus, (4) basal daily total for pump strokes delivered thus far during the day, (5) bolus daily total for pump strokes delivered thus far during the day, (6) yesterday's basal total, and (7) yesterday's bolus total. At midnight, the basal daily total is copied to yesterdays basal total and then zeroed out, and the bolus daily total is copied to yesterdays bolus total and then zeroed out.

The software also increments a lifetime total delivered counter by adding one into it every time a pump stroke is delivered.

A number of pump strokes remaining variable is decremented with each pump stroke (if not already at zero). If a low reservoir event is not already asserted, the software compares the value of this variable to a predefined low reservoir threshold value. This comparison is made once per day and a low reservoir event is asserted if the number of pump strokes remaining is not greater than the threshold. If a low reservoir event is already asserted and an empty reservoir event is not already asserted, this value is compared to a predefined empty reservoir threshold once per day and an empty reservoir event is asserted if the number of pump strokes remaining is not greater than the threshold. When assertion of the empty reservoir event occurs, pump activity may be limited for example by eliminating the ability to deliver boluses, or by switching the pump to suspend mode. In still other embodiments, pump activity be maintained in its fully functional capacity and warnings given to the patient to ensure that special attention be given to blood glucose levels as insulin delivery may not be the amounts desired The software running on the main processor initially sets a pump charge time variable equal to a predefined value copied into the shared memory region (i.e. pump charge time). This charge time is maintained with a resolution of 1 millisecond. When preparing to activate the pump, the software causes application of power to the pump charging circuit for the amount time indicated by the pump charge time variable. Once this time has lapsed, the pump charging circuit is shut off and an A/D reading is performed on the capacitor. If the capacitor voltage reading is greater than a predefined value for target charge voltage (i.e. AND counts for target charge voltage) plus a predefined upper boundary amount (e.g. 8 millivolts), the pump charge time variable is decremented by a predefined decrement amount (e.g. 1 millisecond).

If the capacitor voltage reading is less than the value of the target charge voltage, the pump charge time variable is incremented by a predefined increment amount (e.g. 1 ms). Thereafter, charging is re-initiated for an additional predefined time (e.g. 5–15 milliseconds) as defined by a recharge time parameter. Once the recharge interval has elapsed, an A/D reading is again performed on the capacitor. If the capacitor voltage reading is still below the target charge voltage, charging is again re-initiated for an additional amount of time as specified by the recharge time parameter. This recharging, measurement, evaluation cycle is repeated until the Target Charge Voltage is reached, or until a predefined maximum charge time is reached. In this embodiment, all recharge times use the same recharge period as defined by the recharge time parameter and the use of recharge cycles are not used to adjust the pump charge time. If the maximum charge time is reached, (e.g. 4 seconds), a charge time too long event is asserted.

Once the target charge voltage is reached, a fire pump message is transmitted from the main processor to the monitor processor. Once the fire pump message has been sent to the monitor processor, the software on the main processor initiates the timing of a predefined fire time delay, e.g. 50–100 milliseconds and then sends the monitor processor an unfire pump IP message. The software on the main processor then initiates an A/D reading of the pump charge capacitor voltage. If the capacitor voltage reading is above a predefined amount (i.e. A/D counts for post-fire voltage), a post-charge voltage too high event is asserted.

Telemetry communications occur using various messages and the format discussed above. When the first byte (starting with the Op-Code) of an inbound telemetry message is received by the implantable device, the software rejects the message if the op code is outside the allowed range or is an op code for an outbound packet. If the message is rejected, the receive hardware is shutdown until the next reception window opens. No response to the message is sent when the op-code is invalid.

If an alarm condition exists, and the implantable device receives a telemetry message that is not a sync, interrogate, link, or clear alarm message, the implantable device returns an error message.

Any actions, such as copying data from a message or initiating an internal operation, will not occur if the sequence number embedded in the inbound packet does not match the current sequence number in the implantable device. A response packet is returned regardless of the sequence number. Once a packet has been received with the sequence number matching the sequence number of the implantable device, any action requested by the message is taken (assuming any other validation criteria are met), a response is sent back to the external communication device using the sequence number, and the sequence number of the implantable device is complemented.

On the first complete telemetry transmission of a given day or on the first one-minute, one-second boundary of the next day, if given day had no telemetry transmission and the device is not in shelf mode, the software institutes, or continues, telemetry transmission for a minimum number of bytes as specified by a predefined loaded battery transmission time parameter. During transmission of the last byte of this message, an A/D Battery Measurement is performed and stored in a loaded battery voltage variable.

For each valid message received that is of a type that requires a response, the software prepares an appropriate response. The form of the response message is dictated by the message received and the established protocol.

If the response message being returned contains time sensitive information and the request is received within a particular period (e.g. within 125 mS) before the next second, the transmission of the response is delayed for a full second until the subsequent second boundary at which time the new current second value is placed in the response message and the message is sent. This delay in sending a response ensures that the communication device gets it and processes before a current second rolls into a next second which could otherwise result in a time discrepancy between the two devices.

If the RF message received by the main processor requires information from the monitor processor or presents information required by the monitor processor, the main processor prepares an IP message that it sends to the monitor processor. The monitor processor then prepares and sends an ACK IP response message for passage back to the main processor or it prepares and sends a more detailed IP response message as required. Upon receipt of the monitor processor's IP response message, the main processor prepares an RF response message as appropriate and transmits it to the communication device.

The main processor software logs the occurrence of each predefined event into an event data log. The reassertion of these event conditions is also recorded in the log. The main processor software provides event notifications for reservoir level and battery level at noon each day., unless prior telemetry activity for other reasons results in the transmission of an error telemetry message that contains the event information. The main processor software will also set a 24-hour internal alarm time-out that will be initiated at noon of the next day if the alarm has not been cleared and there is not an alarm already in progress as there is no need to provide additional alarm tones if an alarm is already sounding. The user may suppress the alarming of these events by acknowledging them; however, if the event is not cleared in seven days they will be reasserted. Though these two event conditions have independent reassertion times, the main processor software may reassert both of them on the same day at noon.

Internal alarm time-out is initiated when an error, i.e. error or alarmable event, is detected. For errors, i.e. events, related to reservoir level and battery level a time-out for communicating the error to the patient does not occur until noon; when, if the error has not already been cleared, an alarm on IP message is prepared by the main processor software and sent to the monitor processor for assertion by sounding the internal buzzer.

Reassertive alarms for reservoir level are cleared by the main processor software when a telemetry message for refill is received. The main processor software provides no mechanism for clearing the reassertive alarm condition resulting from either a low or dead battery.

If an error is present, an error transmission is initiated by the main processor software on the one-minute boundary for each of 3 minutes following detection of the error, unless the error is cleared using a clear alarm conditions message.

The main processor software provides a no delivery condition and telemetry error notification on the next one-minute, one-second boundary after occurrence of several events: (1) inter-processor communication time-out from main processor to monitor processor, (2) pump charge time too long, (3) post fire voltage too high, (4) over-delivery error reported by monitor processor, (5) under-delivery error reported by monitor processor, and (6) dead battery. An over delivery error occurs when the main processor requests firing of the pump when the monitor processor determines that delivery is inappropriate. Conversely, an under delivery error occurs when the main processor fails to request delivery when the monitor processor has determined that a delivery is appropriate.

When a no delivery error occurs the main processor software sets delivery mode to stop mode. A no delivery error occurs when post fire voltage is too high. The main processor software also causes the bit related to the no delivery error to be OR'd into a no delivery alarm conditions variable bit field.

When a read alarm conditions telemetry message is received, the main processor software performs the OR operation between the no delivery alarm conditions variable bit field with the alarm conditions variable bit field and prepares a response packet that returns alarm condition variable bit field as the error field of the response packet.

When a delivery related telemetry message (set basal rate, set temp basal rate, deliver bolus, set delivery mode, set insulin concentration) is received, and if any bit is set in the no delivery alarm conditions variable, the main processor software performs an OR operation between the no delivery alarm conditions variable and the alarm conditions variable and returns an error telemetry message. As such when a no delivery state is in force, the response to a delivery request is not an acknowledgment of that request but instead is an error message thereby warning the patient of a problem with the pump.

The main processor software institutes a 5-minute delay on the internal alarm for each of the above errors with the exception of an inter-processor communication time-out from main processor to monitor processor. After five minutes, the main processor software produces an inter-processor delivery error message for each of these events with the exception of the inter-processor communication time-out from main processor to monitor processor event.

Each day at midnight the main processor software compares the loaded battery voltage to the A/D counts for dead battery, and asserts the dead battery event if the loaded battery voltage is less than or equal to the A/D counts for dead battery.

The main processor software provides a minimum delivery condition and telemetry error notification on the next one-minute, one-second boundary and a 5-minute delay on internal alarm for the auto off interval exceeded event. If the automatic off interval is non-zero, the main processor software sets a timer to the automatic off interval and decrements the timer each minute. If this timer is decremented to zero, the main processor software asserts an auto off interval exceeded event. The main processor software also resets the timer to the predefined automatic off interval each time a valid telemetry packet is received with the exception of an interrogate telemetry message. The event also triggers the main processor software to prepare an inter-processor delivery error message.

The main processor software provides for error notification at noon for several events unless telemetry activity results in the clearing of the alarm prior to that: (1) low reservoir, (2) empty reservoir, and (3) low battery. Each of these events causes a 24-hour internal alarm time-out following attempted noon error notification.

Each day at midnight the main processor software compares the loaded battery voltage to the A/D counts for low battery, and the low battery event is reported if the loaded battery voltage is less than or equal to the A/D counts for low battery on two consecutive days.

The main processor software provides most events with time-stamps in the event data log: (1) normal delivery mode initiated, (2) stop delivery mode initiated, (3) suspend delivery mode initiated, (4) diagnostic rate delivery mode initiated, (5) priming bolus delivery mode initiated, and (6) insulin concentration change. These events are stored in the event data log and no other actions are taken.

The main processor software provides for the sounding of internal alarms by initiating inter-processor alarm messages. When all alarm conditions have been cleared by the clear alarm conditions telemetry Message, the internal alarm is turned off by sending the alarm off inter-processor message to the monitor processor When a set current time message is received the main processor software processes the messages and estimates whether change in time is for a new day, the same day or the previous day. In other embodiments, a date change indicator could also be passed with the time change information to remove any ambiguity. In the present embodiment however, if the new hour (based on a 24 hour clock) indicated by the set current time telemetry message is less than the current hour of the implantable device, and the new hour subtracted from the current hour is >=12, the main processor software concludes that time has shifted forward into the next day. If the new hour indicated by the set current time telemetry message is greater than the current hour of the implantable device, and the current hour subtracted from the new hour is >=12, the main processor software concludes that time has shifted back to the previous day. If a set current time telemetry message changes the time to the next day, the daily total log is written to and midnight self-test functions are executed. If a set current time telemetry message changes the time to the previous day, the daily total data log pointer is decremented to point to the previous day and the current basal daily total and bolus daily total are added to the values from the previous day's values.

The implantable device maintains a bolus history log and the main processor software adds data to the log with the delivery of each bolus. The main processor software records entries in the log that consist of the time of the start of the bolus represented by the running relative time counter value at the beginning of the bolus, followed by the total phase1 delivered for previous bolus and total phase2 delivery for previous bolus.

The implantable device maintains a battery voltage log and the main processor software adds data to the log each day. The main processor software records entries to the log that consist of an unloaded battery voltage and the loaded battery voltage. The main processor software writes these values to the battery voltage log at the next available location each day at midnight. The software is configured to perform a daily unloaded battery voltage test at a time when minimal pump activity is expected (e.g. at midnight). During this measurement, software inhibits initiation of pump charging.

The implantable device maintains refill log and the main processor software adds data to this log when refill activities occur. The main processor software records entries to the log that consist of the current time as represented by the running relative time counter (one minute counter), the refill amount as provided via telemetry from the communication device, and the number of pump strokes remaining prior to being modified by a new refill amount that is received via telemetry from the communication device.

The implantable device maintains an event data log and the main processor software provides data to the log as predefined events occur. The main processor software records entries to this log based on the running relative time counter value at the time of the event, followed by a code that represents the event type.

The main processor software is capable of initiating self-test functions. These functions may be initiated by request via telemetry from the communication device or periodically on an automated basis, e.g. each day at midnight. When initiated an alarm tone sequence occurs. The main processor software sends a self-test IP message to the monitor processor. As part of the self-test the main processor software calculates the program image CRC for each program image residing in the main processor memory and compares the results to the respective program image CRCs residing in the bootloader reserved area. If a calculated program memory CRC does not match the bootloader reserved area CRC value for the program image, the main processor software masks interrupts and the shared bootloader region is written with a 2-byte complementary code which defines a program memory CRC error. Once this value has been written, the main processor software causes the Watchdog to be tripped. The main processor software maintains a flag indicating whether self-test functions are currently in progress. The monitor processor performs similar function in response to the self-test IP message.

The main processor and monitor processor communicate with each other through inter-processor messages that are sent and received through the SSI-A port. The main processor software requires that a corresponding ACK message be returned from the monitor processor to the main processor for each inter-processor (IP) message sent by the main processor to the monitor processor. The main processor software will not send another message to the monitor processor until an ACK message is received. The main processor software starts a time-out period when the IP message is sent. The time-out period is set for a predefined amount of time (e.g. about 800–1000 ms). If an ACK message is not received before this time-out period elapses, an error condition is reported.

Each inter-processor (IP) message sent by the monitor processor requires a corresponding ACK message from the main processor that it received the message. The monitor processor will not send another message until an ACK message is received. A time-out period of a predefined amount (e.g. about 800–1000 ms) is set by the monitor processor software when the message is sent. If an ACK message is not received before this time-out period elapses, the monitor processor software writes a 2-byte complementary code to the shared bootloader region, then causes the watchdog to be tripped.

When the monitor processor receives the first byte of an IP message, the monitor processor software checks the op code against possible message types. If the message type is invalid, the monitor processor software writes a 2-byte complementary code to the shared bootloader region. Once this value has been written, the monitor processor software writes a 2-byte complementary code to the shared bootloader region, then causes the watchdog to be tripped.

Various IP messages are supported for transmission from the main processor to the monitor processor: (1) fire pump, (2) unfire pump, (3) alarm on, (4) alarm off, (5) new communication device ID, (6) audio change, (7) delivery IP message, (8) time change, (9) self-test, (10) time sync, (11) delivery error, and (12) read memory. These messages are discussed in more detail below.

The fire pump IP message signals to the monitor processor of the main processor's command that the pump mechanism be triggered. When the monitor processor receives a fire pump IP message, the monitor processor software checks for any programmed pump strokes using its own pump stroke calculations. If there is a pump stroke available, the monitor processor software fires the pump. If there are no pump strokes available, the monitor processor software prepares and sends an over-delivery error IP message to the main processor.

The unfire pump IP message is transmitted after a time that the main processor determines is sufficient for the monitor processor to have triggered the firing of the pump and the pump charge circuit to have been discharged. When the monitor processor receives an unfire pump IP message, the monitor processor software unlatches the pump firing circuit by clearing the pump fire bit.

The alarm on IP message causes the monitor processor software to initiate the alarm tone sequence if no other alarm tone sequence is currently in progress. The alarm off IP message causes the monitor processor software to cancel any current alarm tone sequence.

The delivery IP message provides an entire telemetry message including the CRC to the monitor processor. The telemetry message may be any of the delivery messages that are receivable by the main processor via telemetry: (1) set profile rates—the basal rates to be delivered during each of the 48 half hour periods of the day, (2) set temp basal rate, (3) deliver a bolus, and (4) set delivery mode. When the monitor processor receives a delivery IP message, the monitor processor software verifies the CRC of the embedded telemetry packet prior to using the values for pump stroke calculations. As the message would not have been passed on if the main processor had not already validated the message, If the message CRC is incorrect, the error is consider to be of a serious nature and as such the monitor processor software causes a 2-byte complementary code to be written and the watchdog to be tripped.

The new communication device ID IP message provides a 2-byte CRC seed which is composed of a 16-bit CRC containing the implantable device telemetry ID followed by the external communication device ID. This seed is in performing validation checks against IP messages containing delivery information.

The time change IP message provides the current half-hour number since midnight, and the current minute number within the half-hour that were received in a telemetry message from the communication device. The monitor processor software updates the monitor processor's current profile pointer to reflect the new half-hour and its minute counter to reflect the new minute value.

The self-test IP message causes the monitor processor software to initiate a CRC check of monitor processor program memory.

The time sync IP message is sent each half-hour of each day. When the monitor processor receives a time sync IP message, it sets its second value to zero.

The delivery error IP message sends the current delivery mode of the implantable device which indicates either no delivery or minimum delivery. When the monitor processor the message it zeros out the whole portion (i.e. integer portion) of the monitor processor's basal and phase-2 accumulators and its accumulator for immediate bolus pump strokes. If the delivery mode indicates no delivery, the monitor processor software also sets the fractional portion of basal and phase-2 pump strokes to zero.

The read memory IP message requests that a designated portion of the monitor processor memory be read and provided back to the main processor for transmission to the communication device. When the message is received, the monitor processor software prepares and sends a response message that contains the block of memory requested.

Various IP messages are supported from the monitor processor to the main processor: (1) over-delivery error, (2) under-delivery notification, and (3) read memory response—response to the read memory IP message.

The monitor processor and its application software are responsible for double-checking the main processor pump stroke calculations, firing of the pump circuitry, self-test of the monitor processor, and generation of internal implantable device alarm and diagnostic tones. The monitor processor software maintains delivery accumulators similar to those used by the main processor If the number of pump strokes available at the beginning of a minute is greater than 2 pump strokes and at the end of a minute 2 pump strokes have not been delivered, the monitor processor software prepares and sends an under-delivery notification IP message to the main processor.

If the monitor processor software receives a fire pump IP message and there are no whole pump stroke values in its phase-1 (immediate) bolus accumulator, its phase-2 bolus accumulator, or its basal accumulator, an over-delivery error IP message is prepared and sent to the main processor.

The monitor processor stores a number of constants in a block of memory that is shared between the monitor processor application software and the SSBS: (1) audio feedback frequency for alarm tones, (2) audio feedback duration for alarm tones, (3) single beep frequency for single-tone alarms, (4) single beep duration for single-tone alarms, (5) time between single beeps for single-tone alarms, (6) knee beep frequency knee portion of dual tone knee-gnu alarm patterns, (7) knee beep duration for the knee portion of the knee-gnu alarm patterns, (8) gnu beep frequency for the gnu portion of the knee-gnu alarm patterns, (9) gnu beep for the gnu portion of the knee-gnu alarm patterns, and (10) time between knee gnu beeps for knee-gnu alarm patterns.

The alarm on IP message triggers the monitor processor software to cause a sequence of alarm tones to occur on the minute boundaries. The sequence of alarm tones is programmed to change each 10 minutes. The initial sequence of alarm tones consists of 4 tones whose frequency is specified by single beep frequency for a duration specified by single beep duration spaced at an interval specified by time between single beeps. The sequence of alarm tones used for alternating 10 minute periods consists of 4 tone patterns in succession, where each tone pattern consists of a tone whose frequency is specified by the knee beep frequency for a duration specified by the knee beep duration, followed by a tone whose frequency is specified by the gnu beep frequency for a duration specified by the gnu beep duration. The time between each of these 4 tone patterns is for a duration specified by the time between knee gnu beeps.

While the above description has provided various teachings concerning how the implantable device may handle various RF telemetry operations, IP communication operations, alarm notifications, and other functional activities, many other such operations are definable. These other operations may be defined in manners that are analogous to the teachings presented above or in ways that are consistent with those teachings and do not lead to communication ambiguity or other potential mishandling of medical device operation.

The above embodiment and its alternatives provide numerous enhancements in the electronic control of the medical device. These improvements provide more functional, reliable, safe, user friendly, convenience operation of an implantable medical device and more generically of. an ambulatory medical device.

While the above embodiment has primarily been concerned with an implantable infusion pump that dispenses insulin using a piston type (i.e. pulsatile) pump mechanism, the electronic control features disclosed herein may be used in other ambulatory devices such as implantable pacemakers, defibrillators, other implantable tissue stimulators, implantable physiologic sensors such as electrochemical oxygen sensors, peroxide sensors, or enzymatic sensors such as glucose sensors, externally carried infusion pumps, implantable infusion pumps that use other pumping mechanisms or simply used excess pressure and controlled flow elements to infuse various medications and drugs such as analgesics, drugs for treating AIDS, drugs for treating psychological disorders and the like. For example, the features presented above may be used with an external infusion pump that may or may not have a built in display and keypad but is equipped with a telemetry system that can communicate with a physically separated communication device so that the pump need not be accessed in order to provide commands to it and receive data from it.

In these various alternatives, the physical, electronic, and programmed features of the communication device and implantable device may have different components and features than presented above for the implantable pump system so that their desired medical functionality and safety requirements are achieved and such that appropriate control and feedback is provided between the medical device and its communication device.

In other alternative embodiments the medical device may include two medical devices such as an implantable pump and an implantable sensor. The pump may dispense a drug whose physiological impact on the body (e.g. analgesic impact) is ascertained by the sensor or alternatively the sensor may supply a physiological reading that indicates a need for infusion of the drug. The pump may operate in a closed loop manner with the sensor or it may operate in an open loop manner where the patient is required to interpret sensor output information and is required to issue appropriate infusion commands to the pump. For example, in the case of a diabetic patient, the drug may be insulin and the sensor may detect glucose level.

In other alternative embodiments two medical devices may be implanted adjacent one another or at an extended distance from one another. If not placed in physical contact with one another, a lead may be used to provide power conduction from one device to the other and also be used to conduct communication signals between the devices. Alternatively, each device may include at least one telemetry system that allows direct communication between each or allows indirect communication to occur via the external communication device or other external device. Each device may be supplied with its own power supply. Depending on the communication requirements each device may use two way communication (i.e. both outbound and inbound communication) or allow only one way communication (i.e. outbound communication or possibly inbound communication).

In other alternatives, both the medical device and the communication device may be external devices (e.g. an external pump and an external RF telemetry based communication device). In still further alternatives, a first type of medical device may be implanted (e.g. an infusion pump or a sensor) while a second medical device may be external (e.g. the opposite of a sensor or an infusion pump). Where at least one of the medical devices is external, it may also function as the communication device for the other medical device in which case it may possess a display for providing information to the patient and a keypad for allowing entry of commands for issuance to the implantable device as well as for direct use by itself. Even if at least one of the medical devices is external, it may be inconvenient to access that device when information is needed or commands must be given, as such an external, non-medical communication device may be supplied that has information output (e.g. display) capabilities and input (e.g. keypad) capabilities. If a separate communication device is provided, the external medical device may or may not have display and input capabilities.

The telemetry features presented above may be used with various forms of distant communication (e.g. between the implantable device and other external devices or between the external communication device and other external devices). For example communication may occur via various electromagnetic links like IR, optical links, longer or shorter wavelength RF, audio links, ultrasonic links, acoustic links, inductive links, and the like. Various telemetry systems may be used. Telemetry systems may be of the analog type, digital type, or mixed.

In other embodiments two independent processors may be used that operate from a single timing chain. In these alternatives, it is preferable that at least one of the timing signals (e.g. one of the lower frequency timers) be monitored by an independently timed watchdog circuit to reduce the risk of timing problems going undetected.

In still additional embodiments, an implantable glucose sensor may be used in conjunction with an implantable insulin pump to provide feedback to the patient or physician on the effectiveness of the insulin delivery system. The patient could use the feedback to assist in making insulin delivery decisions in an open loop manner. Alternatively, the operation of the pump could be tied to the sensor output in a more or less closed loop manner to give a more automated character to system operation. Insulin may be infused without any user intervention, without pre-delivery information, and even without direct post delivery feedback. In a less automated closed loop system, drug infusion recommendations could be derived by the system and presented to the user before delivery or the system could require user acknowledgment prior to proceeding with delivery for amounts or rates exceed a predefined limit. The implantable sensor may have its own power supply or may receive power from the control circuitry provided within the pump housing through a physical lead that connects them. Power may be supplied through one or more independent leads or alternatively may be transferred over one or more data lines through the communication signals themselves. Communication may be exchanged in various ways including, for example, via galvanic leads, RF telemetry, fiber optics, and the like, and may be of digital, analog, or combined form. The sensor system may include a plurality of sensor elements which might allow continued glucose data to be supplied even though some portion of the sensors stop operating, lose calibration or produce questionable readings. The most preferred sensors would include electronic processing capability in the form of an integrated circuit mounted in or forming a part of a housing for the sensor. This configuration has the advantage of allowing digital communications between the physical sensor and any separated electronic control module.

Further teachings concerning implantable sensors and implantable sensor systems are found in a number of patents issued to D. A. Gough, including (1) U.S. Pat. No. 4,484,987, entitled "Method And Membrane Applicable To Implantable Sensor"; (2) U.S. Pat. No. 4,627,906, entitled "Electrochemical Sensor Having Improved Stability"; (3) U.S. Pat. No. 4,671,288, entitled "Electrochemical Cell Sensor For Continuous Short-Term Use In Tissues And Blood"; (4) U.S. Pat. No. 4,703,756, entitled "Complete Glucose Monitoring System With An Implantable Telemetered Sensor Module"; and (5) U.S. Pat. No. 4,781,798, entitled "Transparent Multi-Oxygen Sensor Array And Method Of Using Same". Each of these patents is incorporated herein by reference as if set forth in full.

Still further teachings concerning implantable sensors and sensor systems are found in a number of patents issued to J. H. Schulman, et al., including (1) U.S. Pat. No. 5,497,772, entitled "Glucose Monitoring System"; (2) U.S. Pat. No. 5,651,767, entitled "Replaceable Catheter System for Physiological Sensors, Stimulating Electrodes and/or Implantable Fluid Delivery Systems"; (3) U.S. Pat. No. 5,750,926, entitled "Hermetically Sealed Electrical Feedthrough For Use With Implantable Electronic Devices"; (4) U.S. Pat. No. 6,043,437, entitled "Alumina Insulation for Coating Implantable Components and Other Microminiature Devices"; (5) U.S. Pat. 6,088,608, entitled "Implantable Sensor and Integrity Test Therefor"; and (6) U.S. Pat. 6,119,028, entitled "Implantable Enzyme-Based Monitoring Systems Having Improved Longevity Due to Improved Exterior Surfaces". Each of these patents is incorporated herein by reference as if set forth in full.

Additional further teachings concerning implantable sensors and sensor systems are found in (1) U.S. Pat. No. 5,917,346, issued to J. C. Gord, et al., and entitled "Low power current-to-frequency converter"; (2) U.S. Pat. No. 5,999,848, issued to J. C. Gord, and entitled "Daisy Chainable Sensors for Implantation in Living Tissue"; (3) U.S. Pat. 5,999,849, issued to L. D. Canfield, et al., and entitled "Low Power Rectifier Circuit for Implantable Medical Devices"; and (4) U.S. Pat. No. 6,081,736, issued to M. S. Colvin, et al., and entitled "Implantable Enzyme-Based Monitoring Systems Adapted for Long Term Use". Each of these patents is incorporated herein by reference as if set forth in full.

Further teachings concerning implantable infusion pumps are found in a number of patents by R. E. Fischell, including (1) U.S. Pat. No. 4,373,527, entitled "Implantable, Programmable Medication Infusion System"; (2) U.S. Pat. No. 4,494,950, entitled. "Infusion Device Intended for Implantation in a Living Body"; (3) U.S. Pat. No. 4,525,165, entitled "Fluid Handling System for Medication Infusion System"; (4) U.S. Pat. No. 4,573,994, entitled "Refillable Medication Infusion Apparatus"; (5) U.S. Pat. No. 4,594,058, entitled "Single Valve Diaphragm Pump with Decreased Sensitivity to Ambient Conditions"; (6) U.S. Pat. No. 4,619,653, entitled "Apparatus For Detecting At Least One Predetermined Condition And Providing An Informational Signal In Response Thereto In A Medication Infusion System"; (7) U.S. Pat. No. 4,661,097, entitled "Method for Clearing a Gas Bubble From a Positive Displacement Pump Contained Within a Fluid Dispensing System"; (8) U.S. Pat. No. 4,731,051, entitled "Programmable Control Means for Providing Safe and Controlled Medication Infusion"; and (9) U.S. Pat. No. 4,784,645, entitled, "Apparatus For Detecting A Condition Of A Medication Infusion System And Providing An Informational Signal In Response Thereto". Each of these patents is incorporated herein by reference as if set forth in full.

Still further teachings concerning infusion pumps are found in a number of patents by Franetzki, including (1) U.S. Pat. No. 4,191,181, entitled "Apparatus For Infusion of Liquids", (2) U.S. Pat. No. 4,217,894, entitled "Apparatus for Supplying Medication to the Human or Animal Body"; (3) U.S. Pat. No. 4,270,532, entitled "Device for the Pre-programmable Infusion of Liquids"; (4) U.S. Pat. No. 4,282,872, entitled "Device for the Pre-programmable Infusion of Liquids", U.S. Pat. No. 4,373,527, entitled "Implantable, Programmable Medication Infusion System"; (5) U.S. Pat. No. 4,511,355, entitled "Plural Module Medication Delivery System", (6) U.S. Pat. No. 4,559,037, entitled "Device for the Pre-programmable Infusion of Liquids"; (7) U.S. Pat. No. 4,776,842, entitled "Device for the Administration of Medications". Each of these patents is incorporated herein by reference as if set forth in full.

Teachings concerning tissue stimulators are found in a number of patents by J. H. Schulman, including (1) U.S. Pat. No. 5,193,539, entitled "Implantable microstimulator"; (2) U.S. Pat. No. 5,193,540; entitled "Structure and Method of Manufacture of an Implantable Microstimulator"; and (3) U.S. Pat. No. 5,358,514, entitled "Implantable Microdevices with Self Attaching Electrodes". Further teachings are also found in (1) U.S. Pat. No. 5,957,958, by Loeb et al., entitled "Implantable nerve or muscle stimulator e.g. a cochlear prosthesis", in (2) U.S. Pat. No. 5,571,148, by G. E. Loeb, et al., entitled "Implantable Multichannel Stimulator"; and in (3) PCT Publication No. WO 00/74751, by A. E. Mann, and entitled "Method and Apparatus for Infusing Liquids Using a Chemical Reaction in an Implanted Infusion Device". Each of these publications is incorporated herein by reference as if set forth in full.

The control of an implantable sensor could be provided through the functionality of one or both Processor ICs. One Processor IC could supply power and/or control signals to the sensor(s) and receive data back from the sensor, while the other processor could monitor the activity to ensure that sensor activity meets certain predefined guidelines.

In other embodiments, the External Communication Device of the first embodiment could be functionally linked to an external glucose sensor system such as the continuous glucose monitoring system (CGMS) offered by Minimed Inc. of Northridge, Calif. The link may be established, for example, through a physical lead or by RF telemetry.

In other embodiments other implantable, or external, sensor systems that measure something other than glucose could also be functionally coupled to the implantable device either to receive power and/or to provide data. Other such sensors might include oxygen sensors, peroxide sensors, pulse rate sensors, temperature sensors, accelerometers, and the like.

In still other alternative embodiments, the electronic control system of the first embodiment could be configured to control one or more implantable sensors or electrical stimulators with or without infusion functionality incorporated into the implantable device.

Further embodiments will be apparent to those of skill in the art upon review of the disclosure provided herein. Still further embodiments may be derived from the teachings set forth explicitly herein in combination with the teachings found in the various patent applications.

While the description herein sets forth particular embodiments, it is believed that those of skill in the art will recognize many variations to the presented embodiments based on the teachings herein, as such it is believed that many additional modifications may be made without departing from the spirit of the teachings herein. The accompanying claims are intended to cover such modifications as would fall within the true scope and spirit of the present invention. The disclosed embodiments are therefore to be considered as illustrative and not necessarily restrictive, the scope of the invention being indicated by the appended claims, rather than the foregoing description, and all changes which come within the meaning and range of equivalency of the claims are therefore intended to be embraced therein.

We claim:

1. A medical system, comprising:
   a) an ambulatory medical device (MD) comprising MD electronic control circuitry that further comprises at least one MD telemetry system and at least one MD processor that controls, at least in part, operation of the MD telemetry system and operation of the medical device, wherein the medical device is configured to provide a treatment to a body of a patient or to monitor a selected state of the body; and
   b) a communication device (CD) comprising CD electronic control circuitry that further comprises at least one CD telemetry system and at least one CD processor that controls, at least in part, operation of the CD telemetry system and operation of the communication device, wherein the CD telemetry system sends messages to or receives messages from the MD telemetry system,
   wherein the medical device further comprises an MD alarm under control of the MD processor, and the communication device further comprises a CD alarm under control of the CD processor, and wherein the communication device is programmed to activate the CD alarm, in a selected circumstance, prior to the medical device directly sounding the MD alarm, such that a patient is signaled that a selected circumstance will occur, thereby providing an opportunity for the patient to acknowledge the selected circumstance so that the MD alarm may be de-asserted or the selected circumstance removed prior to the physical sounding of the MD alarm.

2. The system of claim 1 wherein the medical device comprises at least one of (1) an implantable infusion pump for selectively dispensing a selected drug, (2) an implantable infusion pump for selectively dispensing insulin, (3) an implantable sensor for sensing a selected state of the body, (4) an implantable sensor for sensing glucose level, or (5) an implantable electrode for selectively stimulating a portion of the body of the patient.

3. The system of claim 1 wherein a first portion of the MD telemetry system is incorporated into the MD processor and a second portion of the MD telemetry system is external to the MD processor, or wherein a first portion of the CD telemetry system is incorporated into the CD processor and a second portion of the CD telemetry system is external to the CD processor.

4. The system of claim 3 wherein (1) the MD electronic control circuitry comprises at least one external MD functional module, other than the second portion of the MD telemetry system, that is external to the MD processor, (2) the CD electronic control circuitry comprises at least one external CD functional module, other than the second portion of the CD telemetry system, that is external to the CD processor, (3) the MD processor comprises an internal MD CPU and at least one other internal MD functional module, or (4) the CD processor comprises an internal CD CPU and at least one other internal CD functional module.

5. The system of claim 1 wherein a first portion of the MD telemetry system is incorporated into the MD processor and a second portion of the MD telemetry system is external to the MD processor, or wherein a first portion of the CD telemetry system is incorporated into the CD processor and a second portion of the CD telemetry system is external to the CD processor.

6. The system of claim 5 wherein the MD electronic control circuitry comprises at least one external MD functional module, other than the second portion of the MD telemetry system, that is external to the MD processor, and wherein the CD electronic control circuitry comprises at least one external CD functional module, other than the second portion of the CD telemetry system, that is external to the CD processor.

7. The system of claim 6 wherein the MD processor comprises an MD central processing unit and at least one other MD functional module, and wherein the CD processor comprises a CD central processing unit and at least one other CD functional module.

8. A medical system, comprising:
   a) an ambulatory medical device (MD) comprising MD electronic control circuitry that further comprises at least one MD telemetry system and at least one MD processor that controls, at least in part, operation of the MD telemetry system and operation of the medical device, wherein the medical device is configured to provide a treatment to a body of a patient or to monitor a selected state of the body; and
   b) a communication device (CD) comprising CD electronic control circuitry that further comprises at least one CD telemetry system and at least one CD processor that controls, at least in part, operation of the CD telemetry system and operation of the communication device, wherein the CD telemetry system sends messages to or receives messages from the MD telemetry system,
   wherein at least one of the medical device or the communication device is configured to allow selected alarm conditions to be cleared without removing the alarm condition, and wherein at least one type of alarm is reasserted after clearing if the alarm condition has not been eliminated within a predefined period of time.

9. The system of claim 8 wherein the medical device comprises at least one of (1) an implantable infusion pump for selectively dispensing a selected drug, (2) an implantable infusion pump for selectively dispensing insulin, (3) an implantable sensor for sensing a selected state of the body, (4) an implantable sensor for sensing glucose level, or (5) an implantable electrode for selectively stimulating a portion of the body of the patient.

10. The system of claim 8 wherein a first portion of the MD telemetry system is incorporated into the MD processor and a second portion of the MD telemetry system is external to the MD processor, or wherein a first portion of the CD telemetry system is incorporated into the CD processor and a second portion of the CD telemetry system is external to the CD processor.

11. The system of claim 10 wherein (1) the MD electronic control circuitry comprises at least one external MD functional module, other than the second portion of the MD telemetry system, that is external to the MD processor, (2) the CD electronic control circuitry comprises at least one external CD functional module, other than the second portion of the CD telemetry system, that is external to the CD processor, (3) the MD processor comprises an internal MD CPU and at least one other internal MD functional module, or (4) the CD processor comprises an internal CD CPU and at least one other internal CD functional module.

12. The system of claim 8 wherein a first portion of the MD telemetry system is incorporated into the MD processor and a second portion of the MD telemetry system is external to the MD processor, or wherein a first portion of the CD telemetry system is incorporated into the CD processor and a second portion of the CD telemetry system is external to the CD processor.

13. The system of claim 12 wherein the MD electronic control circuitry comprises at least one external MD functional module, other than the second portion of the MD telemetry system, that is external to the MD processor, and wherein the CD electronic control circuitry comprises at least one external CD functional module, other than the second portion of the MD telemetry system, that is external to the CD processor.

14. The system of claim 13 wherein the MD processor comprises an MD central processing unit and at least one other MD functional module, and wherein the CD processor comprises a CD central processing unit and at least one other CD functional module.

15. A medical system, comprising:
  a) an ambulatory medical device (MD) comprising MD electronic control circuitry that further comprises at least one MD telemetry system and at least one MD processor that controls, at least in part, operation of the MD telemetry system and operation of the medical device, wherein the medical device is configured to provide a treatment to a body of a patient or to monitor a selected state of the body; and
  b) a communication device (CD) comprising CD electronic control circuitry that further comprises at least one CD telemetry system and at least one CD processor that controls, at least in part, operation of the CD telemetry system and operation of the communication device, wherein the CD telemetry system sends messages to or receives messages from the MD telemetry system,
  wherein at least one of the medical device or the communication device may present a plurality of alarm conditions which are prioritized for display in a predetermined order.

16. The system of claim 15 wherein the medical device comprises at least one of (1) an implantable infusion pump for selectively dispensing a selected drug, (2) an implantable infusion pump for selectively dispensing insulin, (3) an implantable sensor for sensing a selected state of the body, (4) an implantable sensor for sensing glucose level, or (5) an implantable electrode for selectively stimulating a portion of the body of the patient.

17. The system of claim 15 wherein the medical device comprises an implantable electrode for selectively stimulating a portion of the body of the patient.

18. The system of claim 15 wherein a first portion of the MD telemetry system is incorporated into the MD processor and a second portion of the MD telemetry system is external to the MD processor, or wherein a first portion of the CD telemetry system is incorporated into the CD processor and a second portion of the CD telemetry system is external to the CD processor.

19. The system of claim 18 wherein (1) the MD electronic control circuitry comprises at least one external MD functional module, other than the second portion of the MD telemetry system, that is external to the MD processor, (2) the CD electronic control circuitry comprises at least one external CD functional module, other than the second portion of the CD telemetry system, that is external to the CD processor, (3) the MD processor comprises an internal MD CPU and at least one other internal MD functional module, or (4) the CD processor comprises an internal CD CPU and at least one other internal CD functional module.

20. The system of claim 15 wherein a first portion of the MD telemetry system is incorporated into the MD processor and a second portion of the MD telemetry system is external to the MD processor, or wherein a first portion of the CD telemetry system is incorporated into the CD processor and a second portion of the CD telemetry system is external to the CD processor.

21. The system of claim 20 wherein the MD electronic control circuitry comprises at least one external MD functional module, other than the second portion of the MD telemetry system, that is external to the MD processor, and wherein the CD electronic control circuitry comprises at least one external CD functional module, other than the second portion of the MD telemetry system, that is external to the CD processor.

22. The system of claim 21 wherein the MD processor comprises an MD central processing unit and at least one other MD functional module, and wherein the CD processor comprises a CD central processing unit and at least one other CD functional module.

23. A medical system, comprising:
  a) an ambulatory medical device (MD) comprising MD electronic control circuitry that further comprises at least one MD telemetry system and at least one MD processor that controls, at least in part, operation of the MD telemetry system and operation of the medical device, wherein the medical device is configured to provide a treatment to a body of a patient or to monitor a selected state of the body; and
  b) a communication device (CD) comprising CD electronic control circuitry that further comprises at least one CD telemetry system and at least one CD processor that controls, at least in part, operation of the CD telemetry system and operation of the communication device, wherein the CD telemetry system sends messages to or receives messages from the MD telemetry system,
  wherein at least one of the medical device or communication device comprises an alarm that is activated in response to a selected alarm condition using a first set of alarm parameters, and wherein at least one of the alarm parameters is changed when the condition is not cleared within a predetermined period of time.

24. The system of claim 23 wherein the alarm parameters include at least one of a frequency, a volume, a duration, or a repetition pattern.

25. The system of claim 23 wherein the medical device comprises at least one of (1) an implantable infusion pump for selectively dispensing a selected drug, (2) an implantable infusion pump for selectively dispensing insulin, (3) an implantable sensor for sensing a selected state of the body, (4) an implantable sensor for sensing glucose level, or (5) an implantable electrode for selectively stimulating a portion of the body of the patient.

26. The system of claim 23 wherein a first portion of the MD telemetry system is incorporated into the MD processor and a second portion of the MD telemetry system is external to the MD processor, or wherein a first portion of the CD telemetry system is incorporated into the CD processor and a second portion of the CD telemetry system is external to the CD processor.

27. The system of claim 26 wherein (1) the MD electronic control circuitry comprises at least one external MD functional module, other than the second portion of the MD telemetry system, that is external to the MD processor, (2) the CD electronic control circuitry comprises at least one external CD functional module, other than the second portion of the CD telemetry system, that is external to the CD processor, (3) the MD processor comprises an internal MD CPU and at least one other internal MD functional module, or (4) the CD processor comprises an internal CD CPU and at least one other internal CD functional module.

28. The system of claim 23 wherein a first portion of the MD telemetry system is incorporated into the MD processor and a second portion of the MD telemetry system is external to the MD processor, or wherein a first portion of the CD telemetry system is incorporated into the CD processor and a second portion of the CD telemetry system is external to the CD processor.

29. The system of claim 28 wherein the MD electronic control circuitry comprises at least one external MD functional module, other than the second portion of the MD telemetry system, that is external to the MD processor, and wherein the CD electronic control circuitry comprises at least one external CD functional module, other than the second portion of the MD telemetry system, that is external to the CD processor.

30. The system of claim 27 wherein the MD processor comprises an MD central processing unit and at least one other MD functional module, and wherein the CD processor comprises a CD central processing unit and at least one other CD functional module.

31. A medical system, comprising:
 a) an ambulatory medical device (MD) comprising MD electronic control circuitry that further comprises at least one MD telemetry system and at least one MD processor that controls, at least in part, operation of the MD telemetry system and operation of the medical device, wherein the medical device is configured to provide a treatment to a body of a patient or to monitor a selected state of the body; and
 b) a communication device (CD) comprising CD electronic control circuitry that further comprises at least one CD telemetry system and at least one CD processor that controls, at least in part, operation of the CD telemetry system and operation of the communication device, wherein the CD telemetry system sends messages to or receives messages from the MD telemetry system,
 wherein the MD processor uses a stack in conjunction with a central processing unit and wherein occurrence of a stack overflow causes the MD processor to be placed in a known state.

32. The system of claim 31 wherein the medical device comprises at least one of (1) an implantable infusion pump for selectively dispensing a selected drug, (2) an implantable infusion pump for selectively dispensing insulin, (3) an implantable sensor for sensing a selected state of the body, (4) an implantable sensor for sensing glucose level, or (5) an implantable electrode for selectively stimulating a portion of the body of the patient.

33. The system of claim 31 wherein the known state is reached by resetting the processor.

34. The system of claim 31 wherein the medical device includes memory having valid addresses that are accessible to a central processing unit within the MD processor, wherein the stack has predefined memory locations including a final memory location having a final memory address, and wherein a next memory address after the final memory address is an invalid memory address, and wherein a stack overflow directs the central processing unit to the invalid memory address which causes a non-maskable interrupt that in turn causes the MD processor to be placed in the known state.

35. The system of claim 31 wherein a first portion of the MD telemetry system is incorporated into the MD processor and a second portion of the MD telemetry system is external to the MD processor, or wherein a first portion of the CD telemetry system is incorporated into the CD processor and a second portion of the CD telemetry system is external to the CD processor.

36. The system of claim 35 wherein (1) the MD electronic control circuitry comprises at least one external MD functional module, other than the second portion of the MD telemetry system, that is external to the MD processor, (2) the CD electronic control circuitry comprises at least one external CD functional module, other than the second portion of the CD telemetry system, that is external to the CD processor, (3) the MD processor comprises an internal MD CPU and at least one other internal MD functional module, or (4) the CD processor comprises an internal CD CPU and at least one other internal CD functional module.

37. The system of claim 31 wherein a first portion of the MD telemetry system is incorporated into the MD processor and a second portion of the MD telemetry system is external to the MD processor, or wherein a first portion of the CD telemetry system is incorporated into the CD processor and a second portion of the CD telemetry system is external to the CD processor.

38. The system of claim 37 wherein the MD electronic control circuitry comprises at least one external MD functional module, other than the second portion of the MD telemetry system, that is external to the MD processor, and wherein the CD electronic control circuitry comprises at least one external CD functional module, other than the second portion of the MD telemetry system, that is external to the CD processor.

39. The system of claim 38 wherein the MD processor comprises an MD central processing unit and at least one other MD functional module, and wherein the CD processor comprises a CD central processing unit and at least one other CD functional module.

40. A medical system, comprising:
 a) an ambulatory medical device (MD) comprising MD electronic control circuitry that further comprises at least one MD telemetry system and at least one MD processor that controls, at least in part, operation of the MD telemetry system and operation of the medical device, wherein the medical device is configured to provide a treatment to a body of a patient or to monitor a selected state of the body; and
 b) a communication device (CD) comprising CD electronic control circuitry that further comprises at least one CD telemetry system and at least one CD processor that controls, at least in part, operation of the CD telemetry system and operation of the communication device, wherein the CD telemetry system sends messages to or receives messages from the MD telemetry system,
 wherein at least one MD watchdog circuit is capable of causing at least one MD processor to undergo a predefined process in the event that the watchdog circuit does not receive a first signal and a second signal, which is different from the first signal, within a predefined or programmable time period.

41. The system of claim 40 wherein the medical device comprises at least one of (1) an implantable infusion pump for selectively dispensing a selected drug, (2) an implantable infusion pump for selectively dispensing insulin, (3) an implantable sensor for sensing a selected state of the body, (4) an implantable sensor for sensing glucose level, or (5) an implantable electrode for selectively stimulating a portion of the body of the patient.

42. The system of claim 40 wherein a first portion of the MD telemetry system is incorporated into the MD processor and a second portion of the MD telemetry system is external to the MD processor, or wherein a first portion of the CD telemetry system is incorporated into the CD processor and a second portion of the CD telemetry system is external to the CD processor.

43. The system of claim 42 wherein (1) the MD electronic control circuitry comprises at least one external MD functional module, other than the second portion of the MD telemetry system, that is external to the MD processor, (2) the CD electronic control circuitry comprises at least one external CD functional module, other than the second portion of the CD telemetry system, that is external to the CD processor, (3) the MD processor comprises an internal MD CPU and at least one other internal MD functional module, or (4) the CD processor comprises an internal CD CPU and at least one other internal CD functional module.

44. The system of claim 40 wherein a first portion of the MD telemetry system is incorporated into the MD processor and a second portion of the MD telemetry system is external to the MD processor, or wherein a first portion of the CD telemetry system is incorporated into the CD processor and a second portion of the CD telemetry system is external to the CD processor.

45. The system of claim 44 wherein the MD electronic control circuitry comprises at least one external MD functional module, other than the second portion of the MD telemetry system, that is external to the MD processor, and wherein the CD electronic control circuitry comprises at least one external CD functional module, other than the second portion of the MD telemetry system, that is external to the CD processor.

46. The system of claim 45 wherein the MD processor comprises an MD central processing unit and at least one other MD functional module, and wherein the CD processor comprises a CD central processing unit and at least one other CD functional module.

47. The system of claim 40 wherein the predefined process causes the MD processor to be reset.

48. The system of claim 47 wherein one of the first or second signals is a signal generated by mainline software.

49. The system of claim 48 wherein the other of the first or second signals is a signal generated by interrupt hardware.

* * * * *